United States Patent
Wallace et al.

(10) Patent No.: US 10,888,343 B2
(45) Date of Patent: Jan. 12, 2021

(54) ANTI-JAMMING AND MACERATING THROMBECTOMY APPARATUSES AND METHODS

(71) Applicant: STRYKER CORPORATION, Fremont, CA (US)

(72) Inventors: Michael P. Wallace, Pleasanton, CA (US); E. Skott Greenhalgh, Gladwyne, PA (US); Robert Garabedian, Mountain View, CA (US)

(73) Assignee: Stryker Corporation, Fremont, CA (US)

( * ) Notice: Subject to any disclaimer, the term of this patent is extended or adjusted under 35 U.S.C. 154(b) by 33 days.

(21) Appl. No.: 16/169,334

(22) Filed: Oct. 24, 2018

(65) Prior Publication Data
US 2019/0117244 A1   Apr. 25, 2019

Related U.S. Application Data

(63) Continuation of application No. PCT/US2017/029345, filed on Apr. 25, 2017.
(Continued)

(51) Int. Cl.
*A61B 17/22* (2006.01)
*A61B 17/221* (2006.01)
(Continued)

(52) U.S. Cl.
CPC ...... *A61B 17/22031* (2013.01); *A61B 17/221* (2013.01); *A61B 17/32075* (2013.01);
(Continued)

(58) Field of Classification Search
CPC ............ A61B 17/22031; A61B 17/221; A61B 17/320725; A61B 17/32075;
(Continued)

(56) References Cited

U.S. PATENT DOCUMENTS 4,222,380 A   9/1980   Terayama
4,243,040 A   1/1981   Beecher
(Continued)

FOREIGN PATENT DOCUMENTS

AU   2015210338   8/2015
GB   1588072   4/1981
(Continued)

OTHER PUBLICATIONS

Non-Final Office Action for U.S. Appl. No. 15/496,570, dated Aug. 9, 2017.
(Continued)

*Primary Examiner* — Melanie R Tyson
(74) *Attorney, Agent, or Firm* — Vista IP Law Group, LLP

(57) ABSTRACT

Mechanical thrombectomy apparatuses that may be configured to prevent or reduce jamming (e.g., "anti-jamming" thrombectomy devices), grab clot, and/or macerate the thrombus, e.g., clot, being removed. These mechanical thrombectomy apparatuses may include a tractor comprising a flexible tube of material that inverts as it rolls over itself while being drawn into a catheter in a conveyor-like motion. In particular, described herein are mechanical thrombectomy apparatuses having tractors selectably extendable projections that may aid in grabbing and/or macerating a clot. Also described herein are seesawing tractors for mechanical thrombectomy apparatuses.

14 Claims, 33 Drawing Sheets

Related U.S. Application Data

(60) Provisional application No. 62/393,460, filed on Sep. 12, 2016, provisional application No. 62/345,152, filed on Jun. 3, 2016, provisional application No. 62/327,024, filed on Apr. 25, 2016.

(51) Int. Cl.
  *A61B 17/3207* (2006.01)
  *A61B 17/34* (2006.01)
  *A61B 17/32* (2006.01)

(52) U.S. Cl.
  CPC .............. *A61B 17/320725* (2013.01); *A61B 2017/22001* (2013.01); *A61B 2017/2215* (2013.01); *A61B 2017/22034* (2013.01); *A61B 2017/22079* (2013.01); *A61B 2017/320064* (2013.01); *A61B 2017/3435* (2013.01)

(58) Field of Classification Search
  CPC .. A61B 2017/2215; A61B 2017/22001; A61B 2017/22034; A61B 2017/320064; A61B 2017/3435
  See application file for complete search history.

(56) References Cited

U.S. PATENT DOCUMENTS

| | | |
|---|---|---|
| 4,324,262 A | 4/1982 | Hall |
| 4,469,100 A | 9/1984 | Hardwick |
| 4,604,094 A | 8/1986 | Shook |
| 4,646,736 A | 3/1987 | Auth |
| 4,863,440 A | 9/1989 | Chin |
| 4,946,440 A | 8/1990 | Hall |
| 5,329,923 A | 7/1994 | Lundquist |
| 5,364,345 A | 11/1994 | Lowery et al. |
| 5,389,100 A | 2/1995 | Bacich et al. |
| 5,662,703 A | 9/1997 | Yurek et al. |
| 5,971,938 A | 10/1999 | Hart et al. |
| 6,156,055 A | 12/2000 | Ravenscroft |
| 6,221,006 B1 | 4/2001 | Dubrul et al. |
| 6,238,412 B1 | 5/2001 | Dubrul et al. |
| 6,245,078 B1 | 6/2001 | Ouchi |
| 6,258,115 B1 | 7/2001 | Dubrul |
| 6,544,278 B1 | 4/2003 | Vrba et al. |
| 6,569,181 B1 | 5/2003 | Burns |
| 6,620,179 B2 | 9/2003 | Brook et al. |
| 6,635,068 B1 | 10/2003 | Dubrul et al. |
| 6,635,070 B2 | 10/2003 | Leeflang et al. |
| 6,830,561 B2 | 12/2004 | Jansen et al. |
| 6,846,029 B1 | 1/2005 | Ragner et al. |
| 6,942,682 B2 | 9/2005 | Vrba et al. |
| 7,621,870 B2 | 11/2009 | Berrada et al. |
| 7,780,696 B2 | 8/2010 | Daniel et al. |
| 8,057,496 B2 | 11/2011 | Fischer, Jr. |
| 8,070,769 B2 | 12/2011 | Broome |
| 8,092,486 B2 | 1/2012 | Berrada et al. |
| 8,657,867 B2 | 2/2014 | Dorn et al. |
| 8,721,714 B2 | 5/2014 | Kelley |
| 8,784,442 B2 | 7/2014 | Jones et al. |
| 8,795,305 B2 | 8/2014 | Martin et al. |
| 8,956,384 B2 | 2/2015 | Berrada et al. |
| 9,028,401 B1 | 5/2015 | Bacich et al. |
| 9,125,683 B2 | 9/2015 | Farhangnia et al. |
| 9,126,016 B2 | 9/2015 | Fulton |
| 9,155,552 B2 | 10/2015 | Ulm, III |
| 9,173,668 B2 | 11/2015 | Ulm, III |
| 9,186,487 B2 | 11/2015 | Dubrul et al. |
| 9,358,037 B2 | 1/2016 | Farhangnia et al. |
| 9,259,237 B2 | 2/2016 | Quick et al. |
| 9,351,747 B2 | 5/2016 | Kugler et al. |
| 9,463,035 B1 | 10/2016 | Greenhalgh et al. |
| 9,717,514 B2 | 8/2017 | Martin et al. |
| 9,848,975 B2 | 12/2017 | Hauser |
| 9,849,014 B2 | 12/2017 | Kusleika |
| 9,962,178 B2 | 5/2018 | Greenhalgh et al. |
| 1,001,033 A1 | 7/2018 | Greenhalgh et al. |
| 1,001,626 A1 | 7/2018 | Hauser |
| 1,002,875 A1 | 7/2018 | Wallace et al. |
| 1,013,038 A1 | 11/2018 | Farhangnia et al. |
| 1,027,186 A1 | 4/2019 | Greenhalgh et al. |
| 10,327,883 B2 | 6/2019 | Yachia |
| 2002/0032455 A1 | 3/2002 | Boock et al. |
| 2002/0173819 A1 | 11/2002 | Leeflang et al. |
| 2003/0083693 A1 | 5/2003 | Daniel et al. |
| 2003/0135258 A1 | 7/2003 | Andreas et al. |
| 2003/0153873 A1 | 8/2003 | Luther et al. |
| 2003/0176884 A1 | 9/2003 | Berrada et al. |
| 2003/0208224 A1 | 11/2003 | Broome |
| 2004/0098033 A1 | 5/2004 | Leeflang et al. |
| 2005/0085826 A1 | 4/2005 | Nair et al. |
| 2005/0085849 A1 | 4/2005 | Sepetka et al. |
| 2005/0119668 A1 | 6/2005 | Teague et al. |
| 2005/0177132 A1 | 8/2005 | Lentz et al. |
| 2005/0187570 A1 | 8/2005 | Nguyen et al. |
| 2005/0283166 A1 | 12/2005 | Greenhalgh |
| 2005/0283186 A1 | 12/2005 | Berrada et al. |
| 2006/0042786 A1 | 3/2006 | West |
| 2006/0089533 A1 | 4/2006 | Ziegler et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0276874 A1 | 12/2006 | Wilson et al. |
| 2006/0293696 A1 | 12/2006 | Fahey et al. |
| 2007/0112374 A1 | 5/2007 | Paul, Jr. et al. |
| 2007/0149996 A1 | 6/2007 | Coughlin |
| 2007/0213765 A1 | 9/2007 | Adams et al. |
| 2008/0183136 A1 | 7/2008 | Lenker et al. |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0137846 A1 | 6/2010 | Desaietal |
| 2010/0190156 A1 | 7/2010 | Van Wordragen et al. |
| 2010/0249815 A1* | 9/2010 | Jantzen ............ A61B 17/22031 606/159 |
| 2011/0034987 A1 | 2/2011 | Kennedy |
| 2011/0118817 A1 | 5/2011 | Gunderson et al. |
| 2011/0160763 A1 | 6/2011 | Ferrera et al. |
| 2011/0265681 A1 | 11/2011 | Allen et al. |
| 2011/0288529 A1 | 11/2011 | Fulton |
| 2011/0288572 A1 | 11/2011 | Martin |
| 2012/0083824 A1 | 4/2012 | Berrada et al. |
| 2012/0083868 A1 | 4/2012 | Shrivastava |
| 2012/0271105 A1 | 10/2012 | Nakamura et al. |
| 2013/0046332 A1 | 2/2013 | Jones et al. |
| 2013/0096571 A1 | 4/2013 | Massicotte et al. |
| 2013/0116721 A1 | 5/2013 | Takagi et al. |
| 2013/0226196 A1 | 8/2013 | Smith |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0046133 A1 | 2/2014 | Nakamura et al. |
| 2014/0155980 A1 | 6/2014 | Turjman |
| 2014/0257253 A1 | 9/2014 | Jemison |
| 2014/0276403 A1 | 9/2014 | Follmer et al. |
| 2014/0330286 A1 | 11/2014 | Wallace |
| 2014/0336691 A1 | 11/2014 | Jones et al. |
| 2014/0364896 A1 | 12/2014 | Consigny |
| 2014/0371779 A1 | 12/2014 | Vale et al. |
| 2015/0005781 A1* | 1/2015 | Lund-Clausen ..... A61B 17/221 606/127 |
| 2015/0005792 A1 | 1/2015 | Ahn |
| 2015/0018859 A1 | 1/2015 | Quick et al. |
| 2015/0018860 A1 | 1/2015 | Quick et al. |
| 2015/0088190 A1 | 3/2015 | Jensen |
| 2015/0164523 A1 | 6/2015 | Brady et al. |
| 2015/0164666 A1 | 6/2015 | Johnson et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2016/0022293 A1 | 1/2016 | Dubrul et al. |
| 2016/0058540 A1 | 3/2016 | Don Michael |
| 2016/0074627 A1 | 3/2016 | Cottone |
| 2016/0106448 A1 | 4/2016 | Brady et al. |
| 2016/0106449 A1 | 4/2016 | Brady et al. |

(56) References Cited

U.S. PATENT DOCUMENTS

| | | | |
|---|---|---|---|
| 2016/0113663 | A1 | 4/2016 | Brady et al. |
| 2016/0113664 | A1 | 4/2016 | Brady et al. |
| 2016/0113665 | A1 | 4/2016 | Brady et al. |
| 2017/0086864 | A1 | 3/2017 | Greenhalgh et al. |
| 2017/0100142 | A1 | 4/2017 | Look et al. |
| 2017/0105743 | A1 | 4/2017 | Vale et al. |
| 2017/0112513 | A1 | 4/2017 | Marchand et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |
| 2017/0348014 | A1 | 12/2017 | Wallace et al. |
| 2018/0042624 | A1 | 2/2018 | Greenhalgh et al. |
| 2018/0042626 | A1 | 2/2018 | Greenhalgh et al. |
| 2018/0070968 | A1 | 3/2018 | Wallace et al. |
| 2019/0117244 | A1 | 4/2019 | Wallace et al. |
| 2019/0133622 | A1 | 5/2019 | Wallace et al. |
| 2019/0133623 | A1 | 5/2019 | Wallace et al. |
| 2019/0133624 | A1 | 5/2019 | Wallace et al. |
| 2019/0133625 | A1 | 5/2019 | Wallace et al. |
| 2019/0133626 | A1 | 5/2019 | Wallace et al. |
| 2019/0133627 | A1 | 5/2019 | Wallace et al. |
| 2019/0336148 | A1 | 11/2019 | Greenhalgh et al. |

FOREIGN PATENT DOCUMENTS

| | | |
|---|---|---|
| GB | 2498349 | 7/2013 |
| WO | WO 00/32118 | 6/2000 |
| WO | WO 2009086482 | 7/2009 |
| WO | WO 2012009675 | 1/2012 |
| WO | WO 2012049652 | 4/2012 |
| WO | WO 2012162437 | 11/2012 |
| WO | WO 2017058280 | 4/2017 |
| WO | WO2017189535 | 11/2017 |
| WO | WO 2017189550 | 11/2017 |
| WO | WO2017189591 | 11/2017 |
| WO | WO2017189615 | 11/2017 |
| WO | WO2017210487 | 12/2017 |
| WO | WO 2018049317 | 3/2018 |
| WO | WO 2019010318 | 1/2019 |
| WO | WO 2019094456 | 5/2019 |
| WO | WO 2019222117 | 11/2019 |

OTHER PUBLICATIONS

PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, mailed Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Extended European Search Report dated Oct. 5, 2018 for European patent appln No. 18174891.4.
Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
PCT Invitation to Pay Additional Fees for International Appln. No. PCT/US2017/029345, Applicant Stryker Corporation, dated Oct. 17, 2017.
International search report and written opinion dated Feb. 28, 2018 for PCT/US2017/029345, Applicant Stryker Corporation.
Non Final Office Action dated Aug. 23, 2019 for U.S. Appl. No. 15/700,685.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Response to Non Final Office Action filed Nov. 8 2019 for U.S. Appl. No. 15/700,685.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Notice of Allowance dated Nov. 21, 2019 for U.S. Appl. No. 15/700,685.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.

(56) References Cited

OTHER PUBLICATIONS

European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule 161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Restriction Requirement filed Jul. 25, 2019 for U.S. Appl. No. 15/700,685.
Response to Ex Parte Quayle office action filed Jul. 25, 2019 for U.S. Appl. No. 15/497,092.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Amendment Response submitted on Dec. 3, 2019 for U.S. Appl. No. 15/794,939.
PCT International Search Report and Written Opinion for International Patent Appln. No. PCT/US2019/050467, Applicant Stryker Corporation, dated Dec. 18, 2019 (17 pages).
Non Final Office Action dated Dec. 27, 2019 for U.S. Appl. No. 16/594,256.
Final Office Action dated Mar. 2, 2020 for U.S. Appl. No. 15/794,939.
Notice of Allowance for U.S. Appl. No. 15/794,939 dated Mar. 31, 2020.
Amendment Response submitted on Mar. 27, 2020 for U.S. Appl. No. 16/594,256.
Non-Final Office Action for U.S. Appl. No. 16/183,162 dated May 13, 2020.
Non-Final Office Action for U.S. Appl. No. 16/169,334 dated May 8, 2020.
Non-Final Office Action for U.S. Appl. No. 16/183,171 dated May 13, 2020.
Foreign OA for Japanese Patent Application No. 2018-535810 dated Feb. 7, 2020.
Extended European Search Report for EP Patent Appl. No. 20185092.2 dated Sep. 11, 2020.
EP Examination Report for EP Patent Appl. No. 18745794.0 dated Jul. 20, 2020.
Amendment Response to Non-Final Office Action for U.S. Appl. No. 16/183,171 dated Jul. 30, 2020.
Amendment Response to Non-Final Office Action for U.S. Appl. No. 16/183,162 dated Jul. 30, 2020.
Applicant Interview Summary for U.S. Appl. No. 16/096,031 dated Jul. 30, 2020.
Applicant Interview Summary for U.S. Appl. No. 16/183,133 dated Aug. 24, 2020.
Non-Final Office Action for U.S. Appl. No. 16/183,149 dated Aug. 18, 2020.
Amendment Response to NFOA for U.S. Appl. No. 16/183,149 dated Sep. 25, 2020.

* cited by examiner

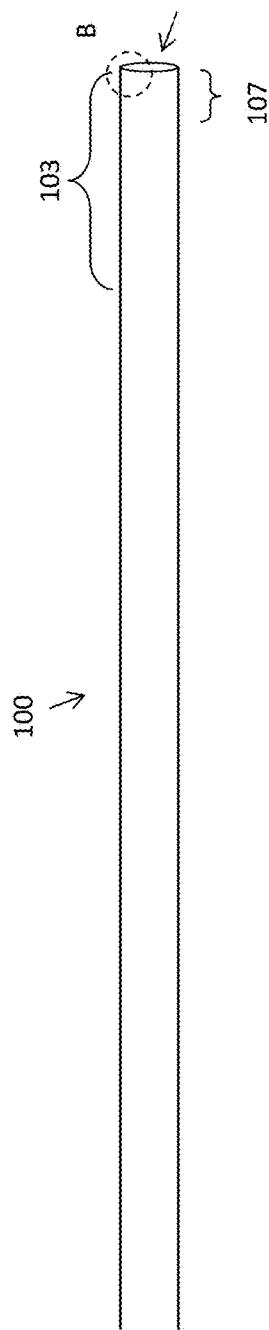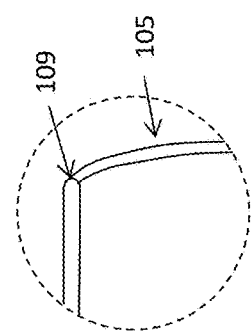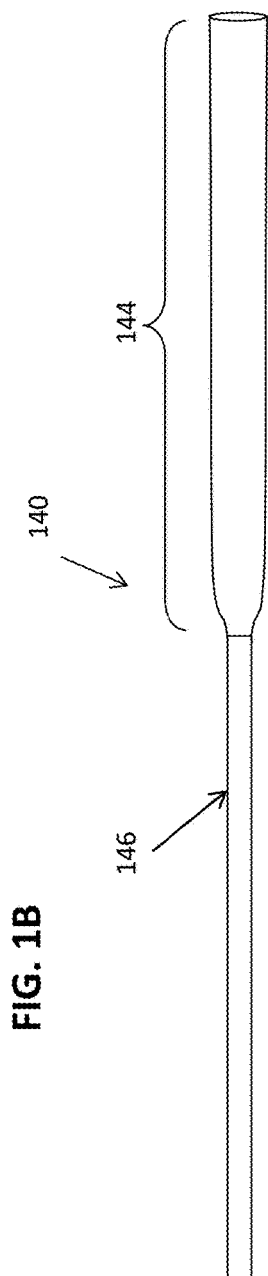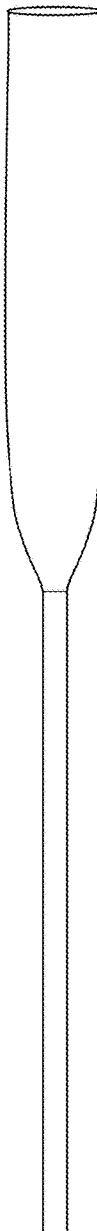
FIG. 1A
FIG. 1B
FIG. 1C
FIG. 1D

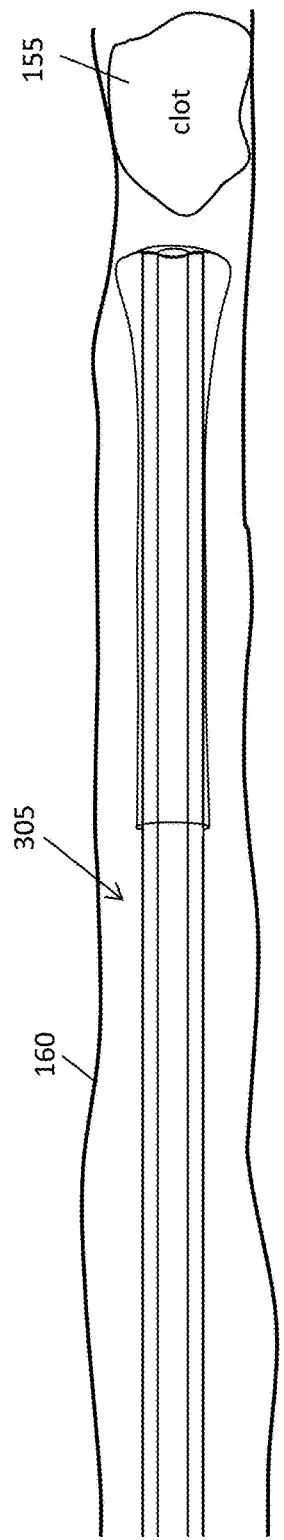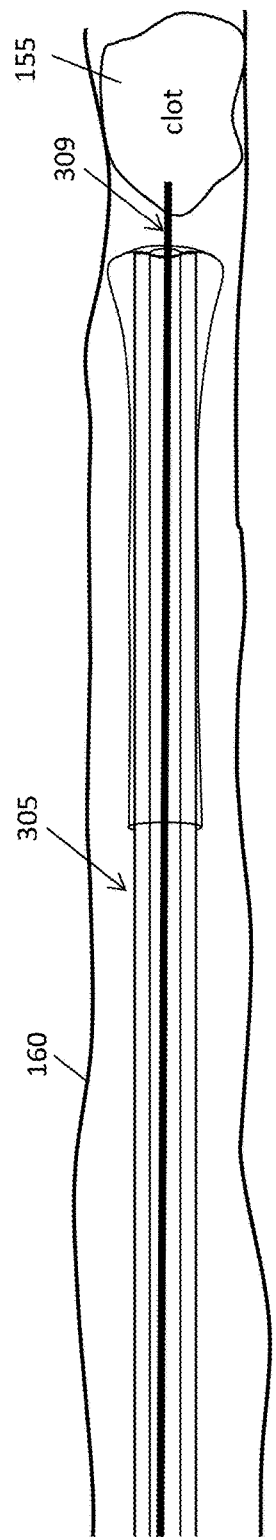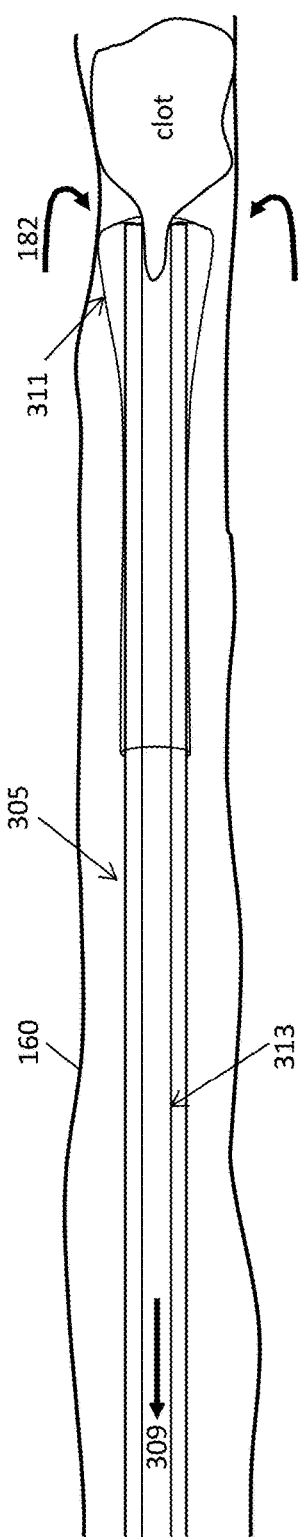

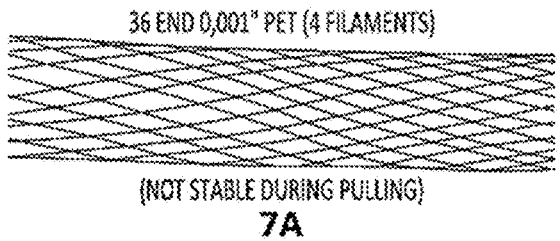
36 END 0.001" PET (4 FILAMENTS)
(NOT STABLE DURING PULLING)
7A
72 END 0.001" PET (4 FILAMENTS)
7B
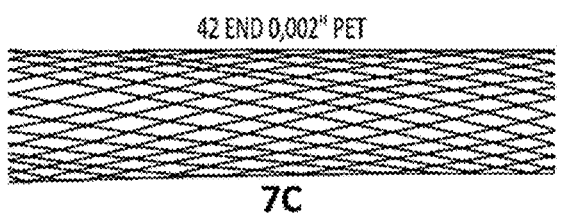
42 END 0.002" PET
7C
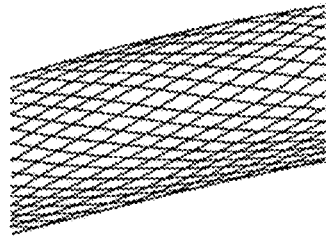
72 END 0.001" NITI
(ON MANDREL PRE HEAT TREATING)
7D
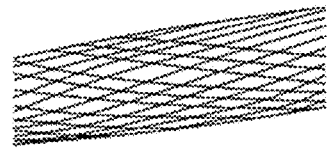
72 END 0.001" NITI
(POST HEAT TREAT & CONSTRAINED IN 0.071")
7E
FIGS. 7A-7E
PULLING CLOT IN: VESSEL ID ~ SAME AS CATHETER TIP
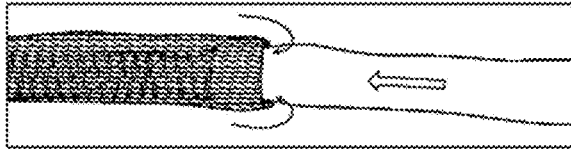
8A
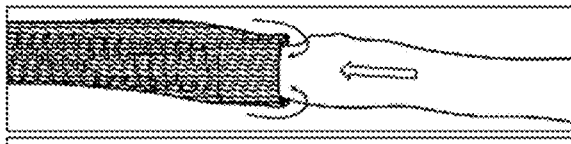
8B
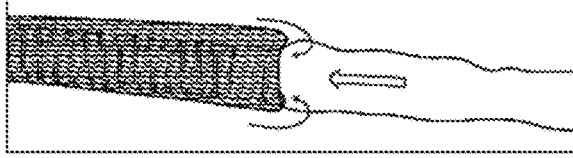
8C
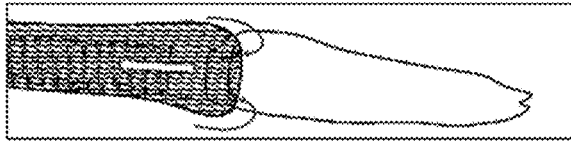
8D
BRAID IN REVERSE: EJECTING CLOT
(DIFFERENT PIECE OF CLOT)
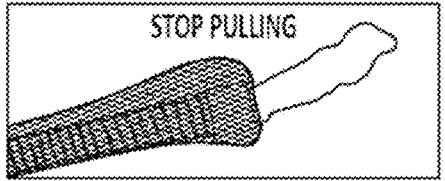
STOP PULLING
8E
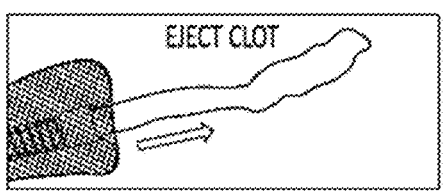
EJECT CLOT
8F
FIGS. 8A-8F

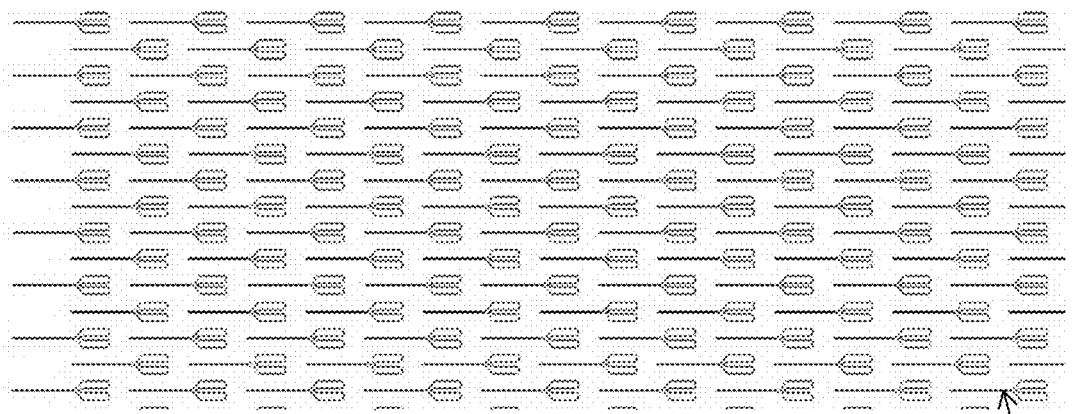
FIG. 21A
FIG. 21B
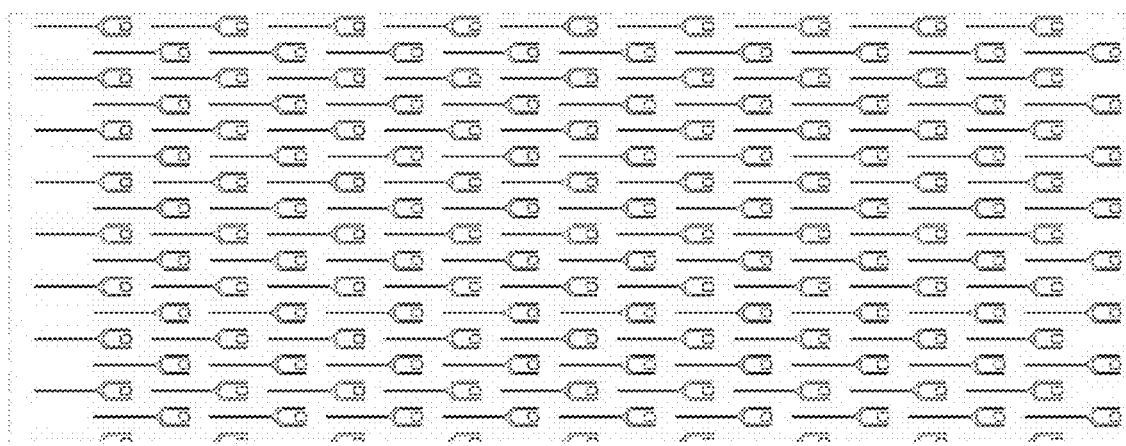
FIG. 22A
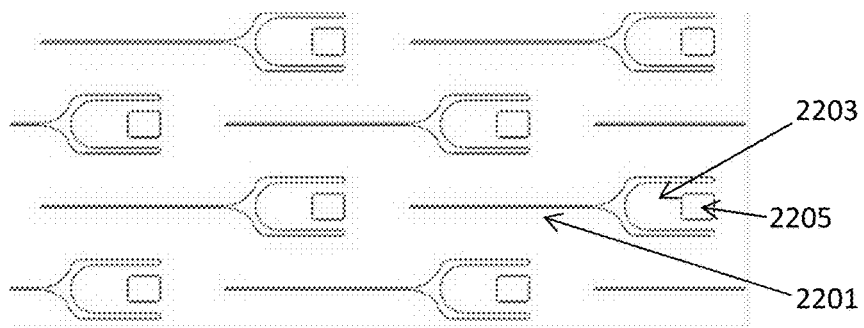
FIG. 22B

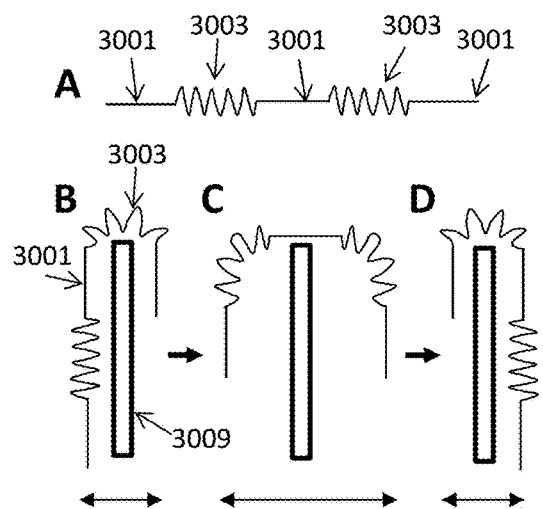 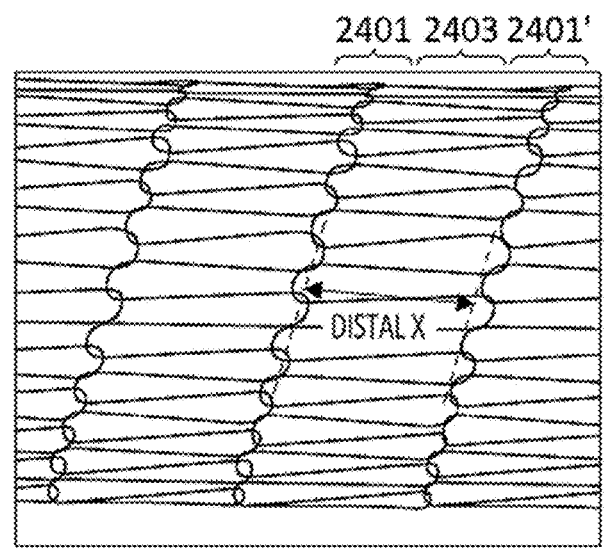
FIGS. 30A-30D                    FIG. 31A
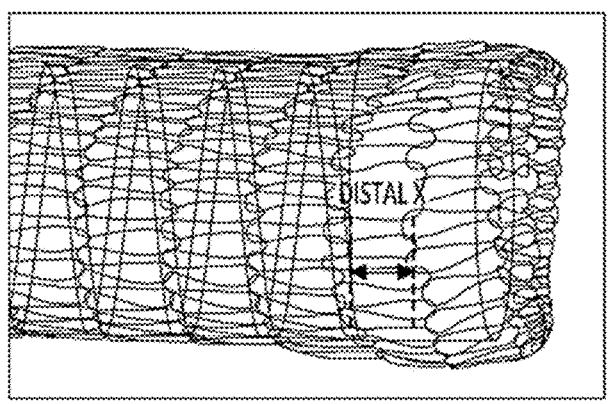 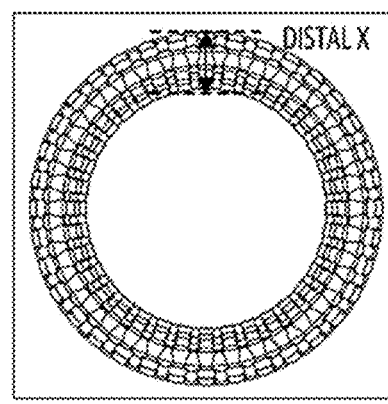
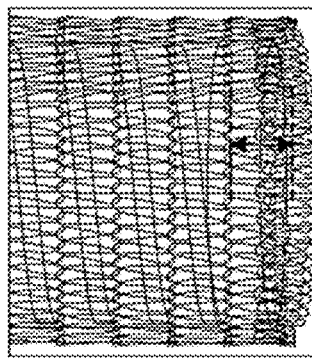 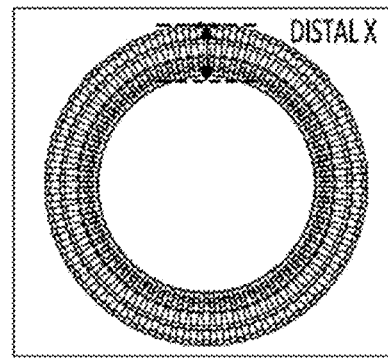
FIGS. 31B-31E

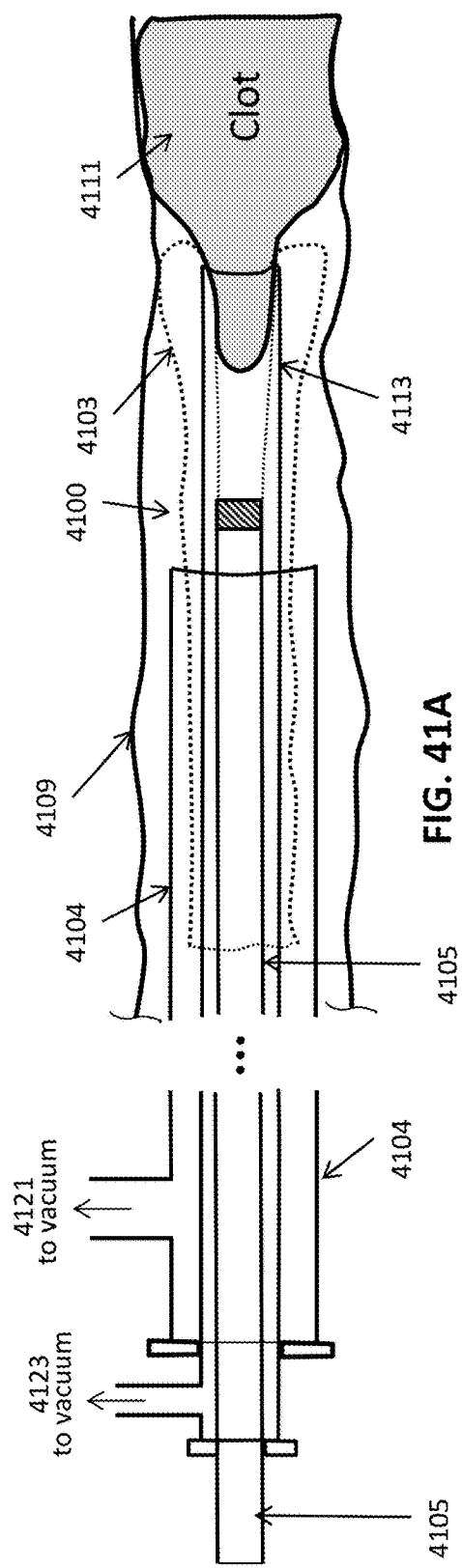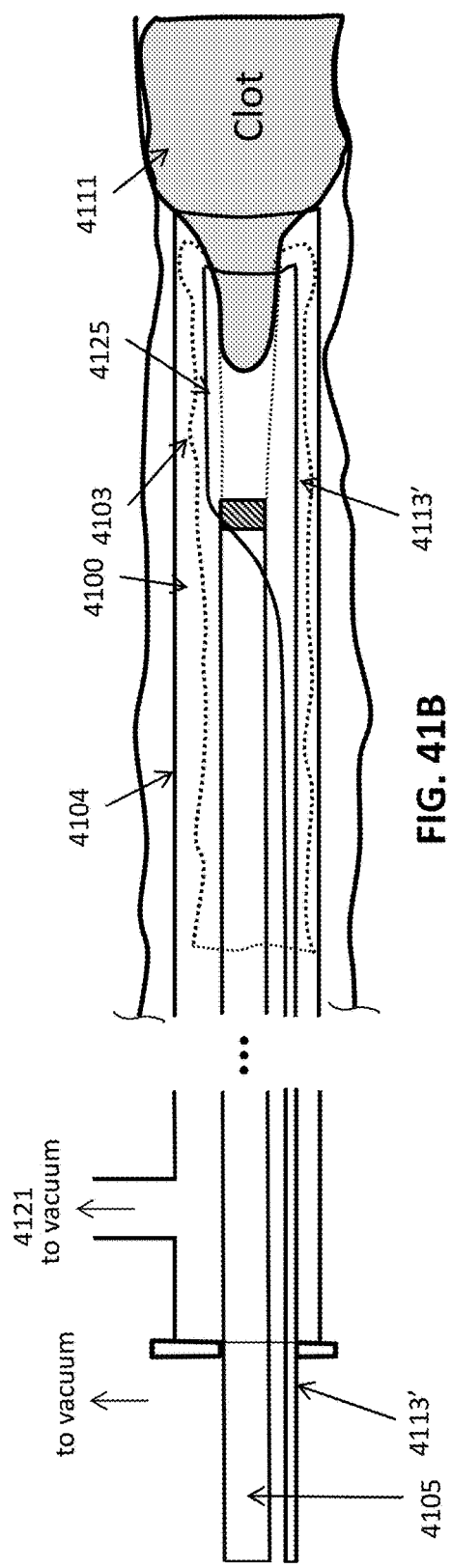

ANTI-JAMMING AND MACERATING THROMBECTOMY APPARATUSES AND METHODS

CROSS REFERENCE TO RELATED APPLICATIONS

The present application is a continuation of international patent application no. PCT/US2017/029345, having an international filing date of Apr. 25, 2017, which claims priority to U.S. provisional patent application No. 62/327,024, filed on Apr. 25, 2016 and titled "DOZER THROMBECTOMY SYSTEM," 62/345,152, filed on Jun. 3, 2016 and titled "DOZER THROMBECTOMY SYSTEM 2," and 62/393,460, filed on Sep. 12, 2016, and titled "DOZER II THROMBECTOMY SYSTEM PROV."

This patent application may be related to U.S. patent application Ser. No. 15/291,015, filed on Oct. 11, 2016, titled "MECHANICAL THROMBECTOMY APPARATUSES AND METHODS", which is a continuation of U.S. patent application Ser. No. 15/043,996, filed Feb. 15, 2016, now U.S. Pat. No. 9,463,035, which claims priority to each of the following provisional patent applications: U.S. Provisional Patent Application No. 62/284,300, filed Sep. 28, 2015; U.S. Provisional Patent Application No. 62/284,752, filed Oct. 8, 2015; and U.S. Provisional Patent Application No. 62/245,560, filed Oct. 23, 2015.

Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

It is often desirable to remove tissue from the body in a minimally invasive manner as possible, so as not to damage other tissues. For example, removal of tissue from within a vasculature, such as blood clots, may improve patient conditions and quality of life.

Many vascular system problems stem from insufficient blood flow through blood vessels. One causes of insufficient or irregular blood flow is a blockage within a blood vessel referred to as a blood clot, or thrombus. Thrombi can occur for many reasons, including after a trauma such as surgery, or due to other causes. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If one of the coronary arteries is 100% thrombosed, the flow of blood is stopped in that artery, resulting in a shortage of oxygen carrying red blood cells, e.g., to supply the muscle (myocardium) of the heart wall. Such a thrombosis is unnecessary to prevent loss of blood but can be undesirably triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to vital nerve centers in the cranium. Oxygen deficiency reduces or prohibits muscular activity, can cause chest pain (angina pectoris), and can lead to death of myocardium which permanently disables the heart to some extent. If the myocardial cell death is extensive, the heart will be unable to pump sufficient blood to supply the body's life sustaining needs. The extent of ischemia is affected by many factors, including the existence of collateral blood vessels and flow which can provide the necessary oxygen.

Clinical data indicates that clot removal may be beneficial or even necessary to improve outcomes. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are apparatuses (devices, systems and kit) and methods of using them that may address the needs and problems discussed above.

SUMMARY OF THE DISCLOSURE

Described herein are mechanical thrombectomy apparatuses (devices, systems, etc.) and methods of using and making them. These apparatuses may be configured to prevent or reduce jamming and enhance grabbing and/or macerating a thrombus, e.g., clot, being removed. Typically, the mechanical thrombectomy apparatuses described herein are inverting tractor thrombectomy apparatuses that includes a tractor (e.g., tractor region, tractor portion, etc.) comprising a flexible tube of material that inverts over itself as it rolls over a distal end opening of an elongate inversion support. The elongate inversion support typically comprises a catheter having a distal end opening into which the tractor inverts. The flexible tractor inverts and rolls back into itself and may be drawn into the elongate inversion support in a conveyor-like motion; the outward-facing region rolls around to become an inward-facing region, e.g., within the lumen of the elongate inversion support. The rolling motion may thus draw a clot or other object within a vessel into the elongate inversion support.

Implementation of a rolling tractor that is sufficiently flexible to easily roll at the distal end (e.g., over a catheter) but sufficiently stiff to prevent jamming at the distal end of the elongate inversion support has proven challenging.

The elongate inversion support portion of the apparatus described herein may be or may include (particularly at its distal end) any appropriate catheter, e.g., a flexible tube that can be inserted into a body vessel (e.g., blood vessel) into which the more flexible tractor portion can be withdrawn by pulling against the elongate inversion support. The elongate inversion support may, in some variations, also be referred to as outer catheters (e.g., when the puller for the tractor is referred to as an inner catheter) and/or inversion catheters and/or support catheter, as it may support the inversion of the tractor. The elongate inversion support, including a catheter forming the elongate inversion support, may include a braided or woven portion, a spiral or coiled portion, etc. (e.g., having a braided shaft), may have a single layer or multiple layers, and may be formed of biocompatible materials, including polymers, metals, etc. (e.g., PTFE). Examples of vascular catheters that may form the elongate inversion support include micro catheters.

The mechanical thrombectomy apparatuses described herein include a tractor region and/or elongate inversion support that are configured to prevent jamming, while still able to efficiently "grab" a clot from within a vessel. For example, described herein are mechanical thrombectomy apparatuses that may be configured to grab or grasp and/or macerate a clot as it is mechanically drawn into the apparatus for removal. Although suction may be used in addition to the mechanical grabbing of the clot, in some variations suction is not used.

The tractor regions described herein may include projections that extend from the tractor region, particularly or exclusively as it bends around during inverting (e.g., at the distal end of the device). These projections may remain flat or non-extending when the tractor is held in parallel with the elongate inversion support. Alternatively, the projections may extend at all times. In general, the tractor may be formed of a woven materials, knitted material, or laser-cut sheet of material. The knitted and/or woven materials may be fibrous materials (including natural fibers, synthetics fibers, etc.), polymeric materials, or the like. For example, the material (e.g., strands) forming the woven or knitted material may be one or more of: monofilament polymer, multifilament polymer, NiTi filament, NiTi tube with radiopaque metallic center, Cobalt chromium alloy filament, Cobalt chromium alloy tube with radiopaque metallic center, Nylon, Polyester, Polyethylene terephthalate, and Polypropylene. The sheets of material (e.g. a solid sheet of material) formed into the tractor region may be one or more of: polymeric material (e.g., PTFE), silicone materials, polyurethanes, shape memory alloys, stainless steels, etc. The sheets may be extruded, glued, or the like. The sheets may be cut to form pores and/or projections. For example, the sheets may include one or more laser-cut proj ections. Any of these apparatuses may be coated with a hydrophilic and/or hydrophobic coating, and/or may include pores. The tractor may have a porosity of greater than >60% (greater than 70%, greater than 75%, greater than 80%, greater than 85%, etc., between 60-95, 65-95, 70-95%, etc.).

For example, described herein are clot-grabbing mechanical thrombectomy apparatuses that include a tractor region. The tractor region may include a plurality of clot-grabbing projections extending from one face of the tractor. In some variations, the clot-grabbing projections may be configured so that they move to extend (e.g., out of the plane of the tractor) when the tractor region bends around, e.g., around the distal end of the catheter of the elongate inversion support, to invert.

In general, a mechanical thrombectomy apparatus for removing a clot from a vessel may include: a elongate inversion support comprising a catheter having a distal end and a distal end opening; a tractor comprising a flexible tube extending longitudinally within the catheter and doubling back over the distal end of the catheter to extend along the distal end of the catheter, an inner puller coupled to a distal end of the tractor; and a guidewire lumen extending through the catheter, tractor and the inner puller and configured to pass a guidewire. The proximal end of the tractor may be loose (e.g., may be free to slide over the catheter. The tractor may also be configured so that is it biased to hold itself against outer diameter of the catheter, and simultaneously biased to expand when inverted within the catheter; in this configuration, the inverting distal-facing end of the tractor may be flared outward slightly so that the diameter of the tractor expands slightly near the distal-facing inverting end of the apparatus. This configuration may also maintain the portion of the tractor within the catheter so that it is close to the inner diameter of the catheter; e.g., the inner diameter of the portion of the tractor within the catheter may be greater than 50% of the inner diameter of the catheter, greater than 55% of the inner diameter of the catheter, greater than 60% of the inner diameter of the catheter, greater than 65% of the inner diameter of the catheter, greater than 70% of the inner diameter of the catheter, greater than 75% of the inner diameter of the catheter, etc.

For example, a mechanical thrombectomy apparatus for removing a clot from a vessel may include: an elongate inversion support comprising a catheter having a distal end and a distal end opening; a tractor comprising a flexible tube that extends distally in a first configuration within the catheter, inverts over the distal end opening of the catheter and extends proximally in a second configuration (that is inverted relative to the first configuration) along the distal end of the catheter, wherein the tractor comprises a tubular wall, further wherein the tractor is configured to invert by rolling over the distal end opening of the catheter when a first end of the tractor is pulled proximally within the catheter; and a plurality of projections that extend from a portion of the tractor that is inverted over the distal end opening of the catheter as the tractor rolls over the distal end opening of the catheter, wherein the plurality of projections do not extend from the tractor as it extends proximally in the inverted configuration along the distal end of the catheter.

As mentioned, in general, the mechanical thrombectomy apparatuses described herein may include a clot-grabbing projection. For example, a mechanical thrombectomy apparatus for removing a clot from a vessel may include: an elongate inversion support comprising a catheter having a distal end and a distal end opening; a tractor comprising a flexible tube extending within the catheter and doubling back over the distal end of the catheter to extend along the distal end of the catheter, the flexible tube comprising a tube wall, wherein the tractor is configured to invert over the distal end opening when a first end of the tractor is pulled proximally within the catheter, further wherein the tractor comprises a plurality of projections configured so that the plurality of projections extend out of a plane of the tube wall as the tube wall inverts over the distal end opening, further wherein the plurality of projections remain in the plane of the tube wall as the tube wall extends along the distal end of the catheter; and a guidewire lumen extending through the catheter and the tractor and configured to pass a guidewire.

In particular, the tractor may be a tube of woven ribbons, further wherein the plurality of projections is formed from edges of the ribbons. The ribbons may comprise flattened strips or strands of material having at least one (through typically four) elongate edges. For example, the ribbons may have a rectangular cross-section. In some variations the ribbons may have square or triangular or other cross-sections having one or more edges. Ribbons having edges may be woven, e.g., so that they are arranged in a helical pattern as they extend over the distal end of the elongate inversion support. Thus, the edge(s) of the ribbon may extend outward, out of the plane of the tractor, when the tractor inverts. These extending edges may bend up, forming scooping, cutting and/or grabbing projections over the bending region of the tractor. The ribbons may be formed of any appropriate material, including those discussed above, such as a metallic or polymeric material.

The projections from the tractor regions described herein may be formed by cut-out regions in the tractor material. For example, a sheet or tube of material may be used to form the tractor, such as a tube of steel (e.g., stainless steel), polyester, nylon, expanded Polytetrafluoroethylene (ePTFE), Nitinol, or a fabric, and projections may be formed, e.g., by cutting, from the tube or sheet. For example, the projections may be cut from the tube wall. In some variations the projections may be cut in addition to openings, slits, slots, or gaps (e.g., forming pores). For example, a tractor may have at least one porous section having a pore pattern having a longitudinal separation between pores of less than about 0.005 inches in width. In some variations, the projections may be cut from the tube wall at an angle of less than 90° tangent to the tube wall. For example, each of the plurality of projections may have a width in a direction transverse to the flexible tube and a length in a direction along a long axis of the flexible tube; the ratio of length to width may be between, e.g., 2 and 100 (e.g., 5 and 100, 10 and 100, 5 and 90, 5 and 80, 5 and 70, 5 and 50, 10 and 90, 10 and 80, 10 and 70, 10 and 60, etc.).

The projections may be shaped to grab and/or macerate the clot. For example, all or some of the plurality of projections may have one or more of: a paddle shape, a scoop shape, and spike shape. The projections may extend proud of the plane of the tractor (e.g., at 90° or perpendicular to the tractor surface from which the projection extends, or between about 45-135° from the plane of the tractor surface, etc.). The projections may be sharp (e.g., may have sharp ends). The projections may extend between 0.01 mm to 5 mm from the tractor surface (e.g., between 0.01 mm and 2 mm, between 0.05 mm and 1 mm, etc.). The size of the projections may be scaled to the size of the tractor and/or the size of the vessel into which the apparatus is intended to be inserted into.

In any of the apparatuses described herein, the elongate inversion support (e.g., catheter) may be adapted to enhance rolling of the tractor region (inverting) over the distal end. For example, in any of the apparatuses described herein, the catheter may be configured so that the material hardness of the catheter decreases over the distal end of the catheter until the distal end opening, wherein the distal end opening has a material hardness that is greater than a material hardness of a region immediately proximal to the distal end, further wherein the distal end opening has a rounded lip profile. The catheter distal end may be stiffer because it is thicker (e.g., it may be formed by inverting the distal end of the catheter back over itself, and/or it may be formed of a stiffer material than the adjacent more proximal region (including by including a reinforcing material).

The projections configured to help grab clot may be distributed over the entire length of the tractor, or only over a region of the tractor (e.g., the distal end region, e.g., the distal 5 mm, 7 mm, 10 mm, 15 mm, 20 mm, etc. or less). In some variations, the distribution of projections may be non-uniform distributed, e.g., the tractor may include a non-uniform density of projections along the length of the tractor. The projections may be oriented relative to the tractor so that the projections extend in the distal direction when the tractor is on the outer diameter of the catheter, which may help them grab clot.

The projections may be configured (e.g., by laser cutting the tube forming the tractor) as a plurality of slots or openings through the tractor.

In any of the apparatuses described herein, the tractor may include one or more coatings from the group of: a lubricious coating, a metal coating, a heparin coating, an adhesive coating, and a drug coating. In particular the tractor may include a uniform or non-uniform lubricious (e.g., hydrophilic) coating. Such coatings may assist in making the tractor slide more easily to invert (e.g., over the distal end of the catheter), but may make it particularly hard to grab clot. The projections described herein may address this issue.

Any of the apparatuses described herein may include a releasable attachment between the tractor and an outer surface of the elongate inversion support (e.g., catheter), configured to release when the tractor is pulled with a force that is greater than a predetermined force threshold. This may prevent premature deployment of the apparatus. The releasable attachment may be a breakable (e.g., frangible) region, e.g., of an adhesive, etc. or a releasable tie, etc. The releasable attachment may be formed by regions of different hydrophobicity/hydrophilicity. Any of these apparatuses may be configured so that the force required to deploy the apparatus is greater than a predetermined threshold, e.g., the releasable force threshold may be greater than 50 g, 100 g, 200 g, 300 g, 400 g, 500 g, 600 g, 700 g, 800 g, 900 g, 1000 g, etc. of force (e.g., greater than 200 g of force). In addition, any of these apparatuses may include a cover, an outer elongate inversion support comprising a catheter, sleeve, sheath, etc., holding the proximal end of the tractor against the catheter until it is ready to be deployed. Deployment may mean releasing the end (e.g., the end on the outer surface of the catheter) from a releasable attachment; once deployed, the force required to pull the tractor proximally in the catheter, including drawing the tractor from along the outer diameter of the catheter, inverting the tractor and pulling the tractor into the catheter distal end opening (without a clot or other material in the tractor) may be substantially less than the initial deployment force. For example, the force required to pull the tractor into the catheter proximally may be 1 gram (g) of force or less (or 2 g, 3 g, 4 g, 5 g, 6 g, 7 g, 8 g, 9 g, 10 g, 20 g, 30 g, 40 g, 50 g, etc., of force or less). Alternatively or additionally, any of these apparatuses may include a material between the tractor and the catheter (e.g., a sleeve, coating, etc.) to reduce the amount of force required to invert the catheter over the distal end of the catheter, and/or to prevent jamming of the tractor in the catheter.

As mentioned, any of these apparatuses may include a puller, e.g., an elongate puller coupled to a distal end of the tractor. Any of these apparatuses may include an elongate puller within the catheter coupled to a distal end of the tractor. The elongate puller may comprise a hypotube having an inner lumen that is continuous with the guidewire lumen though the flexible tube.

In general, the tractor may be any appropriate length. For example, the tractor may be between 3 to 100 cm long (e.g., between 3 and 50 cm, between 3 and 40 cm, between 3 and 30 cm, between 3 and 20 cm, between 10 and 100 cm, between 10 and 50 cm, between 20 and 100 cm, between 20 and 50 cm, etc.).

In any of these apparatuses, the apparatus may be configured so that the tractor may be retracted into the catheter by applying less than 300 grams of force (e.g., less than 400 g of force, less than 300 g of force, less than 200 g of force, less than 100 g of force, less than 90 g of force, less 80 g of force, less than 70 g of force, less than 60 g of force, less than 50 g of force, less than 10 g of force, etc.) to a distal end of the flexible tube. For example, as mentioned above, the apparatus may include a hydrophilic coating, a lubricant on the catheter and/or tractor, a sleeve between the tractor and catheter, etc. This force required to retract the tractor into the catheter typically refers to the force required to roll the tractor over the distal end of the tractor; an initial deployment force (e.g., to release the end of the tractor outside of the catheter) may be greater than the force required to retract the catheter (e.g., greater than 100 g of force, 200 g of force, 300 g of force, 400 g of force, 500 g of force, 600 g of force, 700 g of force, 800 g of force, 900 g of force, 1000 g of force, 1500 g of force, 2000 g of force, etc.).

For example, a mechanical thrombectomy apparatus for removing a clot from a vessel may include: an elongate inversion support comprising a catheter having a distal end and a distal end opening; a tractor comprising a flexible tube that extends distally in a first (e.g., "un-inverted") configuration within the catheter, inverts over the distal end opening of the catheter into a second configuration (that is inverted relative to the first configuration) and extends proximally in an inverted configuration along the distal end of the catheter, the flexible tube comprising a plurality of ribbons having a square or rectangular cross-section woven together, wherein the tractor is configured to invert by rolling over the distal end opening of the catheter when a first end of the tractor is pulled proximally within the catheter, wherein a plurality of edges of the plurality of ribbons extend from a portion of the tractor that is inverted over the distal end opening of the catheter as the tractor rolls over the distal end opening of the catheter, further wherein the projecting edges are not extended from the tractor in a portion of the tractor that extends over the distal end of the catheter; and a guidewire lumen extending through the catheter and the tractor and configured to pass a guidewire.

A mechanical thrombectomy apparatus for removing a clot from a vessel may include: an elongate inversion support comprising an elongate inversion support comprising a catheter having a distal end and a distal end opening; a tractor comprising a flexible tube extending within the catheter and doubling back over the distal end of the catheter to extend along the distal end of the catheter, the flexible tube comprising a tube wall formed from a plurality of woven ribbons having a square or rectangular cross-section, wherein the tractor is configured to invert over the distal end opening when a first end of the tractor is pulled proximally within the catheter, further wherein the tractor comprises a plurality of projections configured so that the plurality of projections extend out of a plane of the tube wall as the tube wall inverts over the distal end opening, further wherein the plurality of projections are formed from edges of the ribbons and the projections remain in the plane of the tube wall as the tube wall extends along the distal end of the catheter; and a guidewire lumen extending through the catheter and the tractor and configured to pass a guidewire.

A mechanical thrombectomy apparatus for removing a clot from a vessel may include: an elongate inversion support comprising a catheter having a distal end and a distal end opening; a tractor comprising a flexible tube extending within the catheter and doubling back over the distal end of the catheter, the flexible tube comprising a tube wall, wherein the tractor is configured to invert over the distal end opening when a first end of the tractor is pulled proximally within the catheter, further wherein the tractor comprises a plurality of projections formed in the tube wall and configured so that the plurality of projections extend proud of the tractor when the tractor inverts over the distal end opening and otherwise remain in a plane of the tube wall; wherein each of the plurality of projections have a width in a direction transverse to the flexible tube and a length in a direction along a long axis of the flexible tube, further wherein the ratio of length to width is between 10 and 100; and a guidewire lumen through the catheter and the tractor configured to pass a guidewire.

Any of the apparatuses described herein may be configured so that the tractor is highly soft, and therefore rolls around the distal end of the catheter forming the elongate inversion support easily without jamming and/or requiring a large force to roll the tractor over the distal end opening of the catheter. In particular, tractors having a low axial compression strength, that would, but for the elongate inversion support, typically buckle, have been found to prevent jamming of the elongate inversion support as the tractor inverts. In particular, unsupported tractors (e.g., tractor that are not rolling over a catheter supported annular opening) that are configured to collapse radially under an axial compression of less than about 500 g of force (e.g., less than: about 500 g force, about 400 g force, about 300 g force, about 200 g force, about 150 g force, about 100 g force, about 50 g force, etc.) may be particularly helpful in preventing jamming. For most knitted, woven, and braided tractors, including those described herein, when the tractor is configured to withstand greater that this amount of axial compression force, the tractor may jam, and/or may require excessive force to invert. Thus, in any of the apparatuses and methods described herein, the tractor maybe sufficiently soft such that without support from the catheter, the tractor collapses radially under an axial compression of less than 200 g of force when inverting (and may instead buckle).

Further, in any of the apparatuses described herein, the tractor may be biased to expand to greater than the outer diameter of the catheter in a second configuration (that is inverted relative to the first configuration) where the tractor is extending over the outer diameter of the catheter. The same tractor may be biased to expand to greater than the inner diameter of the catheter of the elongate inversion support in the first (e.g., un-inverted), configuration where the tractor is within the catheter of the elongate inversion support. Thus, in relaxed configuration, prior to assembling with the elongate inversion support, the tractor may be oversized compared to the catheter of the elongate inversion support; the portion of the tractor that extends within the catheter of the elongate inversion support, referred to as "un-inverted," may have an inner diameter that is greater than the inner diameter of the catheter, which may tend to drive the tractor toward the walls of the inner diameter of the catheter without collapsing down into the catheter. Further, the inner diameter of the tractor in the "inverted" configuration, e.g., the configuration of the portion that is doubled back over and along the catheter of the elongate inversion support, may be greater than the outer diameter of the catheter of the elongate inversion support. This arrangement may prevent jamming and an increased resistance between the tractor and the outside of the catheter of the elongate inversion support. The catheter may be biased to expand in both the inverted and un-inverted configurations by, e.g., heat setting. The tractor may be inverted to transition between the first and second configurations by rolling over the distal end of the catheter; the terms "inverted" and "un-inverted" are therefore relative terms.

Also described herein are methods of removing a clot using a mechanical thrombectomy apparatus. For example, a method of removing a clot using a mechanical thrombectomy apparatus may include: positioning a distal end of the mechanical thrombectomy apparatus adjacent to a clot within a vessel, wherein the mechanical thrombectomy apparatus includes a tractor region that extends along a distal region of an elongate inversion support having a catheter and inverts over a distal end of the catheter so that a distal end of the tractor extends proximally within the catheter; pulling the distal end of the tractor proximally within the catheter to invert the tractor over the distal end of the catheter to extend a plurality of projections from the tractor and grab the clot; and drawing the clot into the catheter.

Any of these methods may include macerating the clot with the plurality of projections.

For example, a method of removing a clot using a mechanical thrombectomy apparatus may include: positioning a distal end of the mechanical thrombectomy apparatus adjacent to a clot within a vessel, wherein the mechanical thrombectomy apparatus includes a tractor region that extends along a distal region of a catheter and inverts over a distal end of the catheter so that a first end of the tractor extends proximally within the catheter; pulling the first end of the tractor proximally within the catheter to roll the tractor over the distal end of the catheter so that the tractor inverts over the distal end of the catheter and extends a plurality of projections from the tractor; grabbing the clot with the plurality of projections; and drawing the clot into the catheter.

As mentioned above, the tractor may comprises a plurality of woven ribbons having a square or rectangular cross-section, further wherein pulling the distal end of the tractor proximally within the catheter to invert the tractor over the distal end of the catheter to extend a plurality of projections from the tractor comprises extending a plurality of edges of the woven ribbons from out of a plane of the tractor as the tractor is inverted over the distal end of the catheter to grab the clot with the extended edges.

Alternatively or additionally, the tractor may comprise a plurality of cut-out regions formed in the tractor, further wherein pulling the distal end of the tractor proximally within the catheter to invert the tractor over the distal end of the catheter extends the cut-out regions forming the plurality of projections from the tractor to grab the clot. Any of these methods may include sliding a loose proximal end of the tractor over the catheter as the distal end of the tractor is pulled proximally.

Any of these methods may include using a guidewire. For example, positioning the distal end of the mechanical thrombectomy apparatus may comprise sliding the mechanical thrombectomy apparatus over a guidewire.

Similarly, any of these methods may include releasing a releasable attachment between the tractor and an outer surface of the catheter.

Pulling the distal end of the tractor proximally may comprises maintaining an inner diameter of the tractor within the catheter at greater than 60% of an inner diameter of the catheter to prevent the tractor from locking over the distal end of the catheter.

Also described herein are apparatuses having tractor regions with variable stiffness along the length of the tractor. These apparatuses may invert (roll) at their distal-facing end of the tractor with a ratcheting motion. These apparatuses, and methods of using them, may provide a movement that prevents jamming, and may also help grab clot.

For example, described herein are mechanical thrombectomy apparatuses for removing a clot from a vessel that may include: a catheter having a distal end and a distal end opening; a tractor comprising a flexible tube extending longitudinally within the catheter and doubling back over the distal end of the catheter to extend along the distal end of the catheter, wherein the flexible tube comprises longitudinally alternating regions of higher and lower stiffness, wherein the regions of higher stiffness have a stiffness that is greater than the regions of lower stiffness; an inner puller coupled to a distal end of the tractor; and a guidewire lumen extending through the catheter, tractor and the inner puller and configured to pass a guidewire.

A mechanical thrombectomy apparatus for removing a clot from a vessel may include: a catheter having a distal end and a distal end opening; a tractor comprising a flexible tube extending longitudinally within the catheter and doubling back over the distal end of the catheter to extend along the distal end of the catheter, wherein the flexible tube comprises longitudinally alternating regions of higher and lower stiffness, wherein the regions of higher stiffness have a stiffness that is greater than the regions of lower stiffness, further wherein a diameter of the distal-facing end of the tractor oscillates as the tractor is pulled proximally within the catheter to invert the tractor over the distal end of the catheter; an inner puller coupled to a distal end of the tractor; and a guidewire lumen extending through the catheter, tractor and the inner puller and configured to pass a guidewire.

A mechanical thrombectomy apparatus for removing a clot from a vessel may include: a catheter having a distal end and a distal end opening having a radius; a tractor comprising a flexible tube extending longitudinally within the catheter and doubling back over the distal end of the catheter to extend along the distal end of the catheter, wherein the flexible tube comprises longitudinally alternating regions of higher and lower stiffness helically arranged around the flexible tube, wherein the regions of higher stiffness have a first length and a stiffness that is greater than the regions of lower stiffness, wherein the first length is between about 0.1 and 1.1 times the radius of the catheter; an inner puller coupled to a distal end of the tractor; and a guidewire lumen extending through the catheter, tractor and the inner puller and configured to pass a guidewire.

Thus, the regions of higher stiffness may have a longitudinal length along the flexible tube that is between about 0.05 and 1.2 (e.g. between 0.1 and 1.1 between 0.2 and 1 between 0.3 and 1 between 0.5 and 1, between 0.5 and 1.1, etc.) times the radius of the catheter. The the regions of higher and lower stiffness may be helically arranged around the flexible tube. In any of these apparatuses, the ratcheting motion may be seen by an oscillation of the diameter of the distal end-facing end of the tractor as it rolls over the catheter. For example, the diameter of the distal-facing end of the tractor may oscillate as the tractor is pulled proximally within the catheter to invert the tractor over the distal end of the catheter.

As mentioned, the tractor may be formed of a woven and/or knitted material. For example tractor may comprise a knitted material comprising one or more of: steel, polyester, nylon, expanded Polytetrafluoroethylene (ePTFE), and Nitinol. The tractor may comprise a sheet of one or more of: steel, polyester, nylon, expanded Polytetrafluoroethylene (ePTFE), Nitinol, or a fabric. The sheet may comprise a plurality of cut-out regions modifying the stiffness.

Methods of operating any of the apparatuses described herein (including the apparatuses including a ratcheting or see-saw tractors) are also described herein.

As mentioned above, any of the apparatuses described herein may be configured to prevent jamming by pre-biasing the tractor region so that it has an inner diameter in a first configuration within the lumen of the catheter (referred to for convenience herein as the "un-inverted" configuration, relative to the configuration of the portion of the tractor that has rolled over the distal end opening of the catheter) has a greater outer diameter than the inner diameter of the catheter. Further, any of the apparatuses described herein may also have an inner diameter in a second configuration over the catheter (referred to herein as the "inverted" configuration, relative to the first configuration) that is greater than the outer diameter of the catheter.

For example, described herein are mechanical thrombectomy apparatus for removing a clot from a vessel without jamming comprising: an elongate inversion support comprising a catheter having a distal end and a distal end opening; a tractor comprising a flexible tube that extends distally in a first configuration (e.g., an "un-inverted" configuration) within the catheter, inverts over the distal end opening of the catheter and extends proximally in a second (e.g., "inverted") configuration along the distal end of the catheter, wherein the tractor comprises a tubular wall, further wherein the tractor is configured to invert by rolling over the distal end opening of the catheter when a first end of the tractor is pulled proximally within the catheter, wherein the tractor is biased to expand to have an inner diameter that is greater than the outer diameter of the catheter in the inverted configuration and is biased to expand to have an inner diameter that is greater than the inner diameter of the catheter in the un-inverted configuration; and an elongate puller coupled to the first end of the tractor.

A mechanical thrombectomy apparatus for removing a clot from a vessel without jamming may include: an elongate inversion support comprising a catheter having a distal end and a distal end opening; a tractor comprising a flexible tube that extends distally in a first (an "un-inverted") configuration within the catheter, inverts over the distal end opening of the catheter and extends proximally in a second (an "inverted") configuration along the distal end of the catheter, wherein the tractor comprises a tubular wall, further wherein the tractor is configured to invert by rolling over the distal end opening of the catheter when a first end of the tractor is pulled proximally within the catheter, wherein the tractor is biased to expand to greater than the outer diameter of the catheter in the inverted configuration and is biased to expand to greater than the inner diameter of the catheter in the un-inverted configuration; an elongate puller coupled to a first end of the tractor and configured to pull the tractor proximally to invert the tractor over the distal end opening; and a guidewire lumen extending through the elongate inversion support, puller, and tractor that is configured to pass a guidewire. The tractor may be any of the tractors described herein, e.g., a woven tube, a braided tube, a knitted material, etc.

Any of the apparatuses described herein may be used with or may include an outer catheter within which the elongate inversion support extends distally; this outer catheter may be referred to as a sleeve or sheath, or in some variations an "intermediate" catheter, as it may be positioned, e.g., using a guidewire or by itself, first within the vasculature and then the elongate inversion support and tractor may be inserted within it to guide them to the clot to be removed, including after removing the guidewire, or leaving the guidewire in position. Any of these devices may be used with a vacuum to help capture and pull clot. For example, if an outer catheter is used, the outer catheter (within which the elongate inversion support can extend distally) may be proximally coupled to a vacuum source. The elongate inversion support may be configured as described herein to permit drawing the vacuum to the end of the elongate inversion support and/or outer catheter. For example, the elongate inversion support may have a diameter that is leaves sufficient clearance. In particular, the apparatus may be configured so that there is at least about 0.002 inches or greater (e.g., 0.003 inches or greater, 0.004 inches or greater, 0.005 inches or greater, 0.006 inches or greater, etc.) between the outer diameter of the catheter and the inner diameter of the outer catheter. The elongate inversion support may have a catheter with the distal end opening about which the tractor inverts that extends only part ways from the distal end towards the proximal end of the elongate inversion support. For example, the full catheter portion of the elongate inversion support may extend less 0.5 cm or less, 1 cm or less, 2 cm or less, 3 cm or less, 4 cm or less, 5 cm or less, etc. In some variations the elongate inversion support comprises a catheter that is skived at the proximal end. The catheter, and particularly the distal end region of the elongate inversion support, may include one or more openings, slots, holes, windows, cut-out regions, etc. for allowing vacuum to pass from the outer sleeve and preventing choking of the flow of vacuum from the distal end of the apparatus.

As mentioned, in any of the variations described herein, the tractor may be configured to collapse radially under an axial compression of less than 200 g of force. Thus, the tractor may be sufficiently soft and easy to roll (and invert) over the distal end aperture (distal end opening, e.g. of a catheter of the elongate inversion support). Similarly, the elongate inversion support may be configured to withstand buckling of an axial compression of greater than 500 g of force, sufficient to allow pulling of the tractor over the distal end opening (e.g. aperture) of the elongate inversion support without collapsing, kinking or displacing the elongate inversion support. In some variations, and particularly peripheral vascular variations, the elongate inversion support is configured to withstand buckling of an axial compression of greater than 1500 g of force.

Any of the apparatuses described herein may include a tractor having one or more coatings from the group of: a lubricious coating, a metal coating, a heparin coating, an adhesive coating, and a drug coating.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1H illustrate an example of an apparatus for mechanically removing an object such as a clot form a body region. FIG. 1A shows an example of an elongate inversion support portion of an apparatus, configured as a catheter portion. For example, at least the distal end of the elongate inversion support may be configured as a catheter. FIG. 1B shows an enlarged view of a distal end (opening) of the catheter of the elongate inversion support of FIG. 1A, showing the aperture formed by the distal end opening; FIG. 1C shows an example of a distal tractor region of a flexible tube (tractor tube) extending from a puller (the puller in this example is configured as a catheter. The tractor is shown in a first (e.g., un-inverted) configuration) and may be biased open, e.g., by heat setting, to have an outer diameter that is greater than the inner diameter of the catheter of the elongate inversion support, as shown in FIG. 1D. FIG. 1D shows the same distal tractor region of FIG. 1C with the expandable first end region expanded. This first configuration may be compressed down into the elongate inversion support and the distal end inverted over the catheter portion of the elongate inversion support, as shown in FIG. 1E. In FIG. 1E, the assembled mechanical thrombectomy apparatus with the elongate inversion support and the flexible tube forming the tractor is shown. The tractor extends through the catheter of the elongate inversion support and doubles back over the distal end opening of the catheter and extends over the outer diameter of the catheter. The outer portion of the tractor (extending along the outer diameter of the catheter) may be held in a collapsed configuration (as shown in FIG. 1E), or it may be expanded, as shown in FIG. 1F. Thus, the tractor may be biased so that in the second configuration (inverted over the distal end of the catheter), the tractor has a 'relaxed' outer diameter that is greater than the outer diameter of the catheter of the elongate inversion support. FIGS. 1G and 1H illustrate the use of the apparatus of FIGS. 1E and 1F to remove a clot by drawing the flexible tube proximally and/or advancing the catheter distally towards the clot so that the expandable first end region inverts as it is drawn into the distal end of the catheter, pulling the clot into the catheter.

In FIG. 1I, the tractor is shown attached to the distal end of a tapered or narrow puller; the distal end region is tapered, and includes a radiopaque marker at or near the attachment site to the tractor; the tractor may be knitted, braided, woven, etc. Thus, in some variations the distal end region of the puller may have a greater flexibility than the proximal end of the puller. The puller may be hollow (e.g., a catheter or hypotube) or solid (e.g., like a wire).

In FIG. 2A the mechanical thrombectomy apparatus includes a tractor region that collapses within the inner diameter (lumen) of the catheter portion of the elongate inversion support, jamming so that the tractor region cannot roll, without applying excessive force, or at all, around the open end of the catheter. Similarly, in FIG. 2B, the tractor region is loose, and also jams on the distal open end of the catheter as it inverts.

FIGS. 3A-3C illustrate the operation of a mechanical thrombectomy apparatus having a tractor region such as that shown in FIG. 2C capturing a clot. In FIG. 3A the apparatus is positioned adjacent to the clot. FIG. 3B shows an alternative variation in which a guidewire is used to position the apparatus; the guidewire may remain in place during capture of the clot, or it may be removed. FIG. 3C shows the apparatus capturing the clot by rolling the tractor portion of the apparatus over the end of the catheter of the elongate inversion support as the tractor portion is drawn proximally; the apparatus may be advanced distally within the lumen of the vessel.

In FIG. 4A the tractor portion is configured to include a central guidewire lumen and a hypotube (inner catheter) is used to pull the proximal end of the tractor; in FIG. 4B the tractor is configured to collapse down to a puller wire.

In FIG. 5A the tip is shown with a slightly proximally-offset from the distal end marker band; in FIG. 5B the tip of the catheter has been folded back over itself, increasing both the diameter of the catheter at the distal end and the stiffness of the distal end.

FIG. 6A is an example of a side perspective view and FIG. 6B shows the distal end face of the apparatus.

FIGS. 7A-7E illustrate examples of heat set 0.085" ID PET (FIGS. 7A-7C) tractors and nickel titanium heat-set 0.085" ID tractors.

FIGS. 8A-8D illustrate operation of mechanical thrombectomy apparatus pulling in a clot. FIGS. 8E-8F illustrate reversal of the apparatus of FIGS. 8A-8D, ejecting the clot.

FIG. 16A shows a top perspective view and FIG. 16B is a side view.

FIG. 20B is an enlarged view of the pattern of FIG. 20A.

FIGS. 21A-21B show an example of a pattern that may be use to form a tractor region. FIG. 21B is an enlarged view of the pattern of FIG. 21A.

FIGS. 22A-22B show an example of a pattern that may be use to form a tractor region. FIG. 22B is an enlarged view of the pattern of FIG. 22A.

FIG. 23B is an enlarged view of the pattern of FIG. 23A.

FIG. 24B is an enlarged view of the pattern of FIG. 24A.

FIG. 30A schematically illustrates a portion of a tractor having alternating stiff/less stiff regions. FIGS. 30B-30D illustrate the seesawing motion of a tractor having alternating stiff/less stiff regions.

FIG. 31A is an example of a knitted tractor having alternating more stiff/less stiff regions extending in a corkscrewing/helical pattern along the length of the tractor.

FIGS. 31B-31C show side and end views, respectively of an apparatus having a knitted tractor, similar to that shown in FIG. 31A.

FIGS. 31D and 31E show side and end views, respectively of an apparatus having a knitted tractor.

FIG. 41A illustrates a method for removing clot using an intermediate catheter (e.g., sleeve) and a vacuum, in which a mechanical thrombectomy apparatus is extended from a distal end of the intermediate catheter to remove a clot.

FIG. 41B illustrates a method for removing clot using an intermediate catheter (e.g., sleeve) and a vacuum, in which a mechanical thrombectomy apparatus removes a clot that has been drawn into the distal end of the intermediate catheter.

DETAILED DESCRIPTION

Figure 1E:
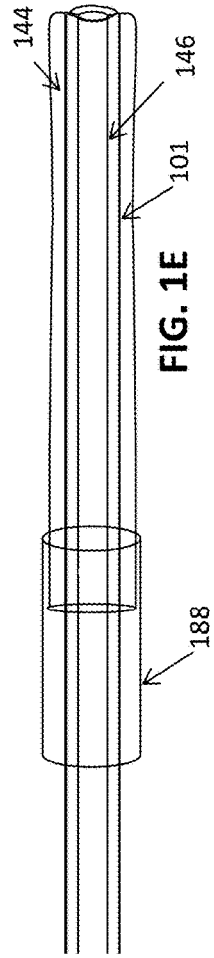

In general, described herein are mechanical thrombectomy apparatuses having an inverting tractor that is configured to prevent jamming and grab a blood clot. These apparatuses may include an elongate elongate inversion support support that supports an annulus over which the tractor inverts at the distal end. The tractor may comprise a flexible tube that doubles back over (e.g., inverts) over the distal end of the elongate inverting support (e.g., a catheter) so that it extends into the annuls opening of the elongate inverting support and an inner puller coupled to the inner end of the tractor that the tractor can be pulled proximally to pull and invert the tractor over the annulus at the distal end of the elongate inverting support to roll and capture a clot. The apparatus may include a guidewire lumen extending through the elongate inverting support, and/or tractor puller that is configured to pass a guidewire.

Any of the apparatuses described herein may be adapted to prevent jamming, e.g., by including a coating (e.g., hydrophilic, lubricious coating, etc.) or the like to enhance the sliding and inverting of the tractor over the distal end. Further, any of these apparatuses may include one or more projections that are configured to enhance grabbing and/or maceration of a clot. Grabbing of a clot may be particularly, but not exclusively, helpful when the tractor is lubricious. Although lubricious tractors may may resist jamming and require less force to operate, e.g., inverting over the distal end of the catheter, it may be more difficult to initially grab or grasp clot when the tractor is more lubricious. It may also be particularly helpful to include projections that are retracted along the length of the tractor adjacent to the outer diameter of the elongate inverting support (e.g., catheter), for example, when positioning the apparatus within a vessel, but extend the projections outward from the tractor when rolling and inverting to grab a clot.

In general, a mechanical thrombectomy apparatus for removing a clot from a vessel may be a system, assembly or device including an elongate inversion support having a distal end and a distal annulus, and a flexible tractor assembly at least partially inverted and configured to roll and invert over the distal annulus of the elongate inverting support.

In many of the examples described herein, the elongate inversion support is a catheter (or a portion of a catheter at the distal end) and the annulus is formed by the distal end opening of the catheter; the tractor extends within the catheter and doubles back over the distal end of the catheter to extend over the outer diameter of the catheter at the distal end of the catheter, although it may extend proximal for any appropriate distance (including between 1-30 cm, between 2-20 cm, greater than 1 cm, 2 cm, 3 cm, 4 cm, 5 cm, 6 cm, 7 cm cm, 8 cm, 9 cm, 10 cm, 11 cm, 12 cm, 15 cm, 20 cm, etc.). The end of the tractor within the catheter may be coupled to a puller (e.g., at a proximate puller region connected to the distal or inner end of the tractor). The tubular tractor may include an elongate lumen that is configured to allow passage of a guidewire. The tubular tractor may also be configured to slide along the long axis within the catheter lumen and invert over the distal end opening of the catheter when the proximal end region is pulled proximally. The tractor may be referred to herein as a tractor assembly, tractor portion, tractor tube, or simply a tractor, and is typically positioned and longitudinally slideable within the catheter, and arranged so a portion of the tractor (sometimes referred to as the "distal tractor region" or "distal-facing" tractor region) doubles back over itself.

For example, FIG. 1A shows one variation of a catheter of an elongate inversion support that may form part of the apparatuses described herein. In this example, the elongate inversion support includes a catheter 100 having a distal end region 103 that includes a distal end opening 105. The distal end region may have an increasing softness (measured by durometer, e.g., shore durometer) except that the very distal-most end region (distal end 105, including the distal end opening) may be substantially less soft than the region immediately proximate to it. Thus, although the distal tip region of the catheter (e.g., the distal most x linear dimensions, where x is 10 cm, 7 cm, 5 cm, 4 cm, 3 cm, 2 cm, 1 cm, 9 mm, 8 mm, 7 mm, 6 mm, 5 mm, 4 mm, 3 mm) has an increasing softness/decreasing harness extending from the proximal to distal ends, the very distal end region 107 (e.g., measured as distal most z linear dimensions, where z is 1 cm, 9 mm, 8 mm, 7 mm, 6 mm, 5 mm, 4 mm, 3 mm, 2 mm, 1 mm, 0.8 mm, 0.5 mm, 0.3 mm, 0.2 mm, etc., and z is always at least three times less than x) has a hardness that is greater than the hardness of the region immediately proximal to it, and may be as hard or harder than the proximal-most region of the distal tip region.

In FIG. 1A, the elongate inversion support is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or less of of compressive force is applied (e.g., at least about 700 g, 600 g, 500 g, 400 g, 300 g, etc. of compressive force) for neurovascular applications. For peripheral vascular applications the elongate inversion support may be selected or configured to withstand at least 1500 g of compressive force (e.g., at least about 2000 g, 1900 g, 1800 g, 1700 g, 1600 g, 1500 g, 1400 g, etc. of compressive force). In general, any of the apparatuses described herein may include a elongate inversion support that is not a full-length catheter, but may include a portion of a catheter, typically at the distal end, connected to a rod, wire, hypotube, or the like (as will be described in greater detail below in reference to FIGS. 42A-43D) or may be skived. Thus, any of the apparatuses and methods described herein may be adapted for use with an elongate inversion support that is not limited to catheters, including elongate inversion supports that include a portion of a catheter, or that include a ring or other structure forming the annulus at the distal end. In FIG. 1A the catheter 100 of the elongate inversion support may be any appropriate type of catheter or portion of a catheter, including microcatheters appropriate for neurovascular use.

In some variations the distal end 105 of the elongate inversion support is adapted so that the tractor may slide or roll and invert over the distal end of the catheter without being caught (binding, jamming) or without substantial friction. For example, in some variations the distal tip (end) may be curved or radiused 109 as shown in FIG. 1B, particularly on the outer surface (e.g., the transition from outer diameter to inner diameter).

FIG. 1C shows an example of a flexible tractor 144 coupled to a puller 146. In this example to form a pullable tractor assembly 140, the tractor is shown integrated with the puller, forming the assembly. In FIG. 1C, the tractor is a tube of material (e.g., wove, knitted, braided, etc.) that is flexible and elongate. The tractor is shown extended from the puller in a first configuration. It may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). In the example shown in FIG. 1C, the tractor 144 is configured, e.g., by shape-setting (heat setting, etc.), to expand in the relaxed first configuration to a radial diameter that is between 1.1 and 0 times the diameter of the inner diameter of the catheter of the elongate inversion support when unconstrained, as shown in FIG. 1D. In FIG. 1D, the tractor of FIG. 1C is shown in an expanded, relaxed, configuration. Thus the expandable tractor may be biased to expand open. The tractor may be formed of a mesh, braided, woven, knitted, or sheet of material and is generally adapted to grasp the object to be removed (e.g., blood clot).

In FIGS. 1C and 1D the tractor and puller have two portions, a tractor 144 and a less expandable (or non-expandable) proximal portion comprising the puller 146. The puller may be a separate region, such as a wire, catheter or hypotube, which is connected to an end region of the tractor (e.g., a flexible mesh, woven, braided, etc.), e.g., the distal end or near the distal end. The inverting region of the tractor, where it rolls and inverts over the distal end opening of the catheter may be referred to as the distal-facing region of the tractor, which may actively grab clot when rolling.

Figure 1F:
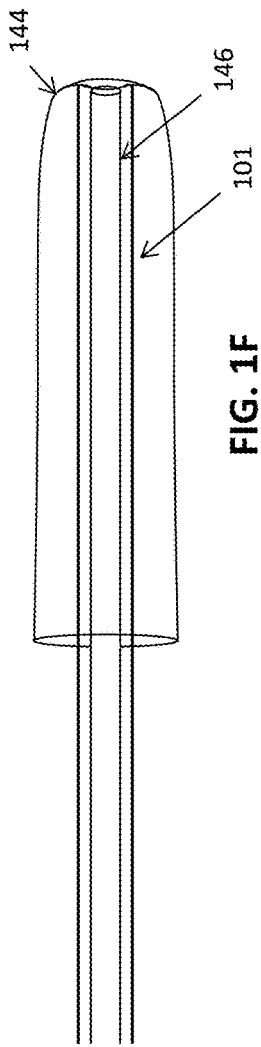

In FIG. 1E, the flexible tractor of FIG. 1C is shown with the tractor doubled back over itself an over the the distal end of the catheter of the elongate inversion support 101. The distal end region is collapsed down, e.g., onto the puller and the elongate inversion support, and may be held collapsed. In this example a tractor hold 188 may be used to hold the tractor collapsed down onto the outer diameter of the elongate inversion support. However, in an unconstrained or deployed configuration, as shown in FIG. 1F, the tractor in this second configuration (e.g., the portion that is inverted over the distal end of the catheter) has an outer diameter that is greater than the outer diameter of the catheter of the elongate inversion support. Thus, the tractor 144 may be biased so that it has a relaxed expanded configuration in the first configuration (as shown in FIG. 1C) that is greater than the inner diameter (ID) of the catheter of the elongate inversion support portion of the apparatus and the relaxed expanded configuration of the second configuration (shown in FIG. 1F) inverted over the catheter has an OD that is greater than the OD of the catheter. The tractor is expandable and may be coupled to the puller. In some variations the flexible tractor and the puller may comprise the same material but the tractor may be more flexible and/or expandable, or may be connected to a push/pull wire or catheter.

Figure 1G:
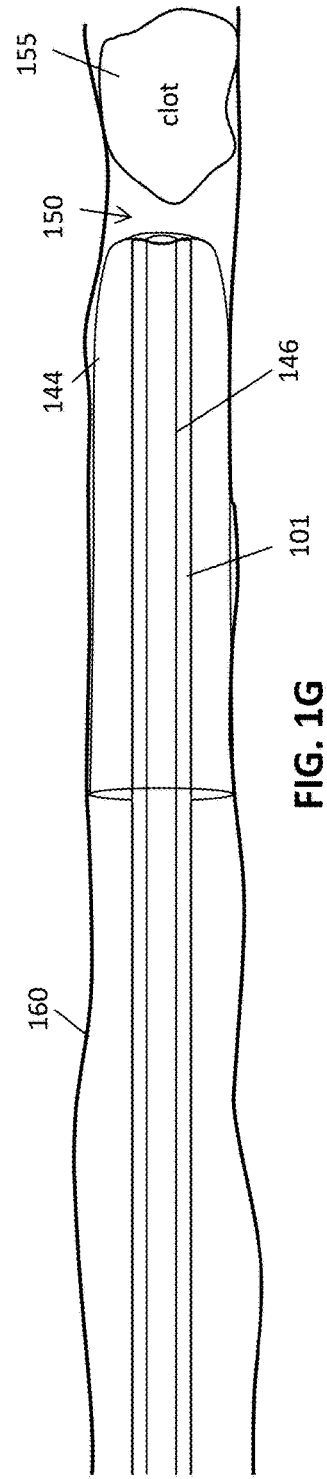
Figure 1H:
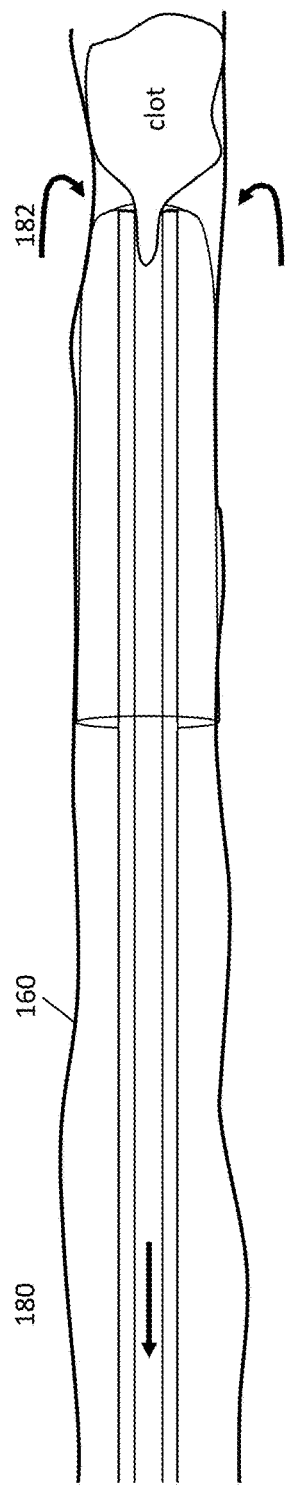
Figure 1I:
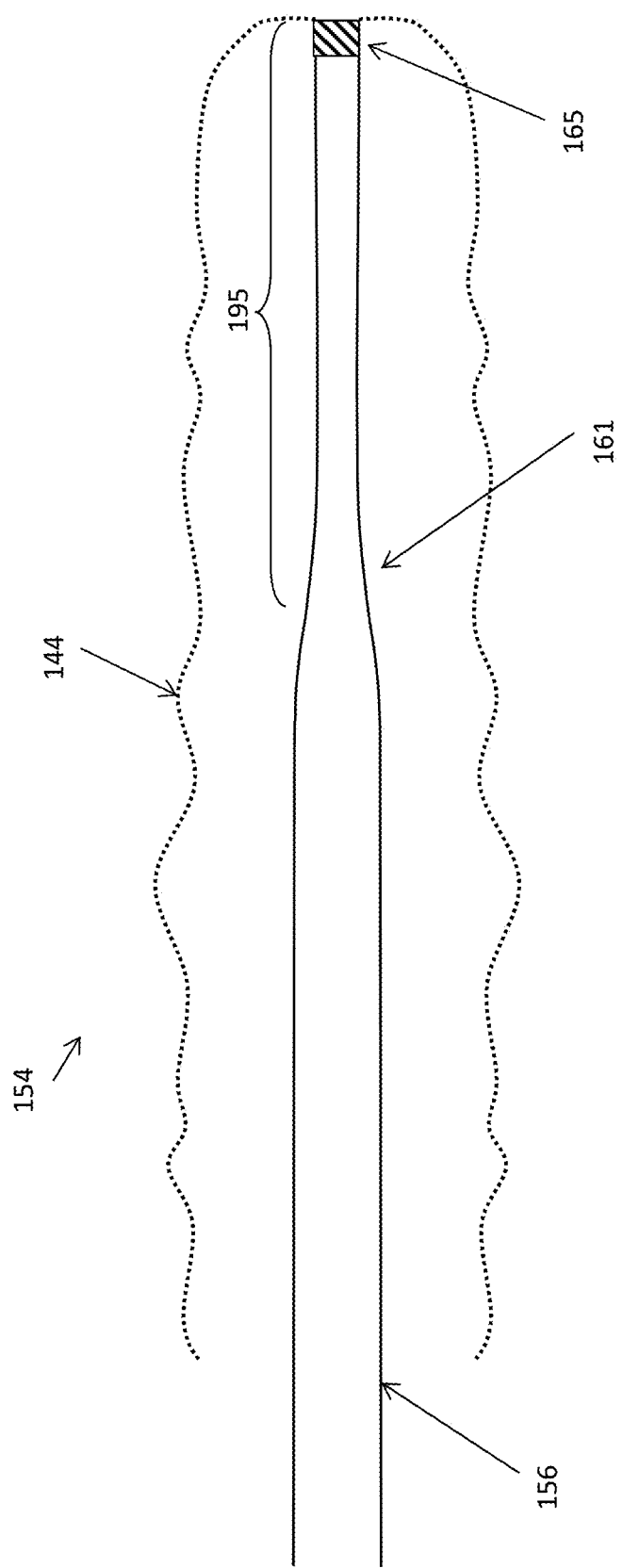
FIG. 1I illustrates an alternative variation of a tractor and puller.

FIGS. 1G and 1H illustrate the removal of a clot using an apparatus such as the apparatus assembled from the components of FIGS. 1A and 1E. In this example the apparatus is configured as a thrombectomy apparatus including a catheter of an elongate inversion support 101 and a flexible tractor that extends over the distal end region of the catheter and doubles-over itself at the distal end of the catheter to invert so that the external tractor end region is continuous with an inner less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor. In FIG. 1G the apparatus is shown positioned and deployed within the vessel 160 near a clot 155. The clot may be drawn into the catheter by pulling the tractor 140 proximally into the catheter 101, as indicated by the arrow 180 showing pulling of the inner portion of the flexible tractor (e.g., using a handle, not shown) resulting in rolling the tractor over the end opening of the catheter and into the catheter distal end and inverting the expandable distal end region so that it is pulled into the catheter, shown by arrows 182. The end of the tractor outside of the catheter may be "loose" relative to the outer wall of the catheter. FIG. 1I illustrates another example of a tractor assembly 154 including a tractor 144 that is coupled to a puller 156. The puller in this example is tapered (having tapering region 161) and may therefore have a different flexibility of the distal end region than the proximal end region. For example the proximal end region may be less flexible than the narrower-diameter distal end region 195 to which the tractor is coupled. The assembly includes a radiopaque marker 165. The tractor may be attached to the puller by any appropriate means. For example, the tractor may be crimped, glued, fused, or otherwise attached to the puller, typically permanently.

In general the mechanical thrombectomy apparatuses described herein may be highly flexible, both before actuating and during operation. For example, the flexible tractor may not increase the stiffness/flexibility of the catheter of the elongate inversion support, and particularly the distal end region of the catheter too much, to avoid impacting maneuverability, particularly within tortious vessels of the neurovasculature. Described herein are flexible tractor tube portions that increase the stiffness of the last y cm (e.g., distal most 20 cm, 18 cm, 15 cm, 12 cm, 10 cm, 9 cm, 8 cm, 7 cm, 6 cm, 5 cm, 4 cm, 3 cm, 2 cm, 1 cm, etc.) of the catheter less than a predetermined percentage (e.g., less than 10%, 12%, 15%, 18%, 20%, 25%, 30%, etc.). For example, described herein are flexible tractor tube portions that pass through the catheter and double back over the distal end of the catheter but increase the stiffness of a distal 5 cm of the catheter by less than 15% of the stiffness of the distal 5 cm of the catheter without the flexible tube extending therethrough and doubling back over the distal end of the catheter.

Figure 2A:
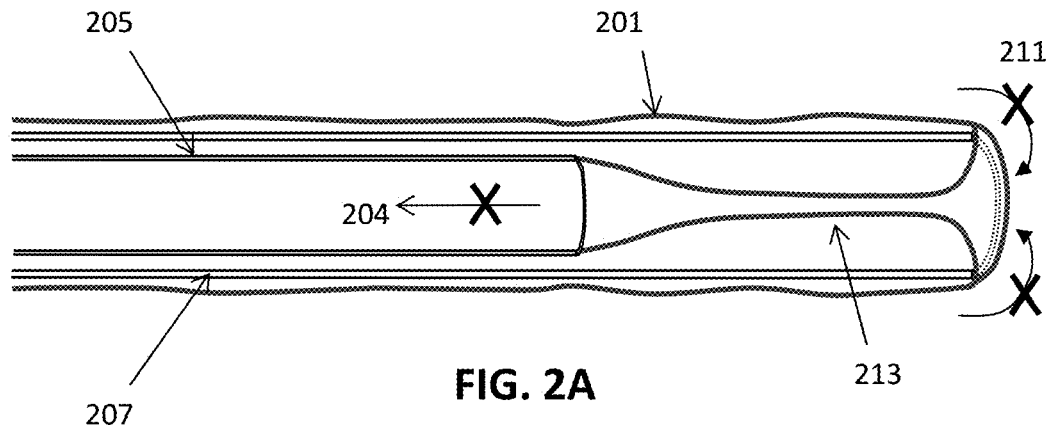
FIGS. 2A and 2B illustrate jamming of a mechanical thrombectomy apparatus.
Figure 2B:
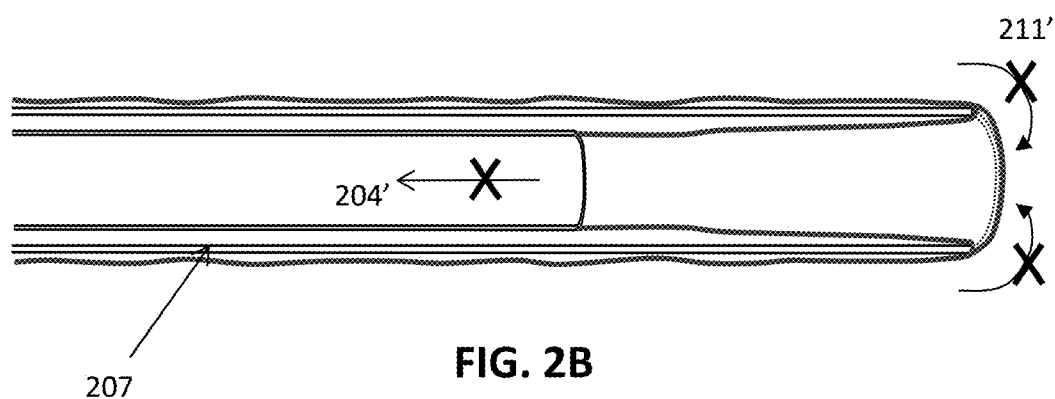

Jamming may occur if the tractor cannot easily invert over the distal end of the catheter, as shown in FIGS. 2A and 2B. In FIG. 2A, pulling the tractor 201 proximally from within the catheter 207 of the elongate inversion support, e.g., by pulling 204 on the inner puller catheter 205, would normally cause the tractor to roll 211 over the distal end of the catheter tip. If the force required to pull the tractor so that it inverts and rolls into the catheter is too great, such as 200 g of force (e.g., greater than 10 g force, greater than 20 g force, greater than 30 g force, greater than 40 g force, greater than 50 g force, greater than 60 g force, greater than 70 g force, greater than 80 g force, greater than 90 g force, greater than 100 g force, etc.), exclusive of any initial deployment force to release the tractor, described herein, then the device is jammed. Typically the tractor may be pulled and inverted over the distal end opening with significantly less force that this jamming force. Jamming may lead to collapse of the elongate inversion support, and device failure. Jamming may occur when, for example, the tractor gets caught on the distal end opening of the catheter of the elongate inversion support. In FIG. 2A, one failure mode leading to jamming results when the portion of the tractor within the catheter 213 collapses inward, as shown. The inventors have found that it is desirable, and may prevent jamming, if the portion of the tractor within the catheter collapses only so that it has a diameter (e.g., inner diameter) of 40% or more of the inner diameter of the catheter (e.g., 45% or more, 50% or more, 55% or more, 60% or more, 65% or more, 70% or more, 75% or more, etc. of the inner diameter of the catheter).

Similarly, FIG. 2B illustrates another example of an apparatus in which jamming has occurred, as indicate by the "X" through the arrows showing the proximal movement of the tractor within the catheter 204' and rolling 211' of the distal-facing inverting portion of the tractor. In FIG. 2B, the tractor bends sharply around the distal end of the catheter. This sharp bend may result in jamming over the distal end of the catheter, as shown.

Figure 2C:
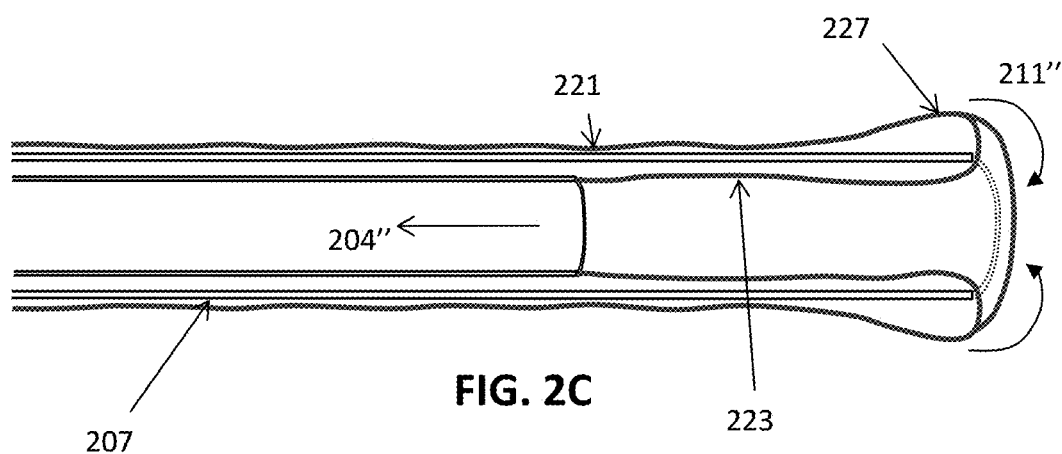
FIG. 2C illustrates an example of an anti-jamming configuration, in which the distal-facing, inverting portion of the tractor is flared outwards at an angle, so that the portion of the tractor on either side of the catheter end approaches at an angle of less than 45 degrees relative to a length of the tractor (e.g., 0.5 mm, 1 mm, 2 mm) on either side of the opening. In this example, the portion of the tractor that is around the outer diameter is biased to contract down onto the outer diameter of the catheter, and after inverting the bias is to expand outward slightly, resulting in the trumpet-shaped inverting region. Even in this configuration, the tractor may be set (e.g., biased) so that the outer diameter of the first configuration (within the catheter of the elongate inversion support) has a greater outer diameter than the inner diameter of the catheter in the relaxed state (e.g., when not compressed and constrained in the catheter inner diameter), and the outer diameter of the tractor in the second configuration (inverted over the outer diameter of the catheter of the elongate inversion support) is greater than the outer diameter of the catheter. In some variations the unconstrained first configuration has a greater OD than the unconstrained OD of the second configuration. Alternatively, the unconstrained OD of the first configuration may be less than the OD of the unconstrained OD of the second configuration.

Various features that may be used alone or in any combination to prevent jamming of the tractor on the catheter are described herein. For example, in FIG. 2C, a the tractor may be biased so that the portion of the tractor within the catheter in the first configuration 223 (e.g., extending from the puller in an un-inverted configuration in FIG. 2C) would have a relaxed outer diameter (OD) that is approximately equal to or greater than the ID of the catheter (e.g., the relaxed OD of the tractor is between 0.8× to 3× the ID of the catheter), and the OD of the tractor in a second configuration (inverted relative to the first configuration) 221 is typically greater than or approximately equal to the OD of the catheter (e.g., the relaxed OD of the tractor in the second configuration is between about 0.9× and 5× the OD of the catheter, e.g., >1× the OD of the catheter, etc.). It should be noted that the tractor may be configured so that the relaxed OD of the first configuration of the tractor is greater than the relaxed OD of the tractor in the second (inverted) configuration, or vice versa. This combination of biasing may result in a distal-facing inverting region that is slightly trumpet-shaped 227, as shown. This trumpet shape may result in an angle of approach between the surface of the tractor and the open end of the catheter that is more close to perpendicular relative to the open end, as can be seen by comparing FIG. 2C with FIGS. 2A and 2B. The outwardly-flaring distal-facing tractor region may therefore prevent jamming. FIGS. 3A-3C illustrate the operation of an apparatus including a tractor region that flares outward at the distal-facing rolling/inverting region as it rolls over the distal end of the catheter. In FIG. 3A, the apparatus 305 is driven down the vessel 160 into proximity with the clot 155. A guidewire 309 may be used to aid in positioning, as shown in the alternative view of FIG. 2B. For example, a guidewire may be first guided to the clot, and the apparatus may then be slid over the guidewire to position adjacent to the clot. The guidewire may be left in place or removed before actuating the apparatus as shown in FIG. 3C to remove the clot. In FIG. 3C, the apparatus is actuated by drawing proximally 309 on the inner portion of the tractor 311 so that it rolls and inverts 182 over the distal end of the catheter, as shown. The inverting tractor grabs and pulls the clot into the catheter, compressing and/or distorting it as it pulls it inside. The apparatus may be advanced distally as the tractor is pulled proximally. In some variations the tractor may be expanded longitudinally (distally-proximally) within the catheter as it is drawn proximally within the catheter, because it may be a woven, knitted or elastic material. This may allow the clot to be drawn in quickly and may secure it within the catheter.

The tractors may be woven, braided and/or knitted materials. For woven and braided materials, which may include a plurality of fibers that are woven or braided to form the inverting tube, these structures may be tuned to prevent jamming and/or to reduce the force necessary to pull the tractor and invert over the catheter tip. For example, the mechanical atherectomy apparatus may include a braid-type tractor that can roll freely around the tip of catheter even in a tortuous anatomy and when grabbing clot by tuning one or more of the braid structure; minimizing the braid angle; including a hydrophilic coating on the distal aspect of the catheter outer diameter (OD) or the inner diameter (ID) of the braid (e.g., tractor); including a radiused wall on the catheter; and/or increasing the stiffness of the distal tip region relative to adjacent proximal regions.

As mentioned, the tractor (e.g., braided, woven, knitted, etc.) may be configured to collapse down into the inner diameter (ID) of the catheter as little as possible. For example the tractor may collapse to an ID that is greater than, equal to, or within 90%, 85%, 75%, 70%, 65%, 60%, or 50% of the catheter inner diameter (ID)/Catheter Tip OD, since, when the tractor is being pulled around catheter tip it may create axial tension on the tractor (e.g., braid, knit, etc.) that can inadvertently cause the tractor to jam on the catheter tip. When tractor is pulled around catheter tip, the tractor is being pulled in the axial orientation creating axial tension on tractor structure as the tractor is being pulled through the catheter ID. By having the tractor elements jam at an ID greater than or equal to 90%, 85%, 75%, 70%, 65%, 60%, or 50% of the catheter ID (or in some variations, OD), when being axially tensioned, the tractor is less likely to grab/synch down onto the catheter tip, helping the braid roll around the catheter tip with less axial force applied by the user. If less axial force is required by the user to pull the tractor structure around the tip then the catheter tip is less likely to buckle or deflect when retracting the tractor. It may be advantageous to minimize the chance the catheter tip will buckle. The tractor can be tuned to "jam" at a specific ID by controlling any of the following variables and in any combination: selecting a specific number of braid ends, selecting the size/diameter of the braid ends; selecting the braid material (e.g., multifilament or monofilament); heat setting the bias on the braid (e.g., braid diameter); and selecting a braid pattern, e.g., 1×2, 1×1 or any other pattern.

The braid angle may be minimized to prevent locking up of the rolling of the tractor over the catheter end opening. Typically, the lower the braid angle (e.g., 45 degrees or less, 40 degrees or less, 35 degrees or less, 30 degrees or less, 25 degrees or less, 20 degrees or less, etc.) the less likely it is to have the braid cross over points catch on the catheter tip.

In any of the variations described herein, the catheter and/or a surface of the tractor may be coated to enhance rolling over the distal end region of the catheter. It may be helpful to have a hydrophilic coating on the distal aspect of the catheter OD or the ID of the tractor so the tractor can more easily side over the catheters distal end and around the tip of the catheter when pulled through the inside of the catheter.

The radius wall of the catheter tip may be chosen/set to within a range that allows sliding. For example, it may be helpful for the tip of the catheter to have the largest radius possible but at least 0.0025" radius wall on the catheter, ideally approximately 0.005" radius wall.

The stiffness of the distal of the catheter may be sufficiently stiff to prevent collapse as the tractor is pulled; it may also be lubricious (e.g., by a coating or material property). The distal most section of the catheter tip (e.g., the last 5 mm) may be fabricated of a material which is stiff enough and lubricious enough so the distal tip of the catheter does not collapse or buckle inward ward when the braid structure is rolling around the catheter tip. Thus, the distal tip may have a stiffness that is greater than the more proximal region at the distal end of the catheter.

As will be described in greater detail below, it may be helpful or desirable to have pores in the tractor. A lack of gaps or small pore size may limit the ability of the braid to grab clot. Alternatively or additionally, it may be desirable to form a braid structure with texture. One example is to braid 2 or more different diameter braid ends into the same structure: the difference in braid end diameters will help form a texture to the braid structures outer surface, aiding the grabbing of the clot when rolling the braid-dozer around the catheter tip.

As an alternative (or in addition) the tractor may be configured to lock so it does not compress in diameter during axial load by adding a coating, laminate or adhesive to the braid at a desired diameter. Adding a thin coating, laminate or adhesive can inhibit the braid elements from sliding with respect to each other, thereby locking the braid to a specific diameter. The coating can be applied while leaving the majority of the pores and pore area substantially open. Examples of thin coatings include urethanes and silicones with and without hydrophilic coatings and hydrophilic coatings with no tie layer.

Reducing the sliding friction of tractor to outer catheter wall, improving tractor to tip rolling, and/or enhancing tractor to inner catheter sliding may also be achieved by including a sliding skin or sleeve. For example, a thin (e.g., ultrathin) sleeve may be used. The sleeve would be made from low friction polymer (PET, PE, PP, PTFE, ePTFE, pebax, urethanes) by braiding, knitting, weaving, extrusion, melt blown, melt spinning, etc. The sleeve could be made from laser slotted tubing, chemical etching, micro machining. The sleeve could be also coated with a lubricious coating such as a hydrophilic coating. Lubricious coatings can be located on the outside and/or inside surfaces. The sleeve may be placed between the dozer element and the catheter wall and attached to the puller element. The sleeve may be less than 0.002" thick, ideally, less than 0.001" wall thickness. The sleeve may decouple the tractor clot grabbing system from the catheter wall, tip rolling and inner catheter dragging friction. The sleeve could be totally free from the tractor, connected to the tractor in discrete locations or connected fully to the tractor. This may allow the tractor to be designed to grab clot (larger wires: 0.001" to 0.002" for neuro, and 0.002" to 0.007" for other applications) and the skin to minimized in thickness and structure to reduce friction and skin bending stiffness.

Figure 4A:
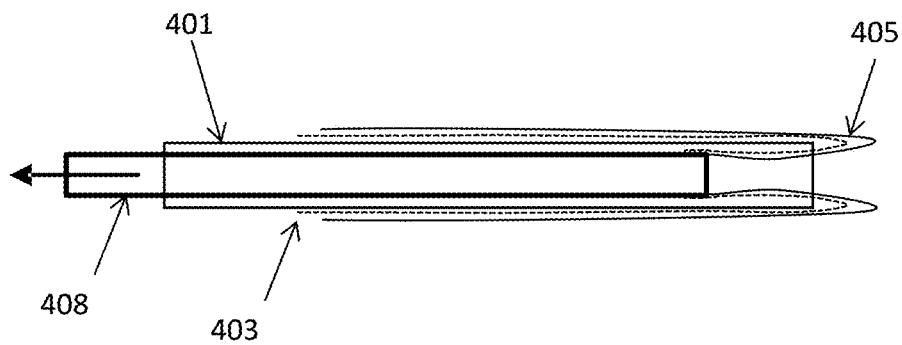
FIGS. 4A and 4B illustrate another example of a mechanical thrombectomy apparatus having a tractor in which an anti-jamming sleeve portion is included between the catheter outer diameter and the tractor.
Figure 4B:
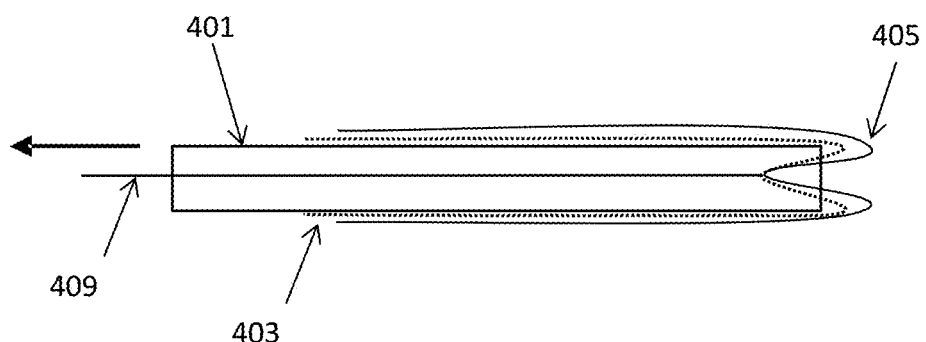

FIG. 4A shows one example of a sleeve that may be used. In this example, the sleeve 403, such as those described above, may be positioned between the catheter 401 outer diameter and the tractor 405. The sleeve (or "skin") may be inverted with the tractor, or it may be held on the outer diameter and the tractor moved over it. FIG. 4B is another example in which the tractor is pulled by a pull wire 409; in FIG. 4A the tractor is pulled by a puller catheter 408 within the outer device catheter 401.

In some variations, the tractor region may be formed of with a mixed or hybrid structure, combining one or more of interwoven or knitted braid polymer filaments with metallic filaments. The mixed structure (hybrid structure) may leverage both metallic elements interwoven with low friction polymer elements. The metallic filaments may create stiffness elements that may grip/grab a clot. The polymer filaments may aid in grabbing clot but may provide surface friction reduction to the outer catheter wall, the catheter tip and the inner catheter wall once around the tip.

Any of the apparatuses described herein may include a tractor having a hydrophilic/lubricous coating on the inside surface, e.g., for braided/knitted tractors, on the inside surface (contacting the outer and inner diameter of the catheter) of the braid/knit, which is in contact with the outside of the catheter. Examples of lubricous coatings include hydrophilic coatings (e.g., hydrogels) and hydrophobic coatings (e.g., fluorine coating such as PTFE & FEP, parylene, silicone, siloxane (silicone additive) added to various polymers including pebax to make any material more lubricious, Polyethylene, polypropylene, FEP)

Figure 5A:
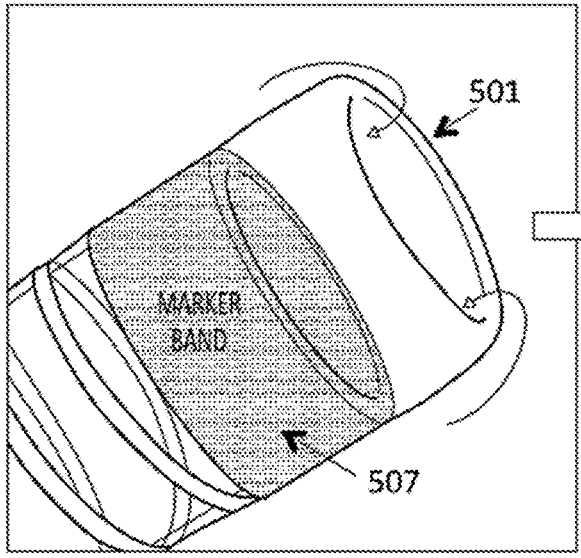
FIGS. 5A-5B illustrate formation of catheter tip having a stiffer distal end adapted to prevent jamming and/or collapse of the catheter distal opening when inverting a tractor over the distal end.
Figure 5B:
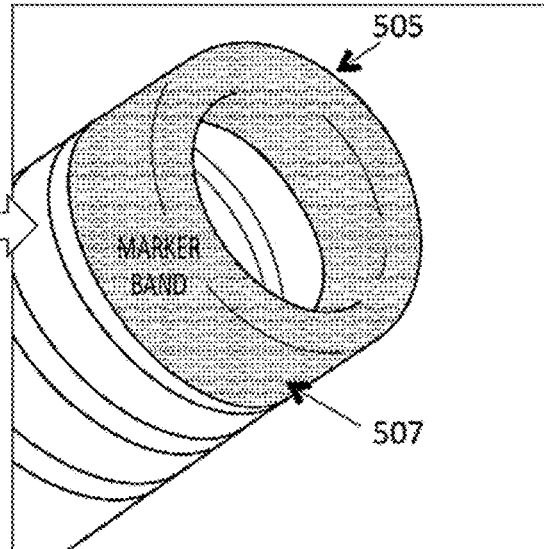

As mentioned above, any of these apparatuses may include a distal tip that is less rigid (e.g., 'softer') than the more proximal regions of the distal tip. This may be achieved by having a structural supporting member reinforcing the distal tip, or by modifying the material forming the distal tip. In some variations, the distal tip of the catheter may be stiffened (made more rigid) by inverting over the catheter end. See, e.g., FIGS. 5A-5B showing an inverted soft tip of a catheter. In this example, a 72-end PET braid was used to invert the tip 501 of the 0.071 catheter back over itself 505 as shown in FIG. 5B. Inverting the distal section of the catheter tip, which may include a hydrophilic coating, inside of the catheter and (in this example, though not a necessity) a radiopaque marker band 507. This may crease a larger radius tip which is relatively stiffer than the tip and has a hydrophilic coating around the outer diameter and inner diameter all the way on the last 2-5 mm of the catheter. Optionally, the catheter may be delivered with a tip similar to that show in FIG. 5A, but when the tractor is pulled initially into the catheter, the distal end of the catheter may invert to form the tip as shown in FIG. 5B.

Figure 6A:
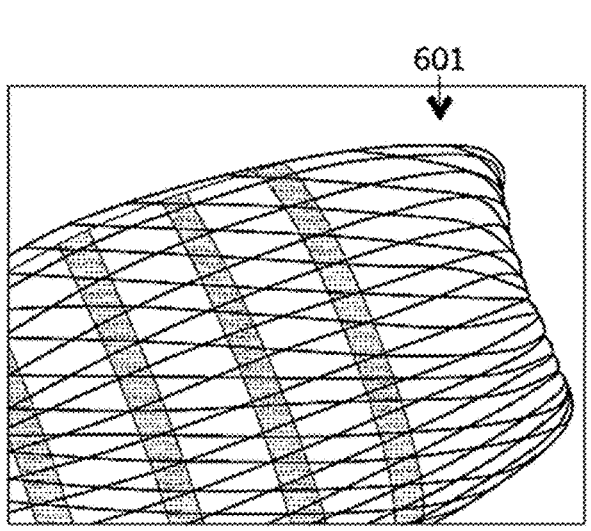
FIGS. 6A-6B is an example of a distal tip or end region of a catheter such as that shown in FIG. 5B, over which a tractor is inverting.
Figure 6B:
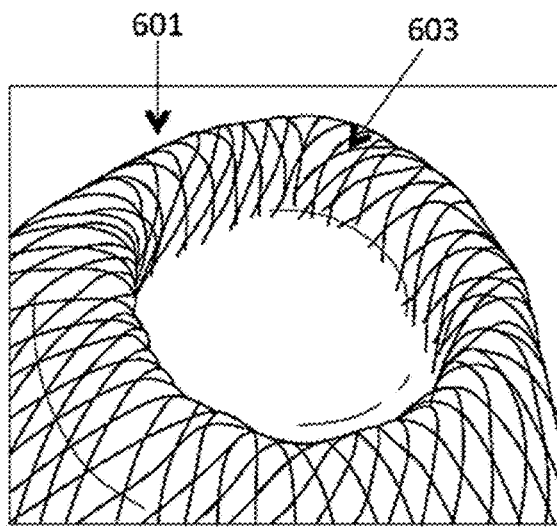

FIGS. 6A and 6B show another example of an inverted soft-tip catheter over which a tractor 601 (in this example, a PET braid having 72 ends and a 4×0.0008" material). The tractor in FIG. 6A is rolled over the hydrophilic coated tip 603 showing a large collapsed radius (e.g., it does not collapse down on itself). The coating of hydrophilic material enhanced the rolling of the material over the catheter. The catheter was loaded with the tractor having a small (2 mm) ID tube, which is very close to the catheter OD. In this example, 23 cm of tractor was pulled easily into the catheter having a rolled tip as shown in FIG. 5B. In this example, the tip did not collapse, however other tractor materials (e.g., metallic, such as Nitinol materials) may collapse the tip, even when inverted as shown.

FIGS. 7A-7F illustrate examples of braided tractors that may be used. In these examples, FIGS. 7A-7C show PET braids that are heat-set to 0.085" IDs (at 395° F. for 10 min). For example, FIG. 7A is a 0.001 inch PET, having 36 ends and a 77° braid angle at 9 mm, and 0.008 OD filaments. This example was highly porous, but was the least stable of all of the examples shown in FIGS. 7A-7F. FIG. 7B is a 72-end 0.001 polyester strand braid of 8 mm, 90° braid angle, with 4 filaments in each strand. FIG. 7C is a 48-end braid tractor of 0.002" polyester, 90° angle over 9 mm mandrel. The braid shown in FIG. 7A collapses 50% of the diameter, while the the braided tractor shown in FIG. 7B collapsed less than 5% of the diameter, and the braided tractor of FIG. 7C collapsed less than 25% of the diameter. FIGS. 7D and 7E show Nitinol braided tractors heat-set to 0.085" ID (at 510° C. for 8 min). These braided tractors were constrained to 0.070 inches to show the pore size when pulling into a 0.071 catheter. Other examples of braided tractors had between 96 or 144 ends of 0.0005"-0.0015" PET mono or 0.0005"-0.001" filaments with a <35° braid angle.

FIGS. 8A-8D illustrate the operation of a 72-end 0.001" NiTi tractor capturing clot in a model vessel. In this example showing pulling the clot into the catheter, the ID of the vessel is nearly the same as the OD of the catheter tip. Drawing the tractor into the vessel shows that the tractor region does not collapse down with inverted into the vessel, preventing locking of the end, and leaving space for drawing the clot, as shown. FIGS. 8E and 8F illustrate reversing the rolling movement of the device to eject the clot from the apparatus.

Figures 9A, 9B, 9C, 9D, 9E, 9F, 9G:
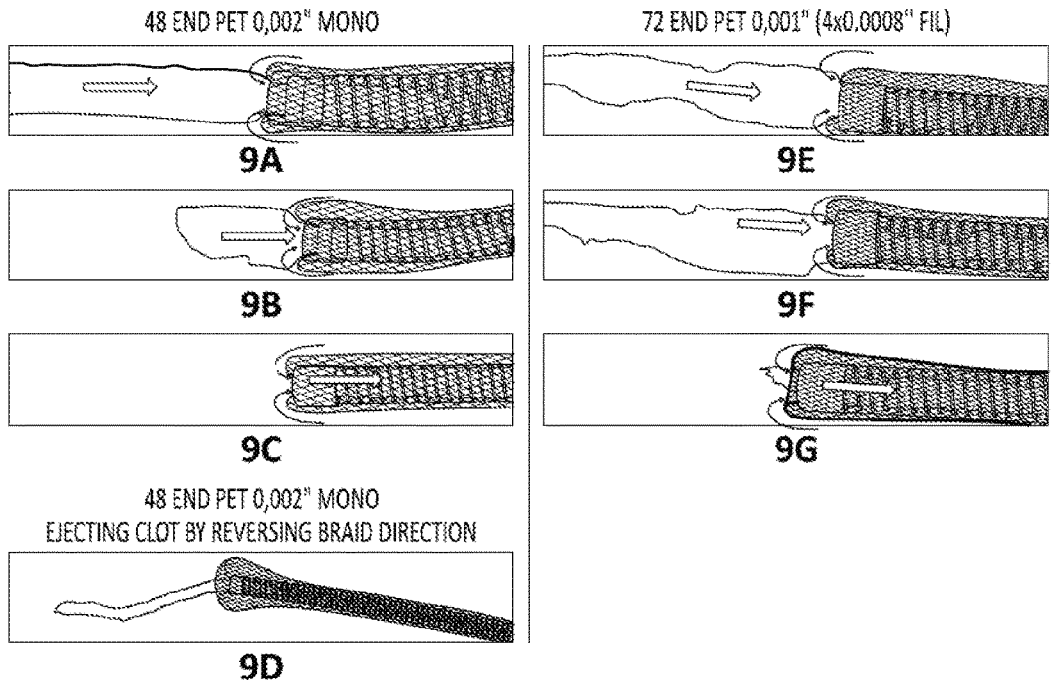
FIGS. 9A-9C illustrate operation of an apparatus having a 48-end PET (0.002" monofilament) tractor.
FIG. 9D illustrates reversing the apparatus of FIGS. 9A-9C.
FIGS. 9E-9G illustrate operation of an apparatus having a 72-end PET (0.002" 4×0.0008" filament) tractor drawing in a clot.

Similarly, FIGS. 9A-9C illustrate using a 48-end 0.002" PET monofilament braided tractor capturing a clot in a vessel. FIG. 9D shows reversing of the same apparatus to eject the clot. FIGS. 9E-9G show another example of a braided tractor, comprising a 72-end 0.001" PET (4×0.0008" fil) material drawing clot into the device by rolling the tractor region into the catheter, as shown.

Figures 10A, 10B, 10C, 10D, 10E:
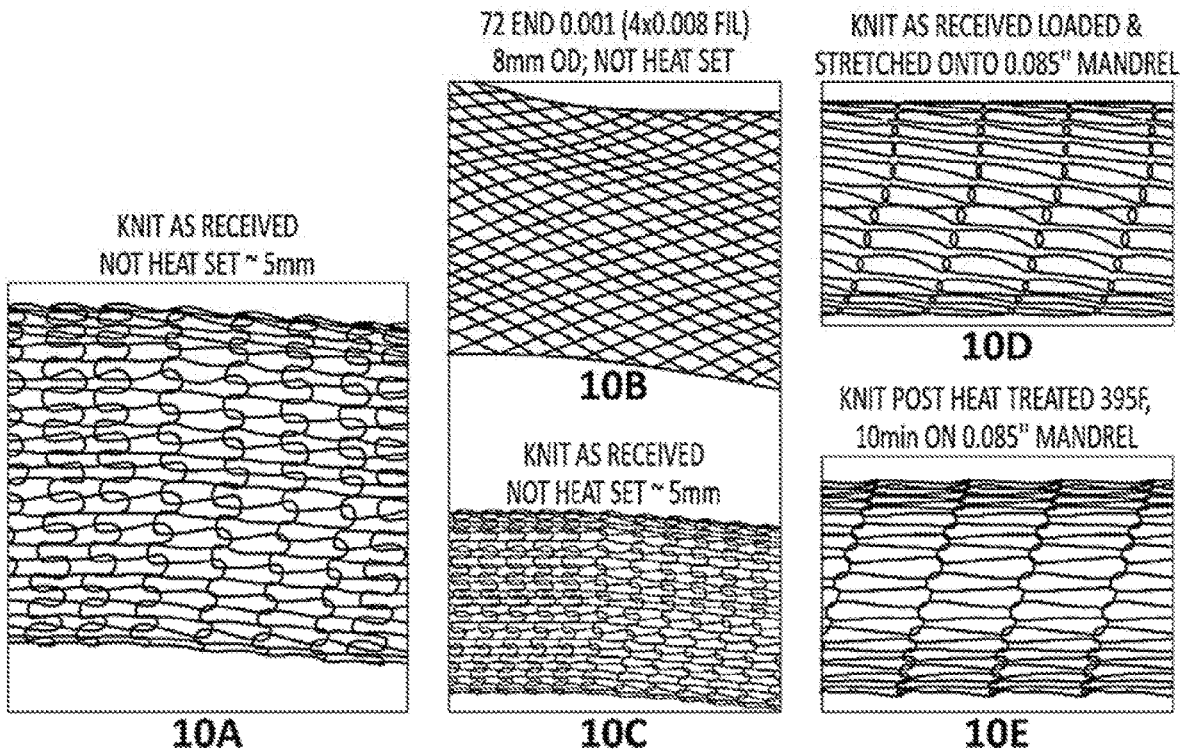
FIGS. 10A-10E illustrate examples of knitted tractors.

As discussed above, tractors may also be formed of a knitted material. A knitted material typically includes materials in which the same filament (or a series of filaments connected in tandem) is knitted to itself to form the tractor. It may be particularly advantageous to use a knit to form a tractor as described herein. For example, FIGS. 10A-10F illustrate an example of a 0.002" knitted tractor 26 needle (SN5923) material, which is a circular weft knit of 0.002" PET monofilament 26 needle head Greige (from Secant Medical). In FIGS. 10A-10C, the knit material is not heat set; the tractor regions shown in FIG. 10E is heat set, knot post-heat treated (at 395° F., 10 min on 0.085" mandrel).

Any of the apparatuses described herein may include a tractor region that is configured to grab a clot. In particular, described herein are apparatuses that may include a tractor region that has a plurality of projections extending from the tractor, particularly when the tractor rolls around the distal end of the catheter and inverts; these projections may help grab and/or macerate the clot.

For example, described herein are apparatuses including a plurality of projections that are formed as part of the tractor region. For example, any of these apparatuses may be configured to include projections that are formed by cutting (e.g., laser cutting) or forming from the tractor. Cutting and may be used to form projections or protrusions from a tube of material (or a sheet formed into a tube during processing) such as a sheet or tube of NiTi, thin-film NiTi, cobalt chromium, stainless steel, etc. Projections may be formed from a laser cut NiTi hypotube, a NiTi laser cut sheet, or the like. Projections may also be formed on any of these devices by welding. For example, projections may be formed by welding to a thin-film NiTi tube or sheet. The cut or formed tractor regions may be configured to have virtually any pattern or shape. For example a tractor region having projections that extend from an inverting/rolling tractor region may be formed of a metallic or polymeric material that can include any cut or shaped pattern so that the pattern lays flat (e.g., in the plane of the tractor) on outside of catheter and extend from the tractor (e.g., out of the plane of the tractor) as it rolls around the catheter. The projections may comprise portions of the tractor region pattern that extend and may grab and/or cut, e.g., macerate, the clot as they stick into the clot. These same regions of the tractor may then lie relatively flat against the ID of the catheter when fully inverted and pulled into the catheter.

In general, cut may be made in the tubes or sheets (e.g., sheets to be formed into tubes) in order to enhance flexibility, porosity and/or to add projections that may extend from the tractor as it is rolled over the distal end opening of a flexible tube (e.g., catheter). A tractor may therefore be formed into any appropriate pattern, so long as it is sufficiently flexible.

For example, FIGS. 11A-11D illustrate examples of patterns that may be used for a flexible tractor region. These two dimensional (2D) patterns (e.g., textured surfaces) may provide flexibility of the tractor region in rolling and inverting over the catheter distal end; in some variations, such patterns may help grab a clot when the tractor is rolled and pulled into catheter. These patterns or textures could be formed by laser cutting, molding of plastics or thin film metal (e.g., NiTi Technology), stamping, etching, or the like. The patterns shown in FIGS. 11A-11D generally form closed-cell shapes having angled arms forming the cell walls. The angles may allow deformation in one or more directions. The pattern may mimic the patterns of woven, braided and/or knitted materials, or may be different.

In any of the apparatuses described herein, the tractor region may also include surface micropatterns that may be added or formed onto the tractor. These micropatterns may help with grabbing a clot. For example, FIGS. 12A-12I illustrate micropatterns protrusions, projections, knobs, bumps, spikes, etc. that may extend from the surface of the tractor. In some variations, e.g., in FIGS. 12A-12C, 12E and 12F, the micropatterns may extend from the tractor region at all times, not just when rolling over the end of the catheter. Another example of an apparatus including a tractor having projections that extend from the tractor including the portion of the tractor that is over the catheter is shown in the apparatus of FIG. 14. In FIG. 15, the tractor 1401 includes a plurality of projections 1403 that extend from the tractor at all times, including the portion of the tractor that is rolling over the distal end opening of the catheter (the distal-facing tractor portion) as well as the portion that is over the outer diameter of the catheter, and within the inner diameter of the catheter. Other variations (e.g., FIG. 12D-12I, FIGS. 13A-13B, and 16A-16B) may project only from the portion of the tractor that is rolling over the distal end opening of the catheter.

Figure 11A:
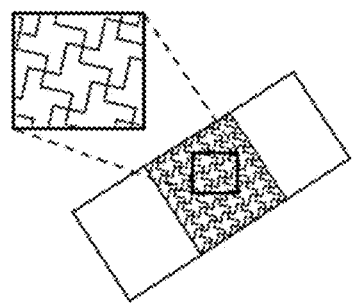
FIGS. 11A-11D illustrate patterns that may be used to form a tractor for a mechanical thrombectomy apparatus.
Figure 11B:
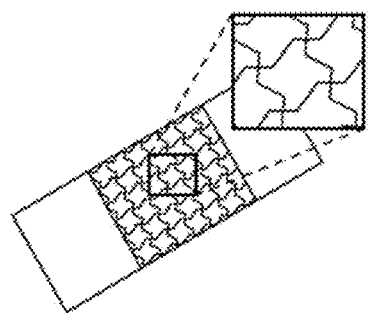
Figure 11C:
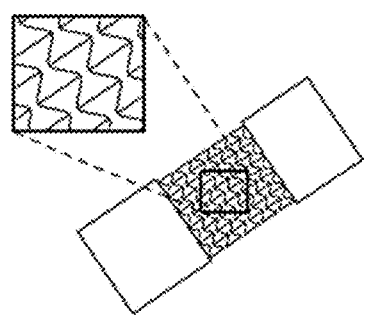
Figure 11D:
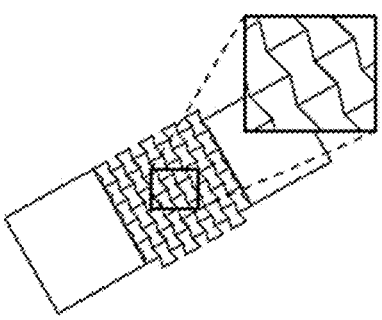
Figure 12A:
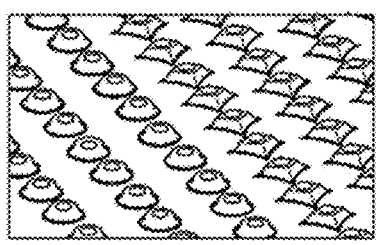
FIGS. 12A-12I show examples of microstructures that may be included in any of the mechanical thrombectomy apparatuses described herein.
Figure 12B:
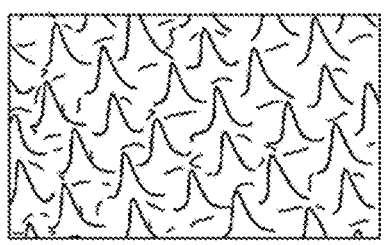
Figure 12C:
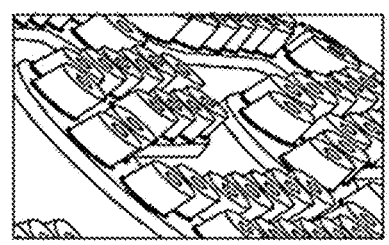
Figure 12D:
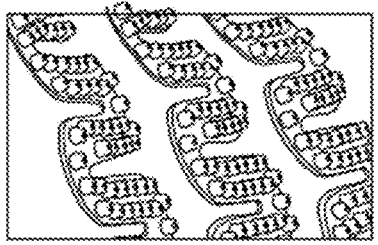
Figure 12E:
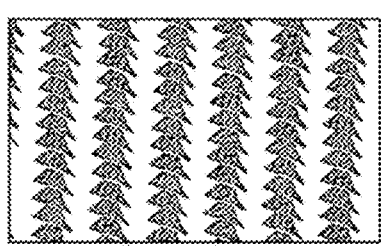
Figure 12F:
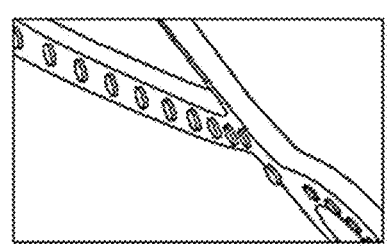
Figure 12G:
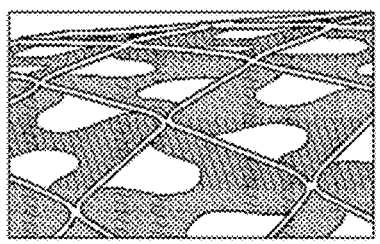
Figure 12H:
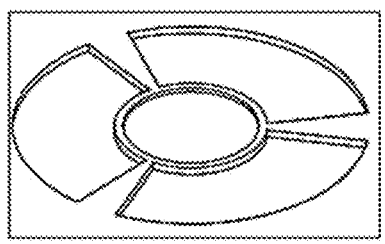
Figure 12I:
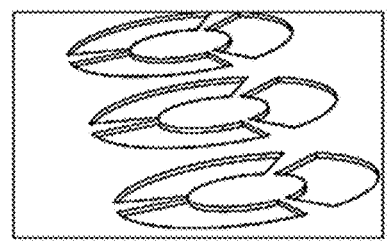
Figure 13A:
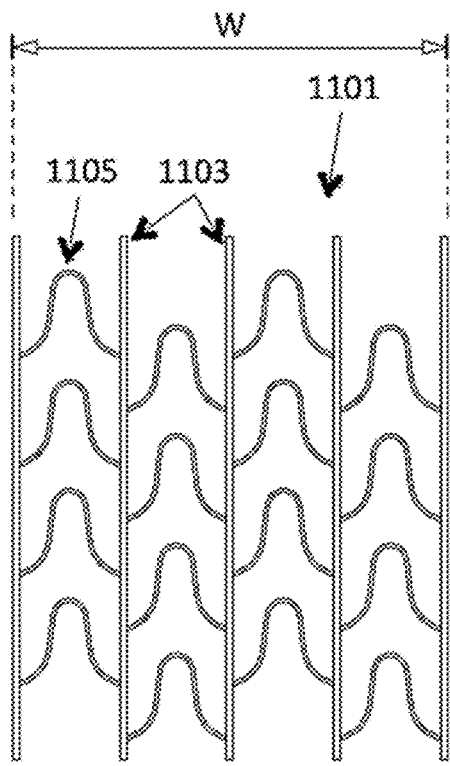
FIGS. 13A and 13B show side and cross-sectional views, respectively, illustrate an example of a tractor having selectively deployable projections that may extend from the inverting region of the tractor to assist in grabbing and/or macerating a clot.
Figure 13B:
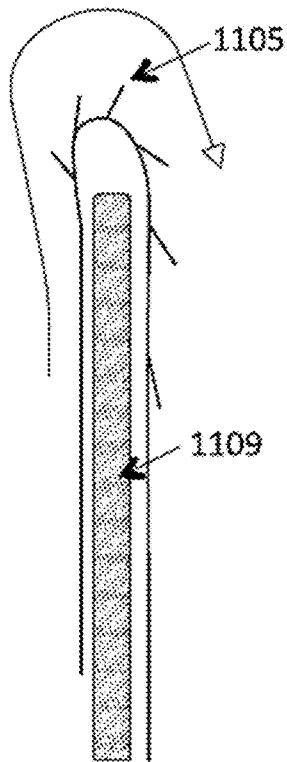
Figure 14:
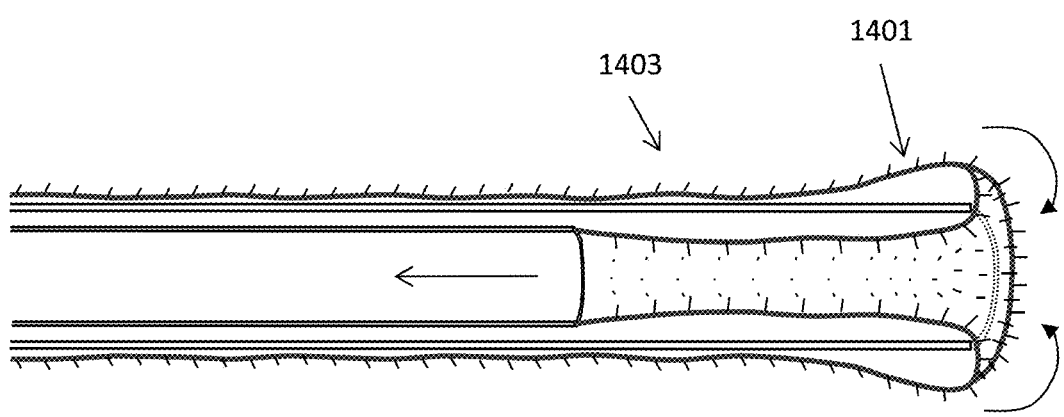
FIG. 14 illustrates an example of an apparatus including a plurality of projections extending from the tractor region that may aid in grabbing and/or macerating a clot.

For example, FIGS. 13A and 13B illustrate an example of a tractor region having a plurality of projections that extend from the portion of the surface of the tractor only when that portion of the tractor is inverting and rolling. FIG. 13B illustrates the extension of the projections 1105 from the tractor as the tractor is rolling over the distal catheter opening 1109 to invert. In this example, the tractor is a tubular structure 1101 having longitudinally arranged lengths of tractor material 1103 forming a backbone. Spanning between these flat, elongate regions 1103 are regions that extend between adjacent elongate regions first distally in the long axis, then back proximally. As the tractor rolls over the end of the catheter opening, e.g., as shown in cross-section in FIG. 13B, the loops of material 1105 extend out of the tractor (out of the plane of the tractor that is defined by the long axis of the tractor), and form projections 1105 that, as the tractor rolls over itself (inverting), extend outward, as shown in FIG. 11B. These projections may help grab a clot.

Projections formed in the tractor may be formed by cutting (e.g., laser cutting, press cutting, etc.), etching, etc., or they may be woven, braided or knitted into the tractor. For example when the tractor is formed of tube or sheet of material, the projections may be formed from the plane of the tractor material by removing material to leave a projection that may extend up and out of the material. When the tractor is not bending (e.g., inverting), the projections may have a low profile that does not substantially impact tracking of the tractor region when positioning the apparatus, e.g., moving it through a vessel in a patient's anatomy, while still enabling and enhancing rolling around the tip of the catheter. A projection that may help grab a clot may extend distally (e.g., towards the distal tip of the catheter when positioned on the outer catheter surface), so that as the tractor is rolled into the catheter, they extend distally (e.g., shown in FIG. 11B). Thus, the projections may create a grabbing effect. In some variations the projections may also cut into the clot and may macerate it. The projections may also help with catheter removal.

Figure 15A:
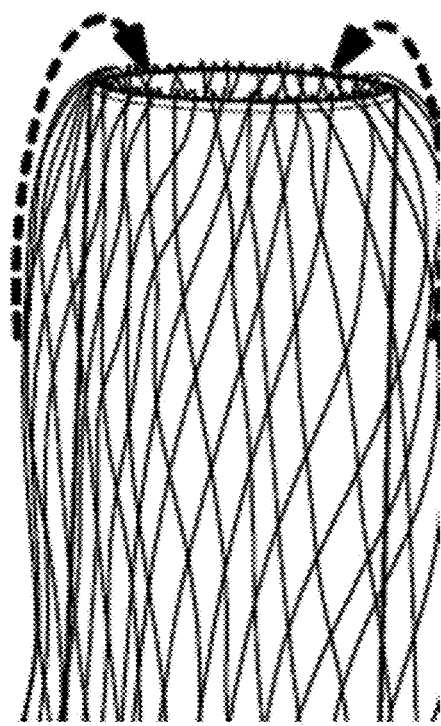
FIG. 15A shows an example of a distal end of a mechanical thrombectomy apparatus having a tractor formed from a plurality of filaments having a round cross-sectional profile; the tractor of FIG. 15A does not include any projections extending therefrom.
Figure 15B:
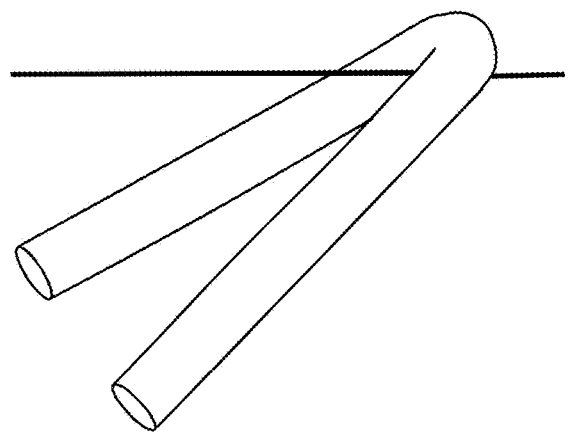
FIG. 15B illustrates the outer profile of a filament of the device of FIG. 15A as it inverts over a distal catheter opening of the elongate inversion support.
Figure 15C:
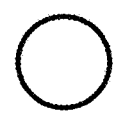
FIG. 15C illustrates the rounded profile of the filaments forming the tractor of FIG. 15A.

In some variations the tractor is a woven, braided or knitted tractor that may be formed of one or more strands that have one or more (e.g., 2, 3, 4, etc.) edges that may project from the plane of the tractor as it rolls over the distal end of the catheter. When the strand(s) forming the tractor have a rounded profile (see, e.g. FIG. 15C), as the tractor inverts over the catheter, the face of the inverting distal-facing tractor region remains smooth, as shown in FIG. 15A. FIG. 15B shows a single strand inverting over the distal end opening of a catheter.

Figure 15D:
FIG. 15D is a section through a rectangular filament (e.g., ribbon filament) having four edges.
Figure 15E:
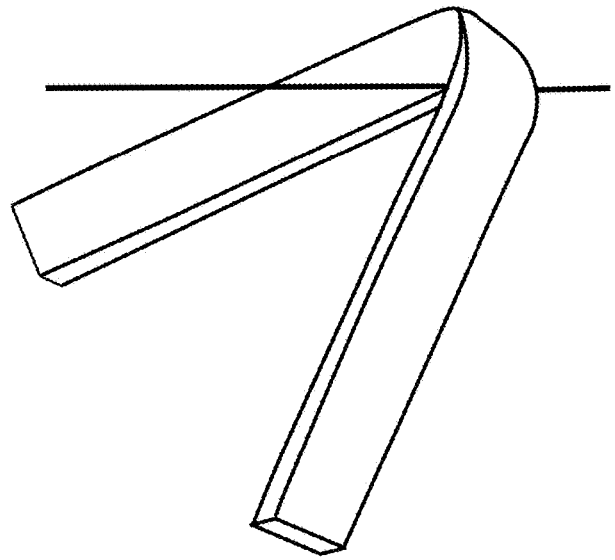
FIG. 15E illustrates the projection of a ribbon filament as it inverts over a catheter filament; because it approaches from an angle relative to the catheter opening (and because it is constrained by the adjacent filaments) the edge of the ribbon forming the inverting region may project up and out of the plane of the tractor.

If the strand forming the braided or woven tractor region is instead formed of a material having an edge (e.g., a ribbon, such as a ribbon having a rectangular profile, as shown in FIG. 15D), when the tractor rolls over the distal end opening of the catheter, particularly where the strand (e.g., ribbon) is at an angle relative to the distal end opening (and the distal-facing inverting portion of the tractor), as shown in FIG. 15E, the edge of the strand projects upwards and away from the tractor, out of the plane of the tractor. This is schematically shown in FIG. 15E, showing a rectangular strand or ribbon that may be woven, e.g., in a helical weave, and the edge 1505 of the woven strand twists up and out of the plane of the tractor as it inverts over the catheter to form a projection 1507 as shown in FIG. 15E. This projection may act as a scoop or shovel-like element that may help grab the clot, even if the tractor is lubricated and/or lubricious.

Figure 16A:
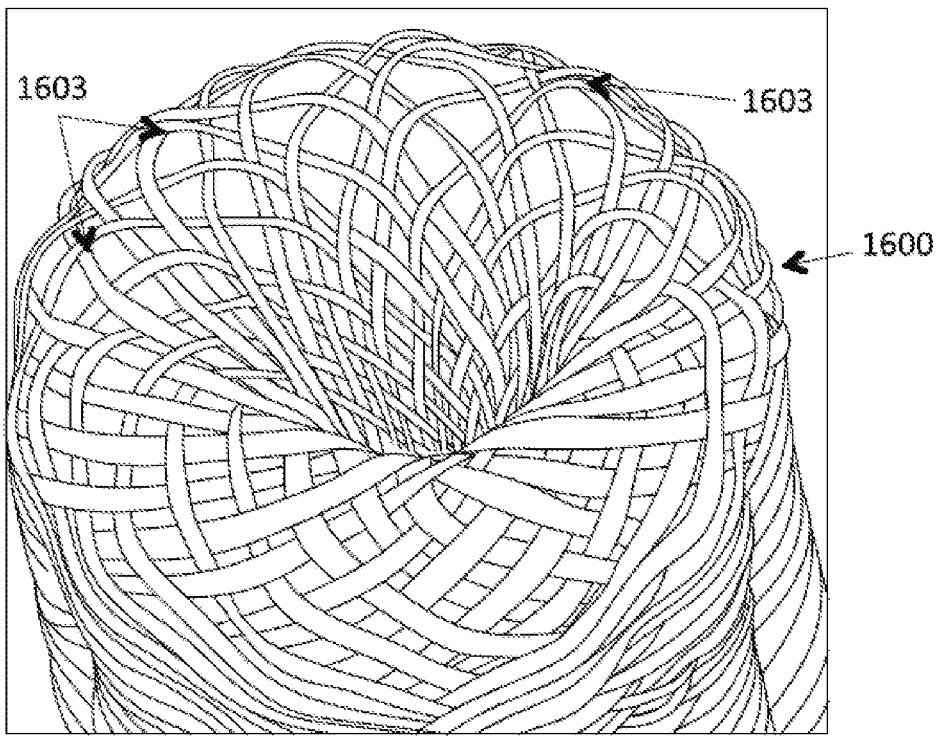
FIGS. 16A and 16B illustrate an example of a tractor having a plurality of projections formed by rectangular filaments (e.g., ribbon filaments) as schematically illustrated in FIGS. 15D-15E.
Figure 16B:
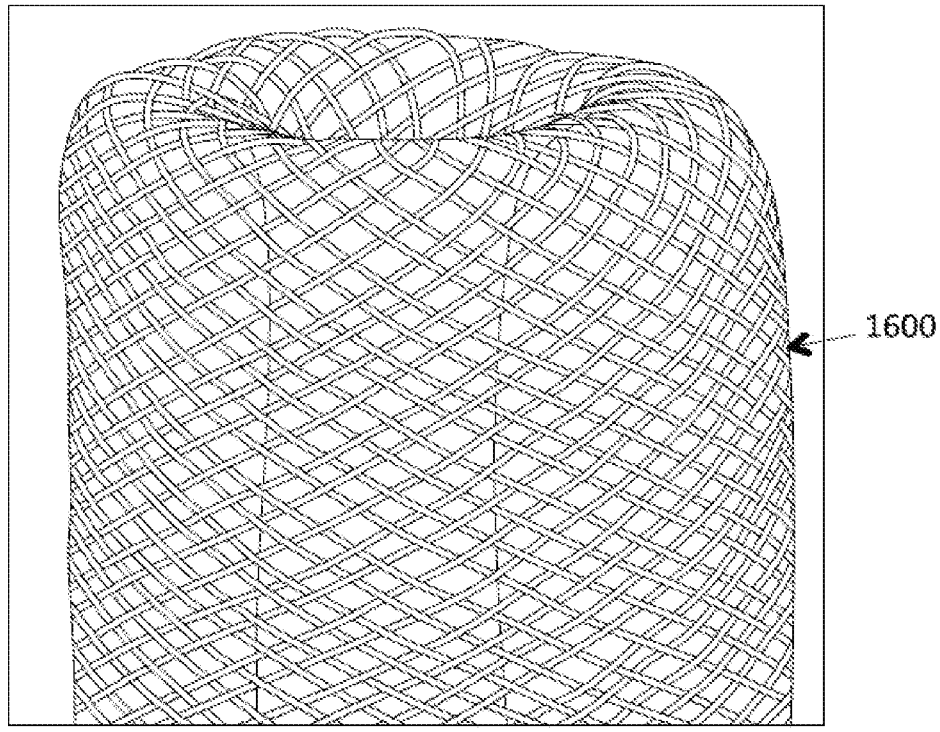

FIGS. 16A-16B illustrate an example of a tractor formed from a plurality of strands having an edge; shown here as strands that are ribbons having an edge (forming a rectangular profile).

In FIGS. 16A and 16B, the apparatus includes a catheter having a distal end and a distal end opening (not visible beneath the distal end-face of the tractor shown), and a tractor 1600 that includes a flexible tube that extends within the catheter, inverts over the distal end opening of the catheter and extends over the distal end of the catheter. The tractor forms a tubular wall and is configured to invert by rolling over the distal end opening of the catheter, as shown in FIG. 16A, when a first end of the tractor is pulled proximally within the catheter. The tractor includes a plurality of projections 1603 (in this example, formed by the edges of the ribbon-shaped strands, that extend from the distal-facing portion of the tractor as it is inverted over the distal end opening of the catheter. As the tractor rolls over the distal end opening of the catheter, the ribbon-shaped strands twist up and out 1603 of the tractor. These twisting edges form projections that can help grab a clot. Thus, FIG. 16A shows a distal end-face of the tractor inverting region as it rolls over the distal end opening of the catheter from the outer diameter to the inner diameter of the catheter. The plurality of projection regions 1603 are formed as the strands (ribbons) twist so that the edges of the strands extend up out of the plane of the tractor. As shown in FIG. 16B, when the tractor is over the outer diameter of the catheter, including the catheter distal end and more proximal regions, these strands do not project out of the tractor, but remain flush against the outer diameter, even when the catheter, and therefore the tractor, are bent and positioned in a tortious vessel; only when inverting do they project outward. Thus, the projections are not extended from the tractor in the portion of the tractor that extends over the distal end of the catheter. The center of this apparatus forms a guidewire lumen extending through the catheter and the tractor and may pass a guidewire. When the tractor is extended along the outer diameter of the catheter proximal to the inverting region, the strands, which are helically woven to form the tractor, remain flat, in the flat cylindrical surface ("plane") of the tractor.

As will be described in greater detail below, in some variations, including knitted tractor variations, the cells of the tractor may extend up and out of the inverting distal-facing region as it rolls around the catheter. These projections may also act as scoops, shovels, etc. and may help grab onto a clot.

Some variations of the tractors described herein may be formed of a non-woven, non-braided and non-knitted material. The tractor may be formed of a sheet and/or tube of material that may be directly fabricated (e.g., extrusion, etc.). This tractor may be cut, including laser cut, to form slots. In some variations these cuts may form projections. For example, the tractor may be formed of a solid (including porous) material into which a pattern is formed (e.g., slots, cut-out regions, etc.) including patterns that produce projections as described above. A tractor region may be formed of a tube of material into which slots or cut-out regions are formed. Such apparatuses may include a tractor formed from a tube of material such as ePTFE (which may be relatively soft, strong in tension and radial compression), NiTi (a super elastic and/or thermally settable material), a fabric (which may be a soft, thin walled material having a reasonably high radial/axial strength), or the like. The tractor may have material frictional properties and material surface hardness that are appropriate to grabbing a clot. In general, materials that are softer may be easier to track the apparatus in the anatomy. As mentioned, the tractor may have pores and may therefore have a tube porosity. The pores may be formed by removing material (or shaping into the openings) and may be oriented to aid in flexibility, rolling and/or tissue grabbing. A tube forming a tractor may be laser cut at an angle relative to axial length, or it may be laser cut (e.g., perpendicular versus angled relative to the tube thickness). Angled cuts may create a cutting surface to mince or macerate a clot, whereas perpendicular or rounded cuts through the thickness of the tractor may enhance grabbing of clot. Any of the tractors described herein may have a final shaped cross-section that is heat-set and/or formed on a mandrel (e.g., formed shape as set on heat treatment mandrel). The tractor regions described herein may be self-expanding. For example, in particular, the tractor may be set (e.g., as a shape-memory material) to expand outwards when inverted (e.g., within the catheter) and may therefore collapse inward slightly when inverted over the outside of the catheter. As discussed above in reference to FIGS. 2C and 3A-3C, this may aid in forming a trumpet shaped distal-facing region of the tractor, where the tractor is inverted over itself. Some variations of tractors may not be self-expanding. As mentioned, the tractor may be formed of a polymeric material (e.g., ePTFE, PET, PP, Nylon), metals (including alloys) or combinations of these. The tractor may have a low profile (e.g., minimum thickness), may be highly flexible and able to to navigate through tortuous vessels, may be able to invert around the catheter tip, may have clot grabbing properties (including projections and/or surface roughness) and may provide a column strength in compression (e.g., strut stiffness), and may be partially or completely radiopaque. The tractors described herein may scale from 1 mm OD fully formed to 15 mm. Any of these tractors may include a lubricious surface on one or both sides (particularly the side that faces outwards when extending over the outer diameter.

Examples of slotted laser cut tubes forming a tractor are provided herein, including those shown in FIGS. 17A-25B. The starting tubes may be flexible or rigid. For example, a soft flexible tube, strip, or roll of material such as ePTFE or a dense fabric (e.g., knit or weave or braid) may be used. Flexible tubes may provide tractors and/or combinations of tractors and catheters that allow tracking of the apparatus to the treatment site even in tortious vessels. Tracking allows pushing of the apparatus through tortuous vessels of small caliber over long distances from their introduction site to the human body, over length that can exceed 1 meter in some uses. A flexible tube (pre-laser cutting to form the tractor) may have a softness resulting in a low radial crush force, such as a micro-porous, polymer based tube. The tube may be processed (e.g., by cutting or any of the other techniques mentioned herein) to provide flexibility (e.g., the ability to pull the tractor into catheter, invert, and expand over catheter outer diameter) and/or to create a textured/porous surface that may aid in grabbing a clot (e.g., emboli) and may provide free spaces (voids) that may help store and/or masticate emboli, making them easier to store within the apparatus and transport. Prior to forming into the tractors the sheets or tubes (e.g., films, rolls, etc.) may have a smooth surface. Patterns may be formed into the sheet or tube to form the tractor. For example, laser slot patterns may be formed in the material to increase macro-surface roughness. Holes, slots, edges, divots, and bumps may be formed on the material. In addition to helping grab and hold emboli, such holes or slots may create free space in the tube wall to cut the clot and/or carry it away. The patterns used to form any of the tractors described herein may have a shorter strut length to strut width ratios. Short, wider struts may create tractors that are stiffer and may grab clot better. In combination with strut length to width, in some variations, thicker walls may be preferred. Thicker slotted walls may create stiffer struts and more aggressive surface texture to grab clots. Furthermore, thicker walls may enhance clot storage capacity within the slot gaps.

In some variations, it may be beneficial to provide slot designs which do not foreshorten. For example, if the slotted tube design is pulled axial (e.g., down its length), the tube diameter may not decrease. A decreasing diameter slotted tube may grab the outside of the catheter and cleat, increasing drag force when the tube is pulled.

In variations in which the initial tube or sheet of material used to form the tractor tube is relatively rigid (e.g., formed of a material such as Steel, Nitinol, Polyester, PTFE, Nylon, etc.), the initial tube stiffness/hardness may enhance the clot-grabbing ability when the tractor is slotted properly, to allow both increased flexibility, expansion and rolling. For example, a rigid tube may include slot designs that focuses in catheter tracking and creates a flexibly bending tractor with minimal foreshortening, that is able to be pulled into a catheter (inverting) structure. As with the more flexible starting tubes discussed above, tractors formed of more rigid starting materials may grab and transfer a clot, and the number of slots and/or voids may be increased to increase clot grabbing and/or carrying capacity. A slotted tube forming a tractor may include surface grabbing features, such as channels/corrugations (e.g. any of the microstructures such as those shown in FIGS. 12A-12I above. More rigid tubes may create harder or stiffer slotted tractors. For example, when struts are formed into the tractor (e.g., by cutting, etc.), the slot strut length to strut width may be greater than with less rigid starting materials, and may be a function of the rigid tubes elastic modulus. Higher elasticity materials (e.g., Niti, PET, PTFE) may have width length to width ratios from 10 to 100. Stiffer materials (e.g., steel, MP35N) may have a length to width ratio greater than 50. The wall thickness to strut width for elastic materials may be, for example, between 0.5 to 10; for stiffer materials it may be between 0.25 to 5.

As mentioned, any of the apparatuses described herein may include a tractor region that is non-foreshortening. The foreshortening of the tractor may depend at least in part on the slot designs for non-woven, non-braided, non-knitted designs (e.g., tractors that are not formed of a strand or strands of material). FIGS. 17A-17D illustrate an example of non-foreshortening design. Also, for both flexible and rigid starting tubes forming a non-woven tractor, the tube inner diameter can be slightly bigger then catheter tube outer diameter pre-slotting. Slotted tube designs which foreshorten may reach their smallest diameter limit when tensioned axially. If the tube is sized to be slightly larger than the catheter outer diameter, then it may jam (preventing any foreshortening) before it cleats to the catheter outer diameter. Tractor regions formed of an initially rigid material may grab clot more efficiently than tractors having an equivalent thickness but formed of a more flexible material. More flexible materials may deform as a function of stiffness.

Figure 17A:
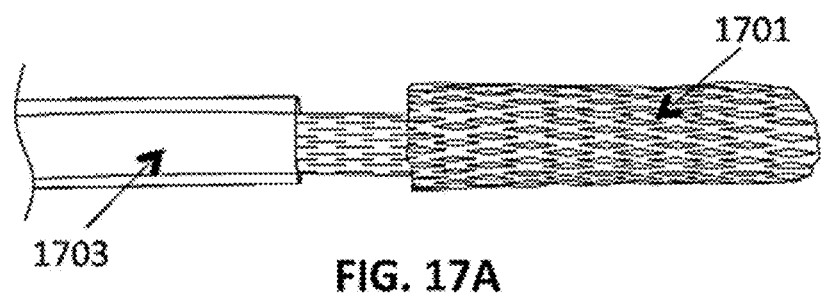
FIGS. 17A-17D illustrate exemplary tractors formed by cutting (e.g., laser cutting) a tubular material.

FIGS. 17A-17D illustrate an example of tractors that are formed by cutting slots and/or windows into tubes of material. In FIGS. 17A-17D, an initially soft material (e.g., ePTFE) was formed by a subtractive manufacturing technique to from, slots, pores and textures in the soft flexible tube. In FIGS. 17A-17D, a 3 mm ID ePTFE tube (configured to be used with a 2.9 mm OD catheter) was made to be highly flexible and have some level of column stiffness and radial/hoop stiffness by laser-cutting slot patterns into the tube wall to create textures and bend zones which impart clot grabbing and rolling. The ePTFE itself is highly lubricous. Addition of a lubricant (e.g., hydrophilic coating) may improve tracking and rolling. Lubricant can be applied to ID and OD or to either separately. FIG. 17A shows a first pattern 1701, having minimal cuts to create a smooth rolling of the tractor around the catheter 1703 portion of the apparatus.

Figure 17B:
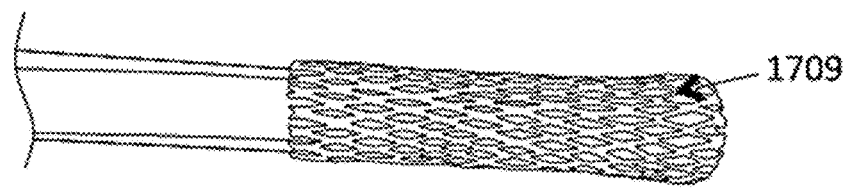

A second exemplary pattern is shown in FIG. 17B. In this example, the apparatus slightly larger cut-out regions 1709 (removed by laser cutting in this example), which may create better clot grabbing properties and more clot holding capacity. In FIG. 17B, the ePTFE tube forming the tractor region is slotted on the outside of the catheter. Note that the porosity (14 holes around the circumference) may help grab and hold colt. In both FIGS. 17A and 17B, the laser pattern may foreshorten, but may jam before it grips/cleats the catheter outer surface.

Another example of a tractor was made from a 2.9 mm OD ePTFE tube (configured for use with a 3 mm ID catheter). This example was made to be highly flexible and have some level of column stiffness and radial/hoop stiffness by laser-cutting slot patterns into the tube wall in a pattern to create textures and configured to include bend zones which impart clot grabbing and rolling. Similarly, a tractor may be made of, e.g., a 2.9 mm OD PET woven fabric tube (for use with a 3 mm ID catheter). The tractor may be formed of 30 Denier PET multi-filaments, 0.003" thickness. The resulting tractor may be configured to be soft and have some level of column stiffness and radial/hoop stiffness by laser cutting slot patterns into the tube wall in a patterns providing texture and bend zones which may impart clot grabbing and rolling. As with ePTFE, the PET material may itself be lubricous although additional lubricant may be added to improve tracking and rolling. Lubricant can be applied to ID and OD or to either separately.

An example of a tractor made from a somewhat rigid starting material was formed from a nickel titanium (NiTi) tube having a 3 mm OD (which may be used with, e.g., a 2.9 mm ID catheter). The wall thickness in these examples was between 0.001" and 0.002". Laser slot patterns were cut into the tube wall in various patterns to create textures and purpose-designed bend zones which may help impart clot grabbing and rolling. A lubricant may be applied, e.g., as a coating, to the ID and OD or to either separately. A first pattern similar to that shown in FIG. 17A was made by minimal laser cutting to create a smooth rolling tractor. The strut length to width ratio was between 25-50. A second pattern having larger slots/openings (similar to that shown in FIG. 17B) was formed by laser cutting. These patterns may foreshorten, but typically minimize or stop foreshortening before the tractor grips/cleats the catheter outer surface (which may result in jamming). The Niti design has the additional benefits of radiopacity, thermal shaping and super elasticity.

Any of these designs or patterns may for projections that may extend from the rolling distal-facing and inverting portion of the tractor, as discussed above. Such projection may be cut out as "teeth" or elongate members. The regions forming the projections may be sharp, e.g., pointy and/or cutting. Sharp projections may be chew and cut a mature clot. These projections regions may be short or long, may extend in one or more directions (e.g., forward or backward or bidirectional), and may be scoop-shaped (e.g., paddle-shaped). The number of projections may be selected based on the desired coarseness, e.g., the number of projections, the size (length/width/thickness), etc. The projections may change density down their length. For example, the laser pattern can be designed to allow tractor rolling (e.g., long struts) more easily initially, then have grabbing teeth at higher density; alternatively the tractor may be configured for greater initially grabbing, having a pattern with more and/or larger projections initially (distally) then transitioning to more slits (and flexibility) toward the proximal end, which may make it easier to pull. Further, the distribution of projections can be uniform around the tube perimeter and/or non-uniform (e.g., forming a spiral pattern, distributed in patches, having open areas, etc.).

Any of the tractors described herein may include a marker or makers (e.g., radiopaque markers, such as gold, Pt, etc.). When forming the tractor from a tube or sheet, the tubes may be be cut, then shaped to have any profile, such as straight, rolled over the tip, flaring at the proximal end, etc. Any of the microstructure described herein may be included or formed, as mentioned above, e.g., wells on the struts may help carry and grab clot. Tractors formed of tubes from which material was removed (or sheets formed into tubes) may be configured to have less cleating of the tractor onto the outer diameter of the clot, preventing jamming, particularly compared to woven or braided or knitted materials. However any of the slotted tube tractor configurations described herein may be used with, e.g., in combination with, a braid or knit or polymer sleeve, including either in parallel or in series. In general, any of these tractors may be formed as multi-layers, particular these slotted tube tractors.

For example, a tractor portion of an apparatus may be formed by removing material from a Niti tube that is slightly smaller than the inner diameter of the catheter that it will be used with, or it may be made from a tube that is slightly larger than the outer diameter of the catheters. The tube may be cut with a pattern that increase the coarseness of the outer surface (e.g., to include projections such as struts/scoops/teeth). For example a 0.001" tube wall thickness or smaller may be used.

Figure 17C:
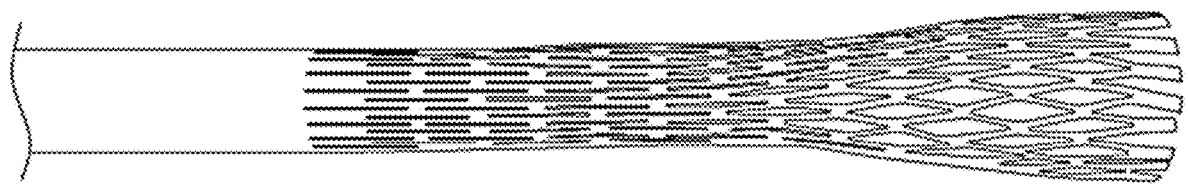
Figure 17D:
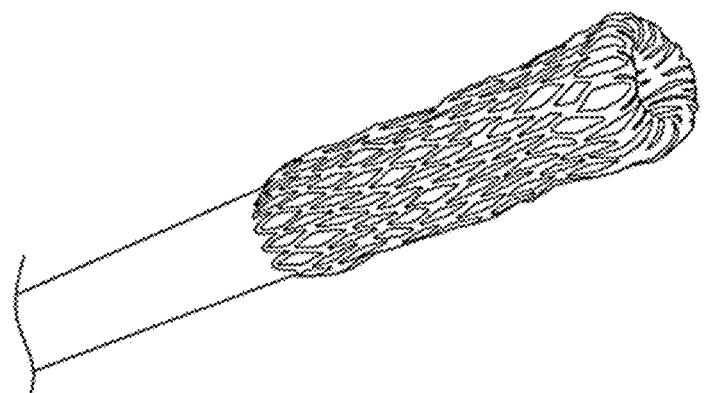

FIGS. 17C and 17D illustrate an example of a tractor region cut from paper. In FIG. 17C a rigid paper tube was cut to include slots and the distal end expanded, a shown. It may be inverted over itself and used as a tractor region. This paper prototype was prepared to illustrate the effectiveness of this pattern. Similarly, FIG. 17D is an example of a prototype tractor region.

Figure 18A:
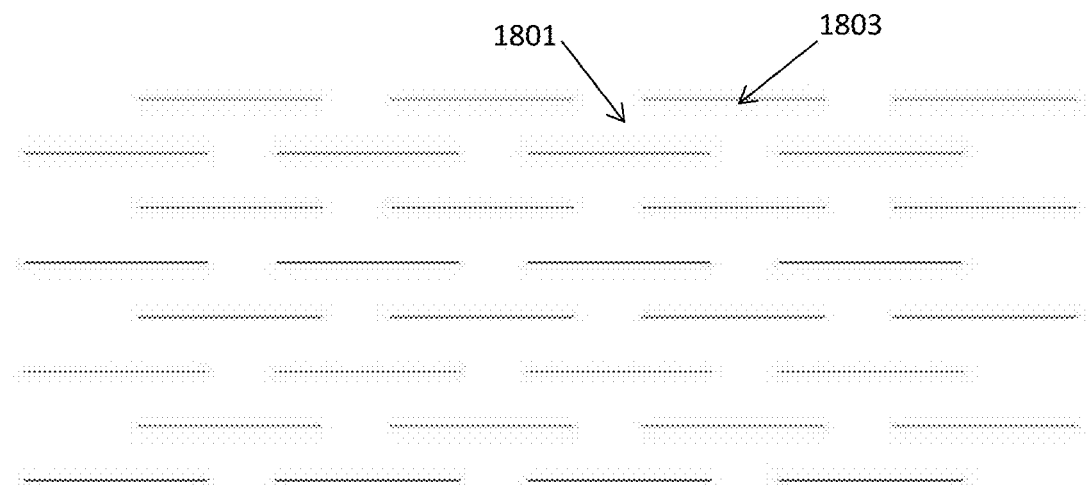
FIGS. 18A-18C illustrate different slotted patterns that may be cut into a tube (or sheet) to form a tractor region.
Figure 18B:
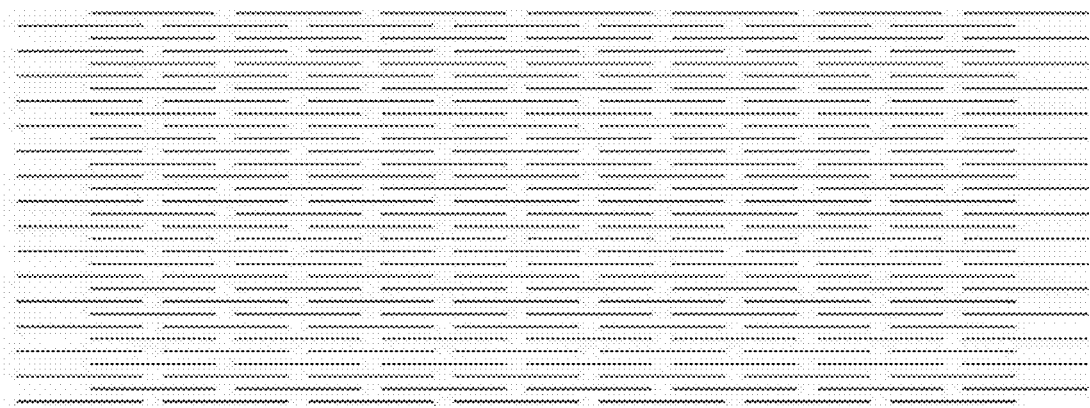
Figure 18C:
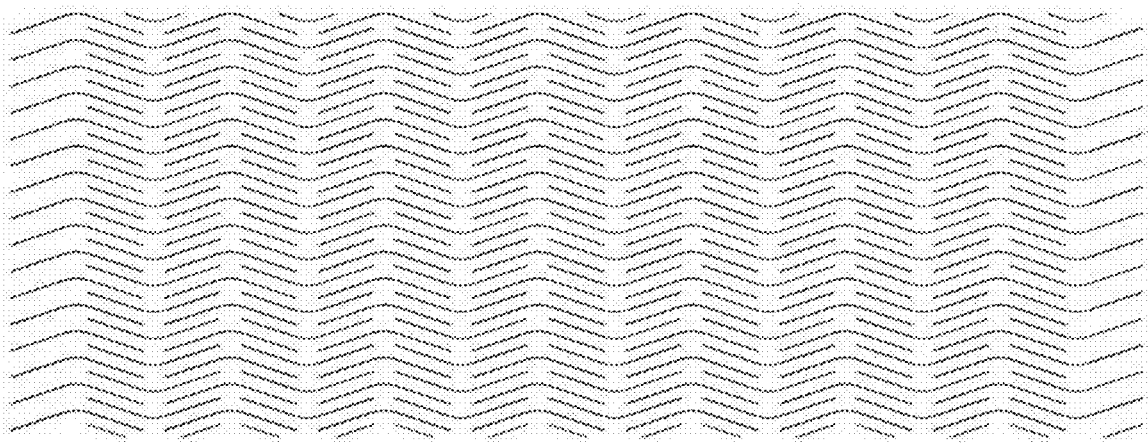

FIGS. 18A-18C illustrate examples of patterns that may be formed into a flat sheet or tubular member to form a tractor (e.g., slotted tractor). Similar to those shown in FIGS. 17A-17D. In FIG. 18A, the pattern may be cut to form the tractor. White regions 1801 may represent or form struts, while the lines indicate slots 1803 from which material is removed. This pattern is one of many resulting in a flexible tube having stout struts. FIG. 18B shows a similar example having a higher density of slots forming thinner struts and potentially higher porosity, which may result in a larger clot-carrying capacity. FIG. 18C illustrates an example of a pattern having curves that may produce a slightly more bendable (flexible in bending stiffness) slotted tractor. In FIGS. 18A-18C, the pattern is oriented so that the distal direction of the tractor formed by the pattern is at the right or left of the pattern shown (e.g., the tube is oriented right and left, relative to the figures, so that the tube is formed by rolling up from the bottom of the figure).

Figure 19:
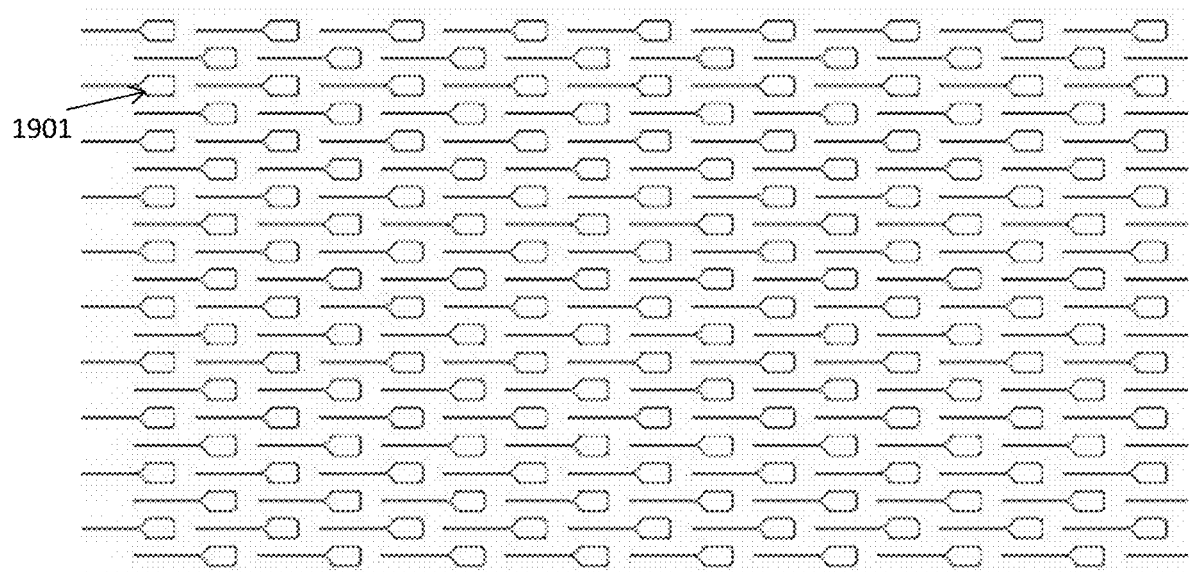
FIG. 19 is another example of a pattern that may be use to form a tractor region.
Figure 20A:
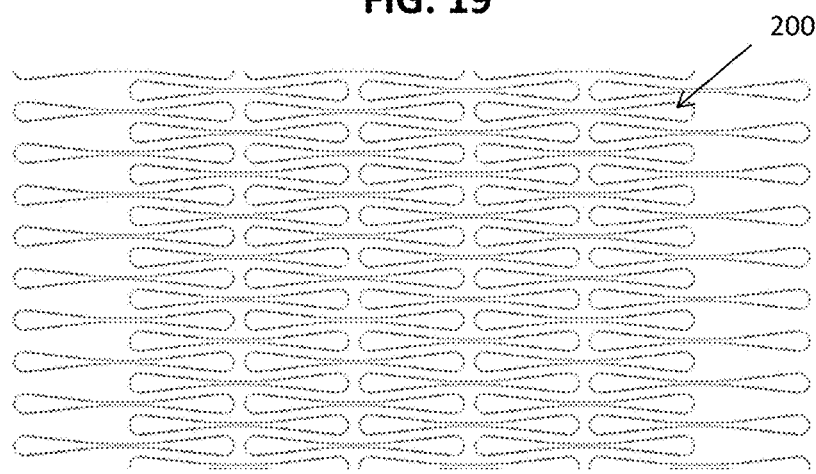
FIGS. 20A-20B show an example of a pattern that may be use to form a tractor region.
Figure 20B:
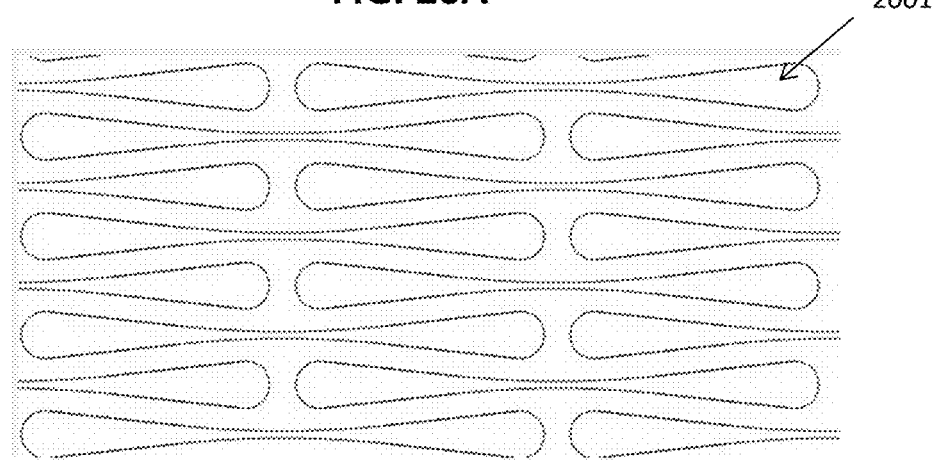

FIG. 19 is an example of a pattern that may be formed into a tube as part of a tractor having a plurality of both slots 1903 and cut-out regions 1901 (holes). Another example of a pattern having a plurality of cut-out holes 2001 formed into it is shown in FIGS. 20A and 20B. FIG. 20B shows an enlarged view.

An example of a pattern having a plurality of projections is shown in FIGS. 21A-24B. For example in FIGS. 21A and 21B, the pattern includes a plurality of slots 2101 and cut-out regions that leave a projecting strut or tooth 2105 behind. In these examples, the tooth 2105 is pointed and oriented to the left of the page, which may be the distal end direction of the tractor. (e.g., the left side of the image may correspond to the distal end of the tractor); thus when the pattern is formed into a tubular body to form the tractor, and the tractor is inverted over itself (e.g., rolling over the distal end opening of a catheter) the plurality of pointed projections 2105 may extend out of the tractor, and may help grab and draw clot into the catheter.

Figure 23A:
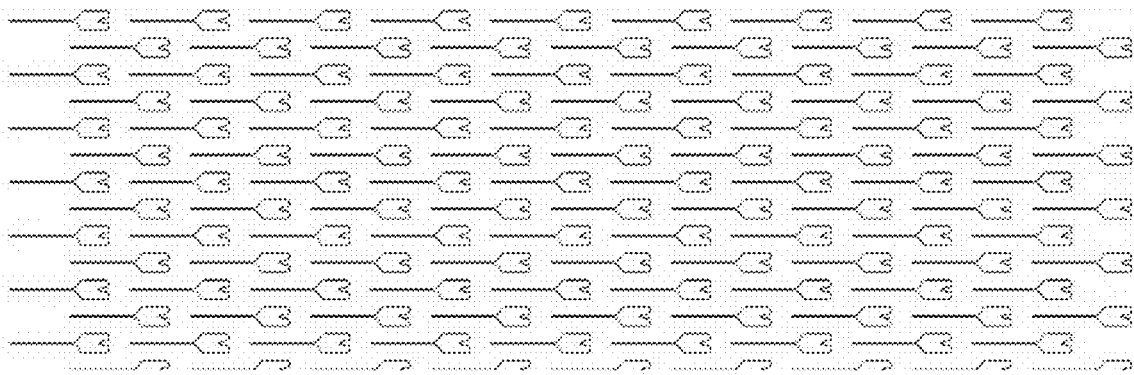
FIGS. 23A-23B show an example of a pattern that may be use to form a tractor region.
Figure 23B:
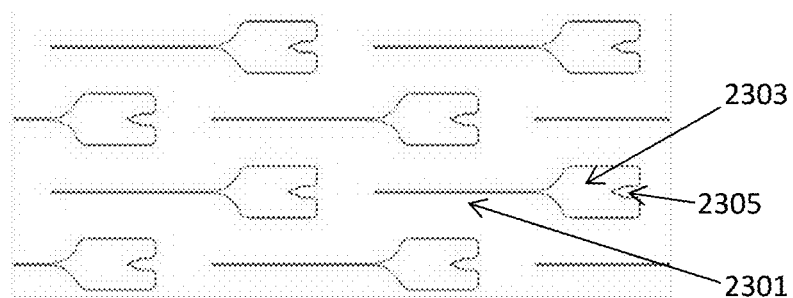
Figure 24A:
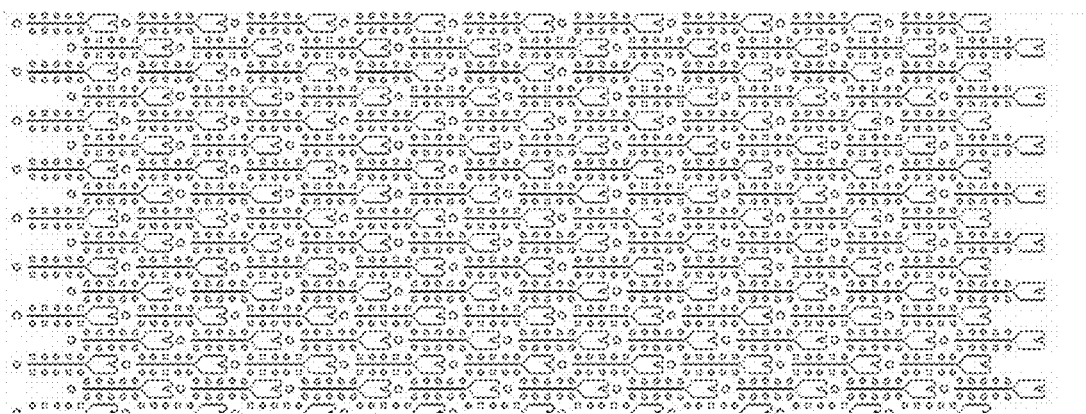
FIGS. 24A-24B show an example of a pattern that may be use to form a tractor region.
Figure 24B:
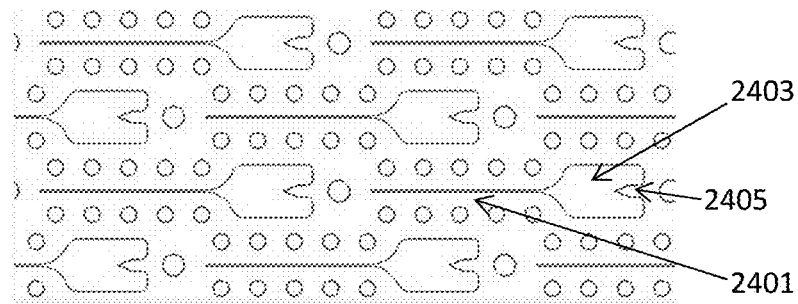

Similarly, the pattern shown in FIGS. 22A-22B illustrate another example include a slot 2201, a projection 2203 and a cut-out portion 2205. As in FIGS. 21A and 21B, the projection may extend out of the plane of the tubular tractor (shown here as the plane of the paper, even when rolled up to form the tractor region). FIG. 23A, and enlarged view of FIG. 24B, shows another example of a pattern for a tractor that is similar to that shown in FIG. 21A-21B, but with smaller projecting regions. In this example, the projections 2305 are sharp, and open into an opening 2303 connected to a slot 2301. The pattern shown in FIGS. 24A-24B is similar to that shown in FIG. 23A-23B but with additional openings (cut out regions 2407) which may increase the carrying capacity (e.g., clot carrying capacity) of the tractor region.

Figure 25A:
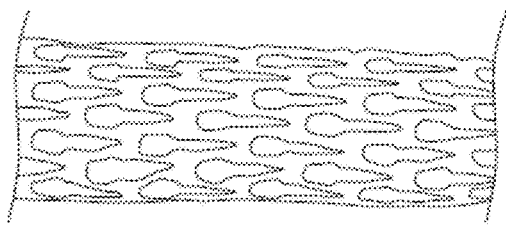
FIGS. 25A-25C illustrate tractor regions having different patterns of slots and openings.
Figure 25C:
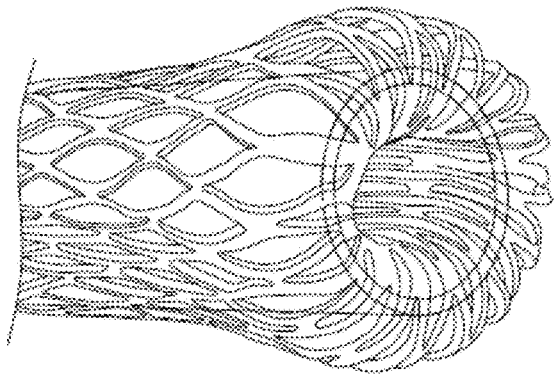
Figure 25B:
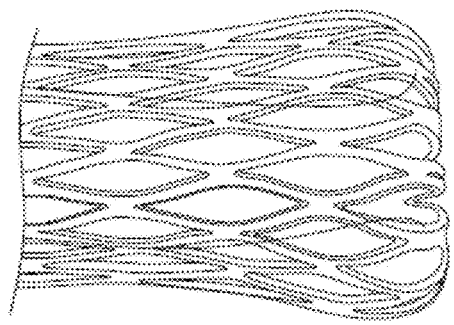

FIGS. 25A-25C are examples of laser-cut tube prototypes of tractor regions. In FIGS. 25B and 25C the tractor region is inverted over the distal end opening of the catheter.

In any of the tractor regions described herein, the tractor may have sufficient coarseness to grab the clot, yet still roll easily around catheter tip. Coarseness may relate to the thickness profile of the tractor region. For example, knitted tractors may be more course than braided tractors, due to the macro structure (e.g., cells, wire cross overs, shape of cells). The ability of the tractor to capture and transfer (like a conveyor) clot material through the catheter may be aided by coarser macro structures. In addition, as mentioned above, projections may both increase the coarseness and may help aid in grabbing clot. However, projections that extend only when inverting the tractor may be desirable; e.g., the tractor may feel smooth to the touch unless the dozer is rolled around a corner. The act of rolling the tractor may expose or activate the passive grabbing elements (projections). As mentioned, any of these apparatuses may include pores. For example, any of these apparatuses may include pores having a size that is greater than ⅕₀th of the catheter circumference. For example, the pore size may be 200 μm or greater (e.g., 300 μm or greater, 400 μm or greater, 500 μm or greater, etc.). In some variations the number pores (openings) per circumference may be between 5-20, 5-10, 10-15, 15-20, etc. pores on per catheter circumference on the tractor. As mentioned, the projections may be sharp, or dull, or may have an enlarged surface area (e.g., paddle-shaped). Sharp strut edges may grab and/or cut clots, while projections may also help grab clot. For example, a tractor may have a texture/roughness of at 0.0005" or greater (e.g., 0.0001"-0.0010"). The tractor may be formed of an inherently lubricious material, and/or may be lubricated through the use of hydrophilic coating on the tractor and/or OD of aspiration catheter or construction of lubricious hydrophobic materials such as Polyethylene, Polypropylene, fluoropolymers, FEP, PTFE.

Tractors Having Alternating Stiffness

Also described herein are tractors having alternating stiffness along their length. For example, a mechanical thrombectomy apparatus for removing a clot from a vessel may include a elongate inversion support including a catheter and having a distal end and a distal end opening and a tractor that is configured as a flexible tube that extends longitudinally within the catheter and doubles back over the distal end of the catheter to extend over the distal end of the catheter. The tractor may be formed of longitudinally alternating regions of higher and lower stiffness, wherein the regions of higher stiffness have a stiffness that is greater than the regions of lower stiffness. In some variations this may allow the lower stiffness regions to act as hinge-regions relative to the stiffer regions, when the tractor is pulled into the catheter. These variations may result in a seesawing motion at the distal end opening of the catheter, as the tractor is inverted and pulled into the catheter. This is illustrated schematically in FIGS. 30A-30D. For example, a portion of a length of tractor may include more stiff regions 3001 and less stiff regions 3003 that are alternating along the long axis of the tractor, as shown schematically in FIG. 30A. As the tractor region is inverted over the distal opening of the catheter (shown in FIG. 30B, in which a portion of the catheter wall is shown 3009), pulling the tractor over the wall 3009 causes the more flexible portions to bend over the wall, while the less flexible regions 3001 bend less or not at all. FIGS. 30B-30D illustrate progression of a tractor portion over the distal end opening, showing the bending of the less stiff/more flexible regions 3003 over the wall, while the more stiff/less flexible regions 3001 do not bend. The result is that, as shown by the arrows on the bottom, the diameter of the distal-facing region changes, and oscillates, as the tractor is pulled into the catheter.

Thus, the tractor may be configured so that it rolls around the catheter tip opening an inverts in a ratcheting fashion, in which parts of the tractor that are stiffer than other sections alternate with more stiff regions. These differently-stiff sections may cause the tractor rolling around the catheter tip to move in a semi-rigid manor and/or a pivoting/seesawing motion around the distal face of the catheter opening and the regions adjacent to the distal opening.

Tractors having alternating stiff/less stiff regions down the length of the catheter (including arranged in a helical manner spiraling down the length) may be formed in a variety of different manners, including constructing braids, laser cut tubes, knits, weaves, and laminates. For example, FIGS. 31A-31D illustrate an example of a knitted tractor region having this configuration. As the the variable stiffness tractor rolls around the catheter, sections of the tractor may temporarily dive to towards the center of the catheter ID, which may also aid in grabbing clot or a foreign body to pull into the catheter. The apparatus may be configured so that the tractor includes sections that sea-saw around the catheter tip so the dozer protrudes into the catheter ID by a distal equivalent to 5%, 10,%, 15%, 20%, 25%, 30%, 40%, 50%, 70%, 80%, 90% of the catheter's inner radius length, or any range of the numbers.

The tractor shown in FIG. 31A is a knit construct which has sections that are stiffer alternating with others sections that are less stiff. A first region 2401 of FIG. 31A, is stiffer than the adjacent second region 2403, which is also adjacent to another stiffer region 2401'; the stiffer/less stiff regions alternate and spiral in a helix along the length of the tractor. As the knit tractor shown in FIG. 31A rolls around the catheter, the less stiff section 2403 of the knit shown may temporarily bend, diving the stiffer region 2401 towards the center of the catheter inner diameter in a seesawing motion. FIG. 21B shows a side view of an apparatus including a knit tractor such as shown in FIG. 31A, having alternating stiff/less stiff regions extending down the length of the tractor. FIG. 31C illustrates the distal-facing and inverting tractor that is rolling (in a seesawing manner) over the distal end opening in the catheter. FIGS. 31D and 31E show alternative side and end views, respectively, of a mechanical thrombectomy apparatus including a tractor region such as is shown in FIG. 31A.

In this example, when the tractor rolls over the distal end opening of the catheter, the alternating stiff/less stiff construction causes the stiffer region to moves towards the center of the catheter, which may aid in grabbing clot or a foreign body to pull into the catheter. The tractor may therefore seesaw around the catheter tip opening so that the tractor protrudes into the catheter ID by a distal equivalent to 5%, 10,%, 15%, 20%, 25%, 30%, 40%, 50%, etc. of the catheter's inner radius length, before withdrawing, and then repeating the cycle.

Figures 32A, 32B, 32C, 32D:
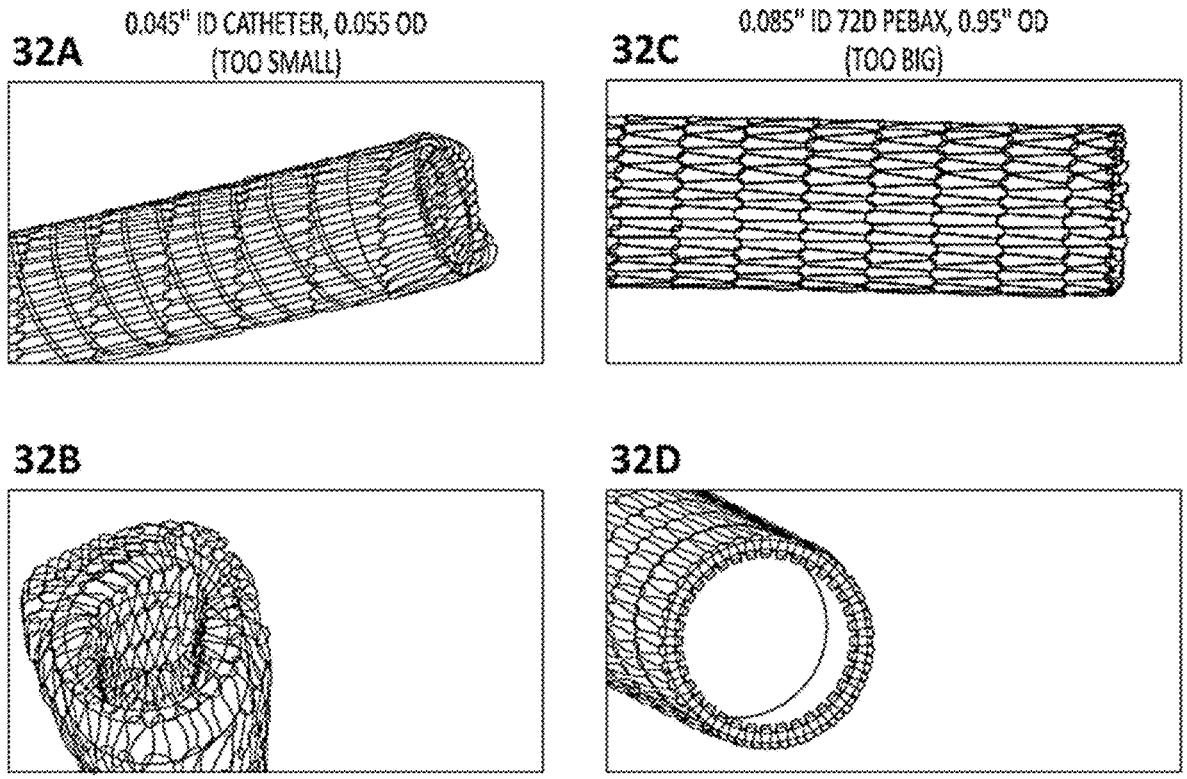
FIGS. 32A-32B illustrate jamming in an apparatus having a seesawing tractor region that has alternating stiff regions that are too long for the diameter of the catheter over which it is inverting.
FIGS. 32C-32D illustrate jamming in an apparatus having a seesawing tractor region that has alternating stiff regions that are too small for the catheter over which it is inverting.

The alternating stiff and less stiff regions may have a distance (e.g., axial distance, along the long axis of the tractor) that is related to the inner diameter of the catheter. In particular, if the stiff regions are too large relative to the catheter inner diameter, then the tractor may jam in the catheter, as illustrated in FIGS. 32A and 32B. In FIGS. 32A and 32B, for example, the stiff regions are greater than half the diameter of the inner diameter of the catheter. As shown in FIG. 32B, pulling the tractor into the catheter results in locking or jamming the tractor in the end of the catheter. In some variations the stiff region may be slightly larger than half the diameter without jamming, for example, if the adjacent stiff and less stiff regions wind around the tractor at a sufficiently large angle (e.g., greater than 10 degrees, 15 degrees, 20 degrees, etc.) so that only a subset of the stiff regions moving into the inner diameter of the catheter at the same time. Thus, the length of the stiffer regions may be 0.7 times the diameter of the catheter ID or less (e.g., 0.65 times, 0.6 times, 0.55 times, 0.5 time, 0.45 times, 0.4 times, etc., the diameter of the catheter ID or less). This may also be expressed the length of the stiff region being 1.3 times the radius of the catheter ID or less (e.g., 1.2 times, 1.1 times, 1.0 times, 0.9 times, 0.8 times, etc. the radius of the catheter ID or less).

Similarly, if the length of the stiff regions is too small, it will not see-saw in any appreciable amount and may, in some variations, jam onto the end of the catheter, as illustrated in FIGS. 32C and 32D. In FIGS. 32C and 32D, the length of the stiffer alternating regions is not substantially larger than the thickness of the catheter (e.g., the distance between the ID and OD of the catheter), so that no seesawing motion will occur. For example, the length of the stiff region may be 1.1 times or more than the thickness of the catheter (e.g., 1.2 times, 1.3 times, 1.4 times, 1.5 times, 1.6 times, 1.7 times, 1.8 times, 1.9 times, 2 times, etc. or more than the thickness of the catheter). Alternatively the length of the stiff regions maybe 0.1 times the radius of the catheter or greater (e.g., 0.2 times the radius of the catheter, 0.3 times the radius of the catheter, etc.).

In FIG. 32A-32B, the tractors formed of knit materials having different sizes post-heat treatment (e.g., 0.002" knit 26 needle (SN5923) heat treated on a 0.085" mandrel) than those shown in FIGS. 32C and 32D. In FIGS. 32A-32B, the knit material locked on and could not be rolled over the catheter. Relative to the size of the knit, the ID of the catheter (0.045" ID/0.055" OD) was too small. In contrast, in FIGS. 32C and 32D, the catheter dimensions were too large for the knit (e.g., 0.085" ID 72D Pebax, 0.95" OD); the knit material could not pull around and invert on the tubing of this size.

Figures 33A, 33B:
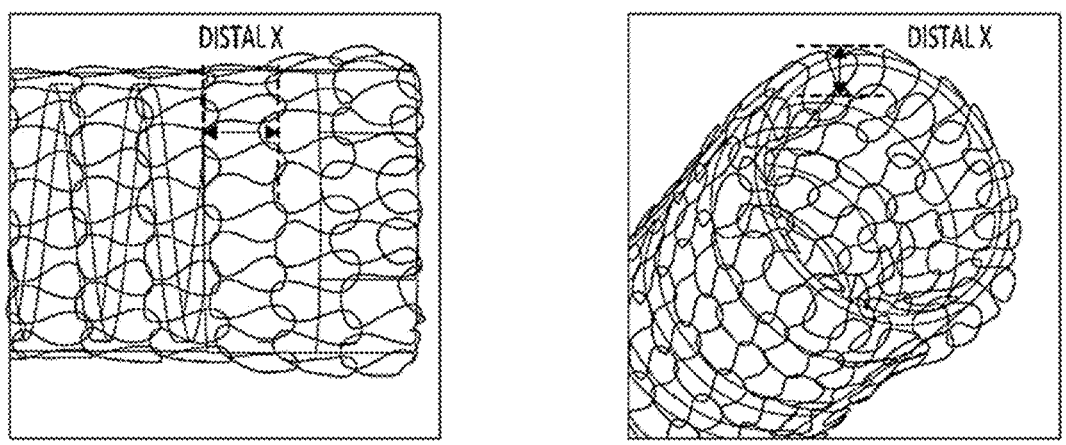
FIGS. 33A and 33B illustrate another example of an apparatus having a knitted tractor.
Figure 34:
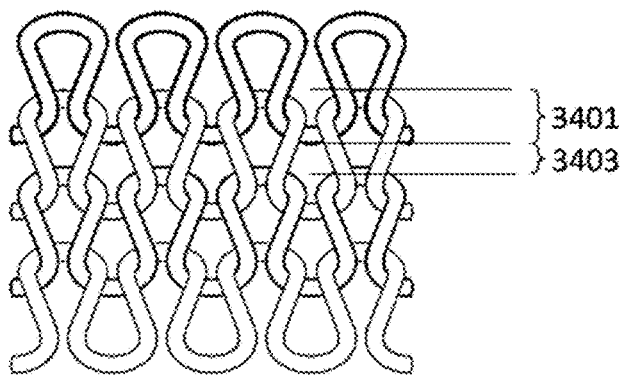
FIG. 34 is a schematic of a knitted tractor.
Figure 35A:
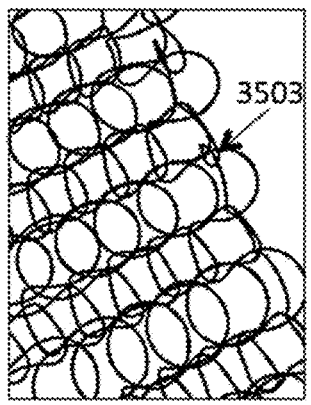
FIGS. 35A-35C illustrate movement of the loops of a knitted tractor having loops of a nickel titanium filament forming alternating stiff/less stiff regions (arranged down the long axis of the tractor).
Figure 35B:
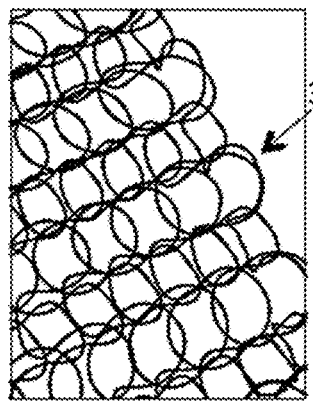
Figure 35C:
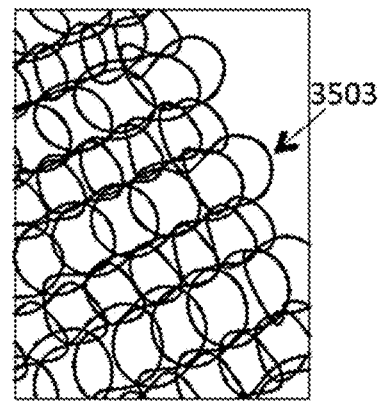
Figure 36A:
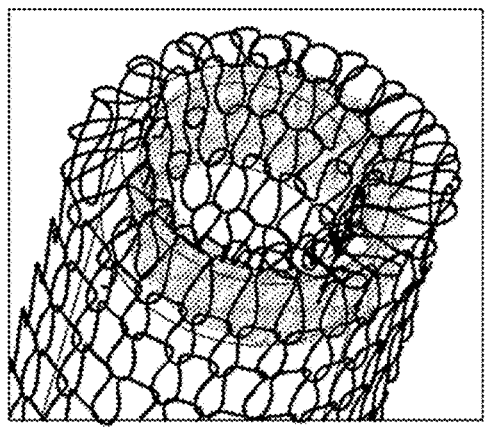
FIGS. 36A-36B illustrate end perspective and side perspective views, respectively, or an apparatus having a knitted tractor.
Figure 36B:
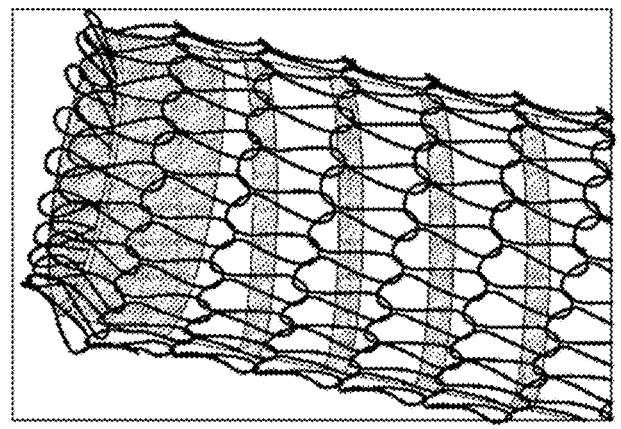
Figure 37A:
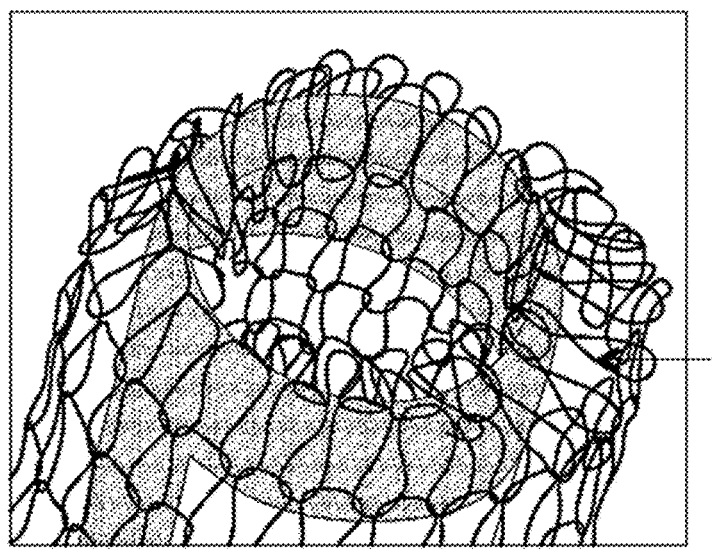
FIGS. 37A-37C illustrate seesawing operation of the apparatus of FIGS. 36A-36B.
Figure 37B:
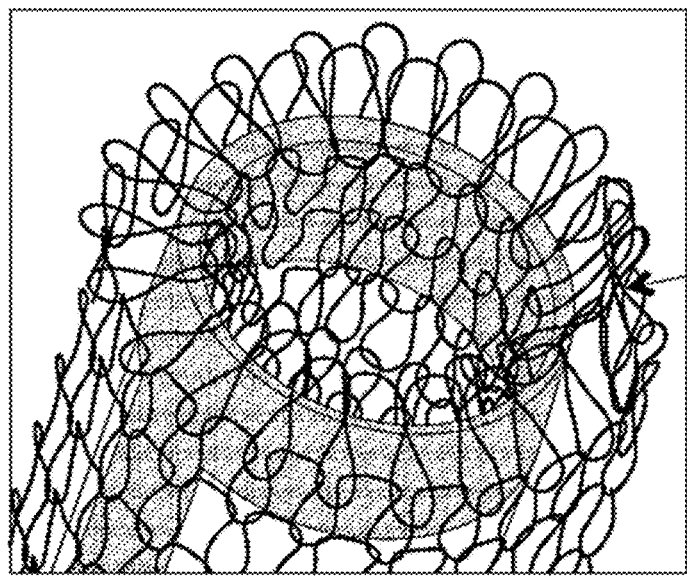
Figure 37C:
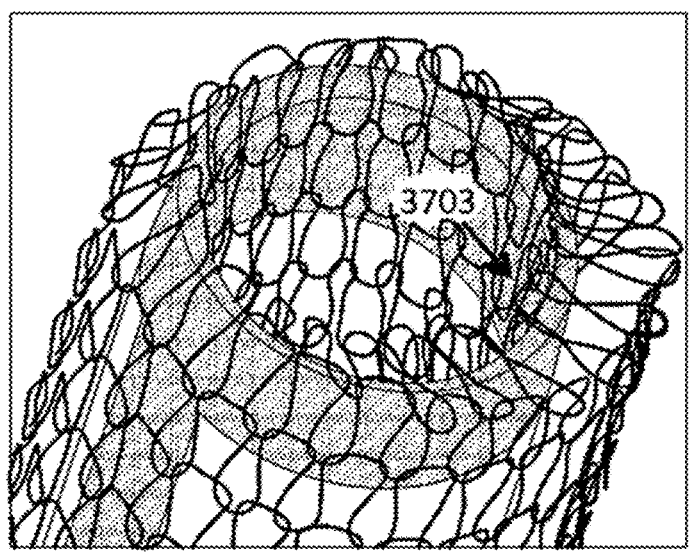

FIGS. 33A and 33B illustrate another example of a seesawing tractor formed from a knitted material. FIG. 34 shows an enlarged view of a portion of knitted material forming a tractor. The knitted tractor is formed from a filament (a monofilament or group of fibers collected into a filament) that is knitted to itself. The knit may be a tubular knitted material formed from a filament (monofilament or group of filaments) forming interlocking loops as shown in FIG. 34. In this example, the regions of overlap 3401 between the loops form the stiffer region, while the non-overlapping regions form the less stiff regions 3403. In any of the variations described herein, the loops formed by the knit may also act as protrusions as discussed above, and may aid in drawing the clot into the catheter and/or macerating the clot. For example, the sequence of illustrations in FIGS. 35A-35C show a portion of a knitted tractor having loops of nickel titanium forming alternating stiff/less stiff regions (arranged down the long axis of the tractor) as they roll in a seesawing manner over the distal end opening of the catheter. In this example, a single loop 3501 has been indicated showing it's progression from flush against the wall of the outer diameter of the catheter as the tractor is pulled into the catheter, until, as it approaches the distal opening of the catheter, it inverts by swinging the loop portion 3501 out of the plane of the tractor and up, where it may help grab clot material, as shown in FIGS. 35B-35C. The seesawing motion of a knitted tractor may also be seen in FIGS. 36A-36B and 37A-37C. An example of a mechanical thrombectomy apparatus is shown in FIGS. 36A-36B from end and side perspective views. FIGS. 37A-37C illustrate a method (e.g., that may be used for grabbing and removing a clot from a vessel) including pulling the distal end of the tractor (in this example, a knitted, seesawing tractor) proximally into the catheter. As shown in FIG. 37A the tractor may initially pull a stiff region 3703 towards the catheter opening. Because it is sufficiently stiff that it does not bend over the edge of the catheter, but is 'hinged to an adjacent stiff region, as the tractor is pulled proximally, the stiff region eventually tilts over the edge (in a seesawing motion), so that one end flips up away from the opening, as shown in FIG. 37B (stiff segment 3703 is indicated); finally it slides forward into the inner diameter of the catheter, as shown in FIG. 37C.

As discussed above, it may be desirable to have a tractor region that is sufficiently and/or selectively coarse so that it may grab a clot. In some variations a rougher tractor may grab clot despite the lubriciousness of the tractor. Knits may be generally more course than braids due to their macro structure (e.g., cells, wire cross overs, shape of cells). Knits may also have the desired porosity discussed above (e.g., having a porosity that permits the tractor to grab and store clot/clot carrying capacity). The size of the pores may be, e.g., between 5-20, 5-10, 10-15 or 15-20 pores on the tractor per circumference. The knit may be formed of any appropriate material, including, e.g., Nickle titanium (Niti) wire. For example, a knit may be formed of a PET monofilament, a PTFE monofilament, etc. A knitted tractor may also have a surface lubricity based on either material properties (e.g., metal, polymer, etc.) or added lubricant (inside, outside, both), and may be radiopaque (e.g., including an inter weave in Pt., DFT, over braid wires with Pt., etc.)

Patterned Tractors

Also described herein are tractors having a pattern of lubricious and/or non-lubricious regions on their outward-facing surfaces. These patterned regions may be coatings and/or surface modification, they may be formed by the material properties of the tractor, and/or they may be due to the application of a lubricious material (e.g., lubricant) in the pattern. A pattern of lubrication and/or non-lubricous material may assist in reducing friction while enhancing clot grabbing. A uniform lubricant (e.g., hydrophilic surface) on the outer-facing surface of the tractor has been found to reduce the ability of the tractor to grab a clot, particularly in the absence of other clot-grabbing features, such as the protrusions and edges discussed and illustrated above. Thus, described herein are patterns of lubricious and/or non-lubricous (including less lubricious, and tacky or adhesive) materials that may be included on the outward-facing surface of the tractor that may enhance pulling the tractor proximally into the device (e.g., the catheter of the elongate inversion support) and inverting the tractor, while still permitting or even enhancing clot grabbing.

Figure 40A:
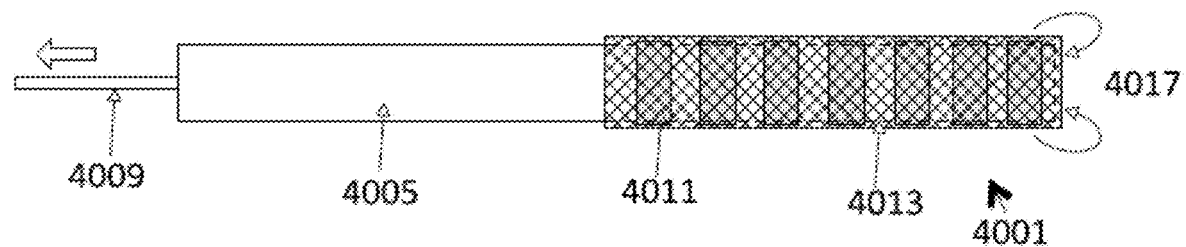
FIGS. 40A-40C illustrate apparatuses as described herein including patterned coatings (e.g., hydrophilic and/or hydrophobic coatings).
Figure 40B:
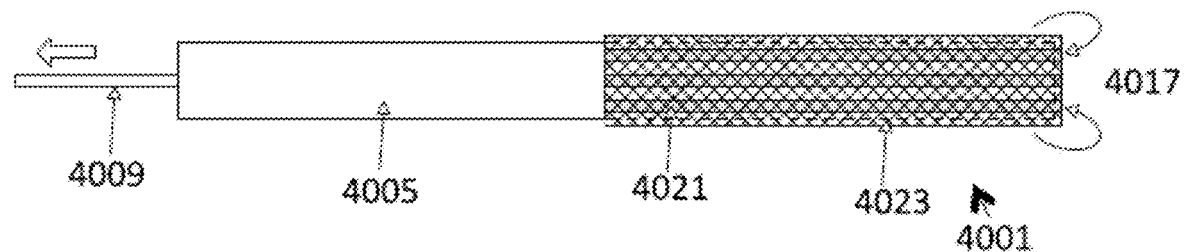
Figure 40C:
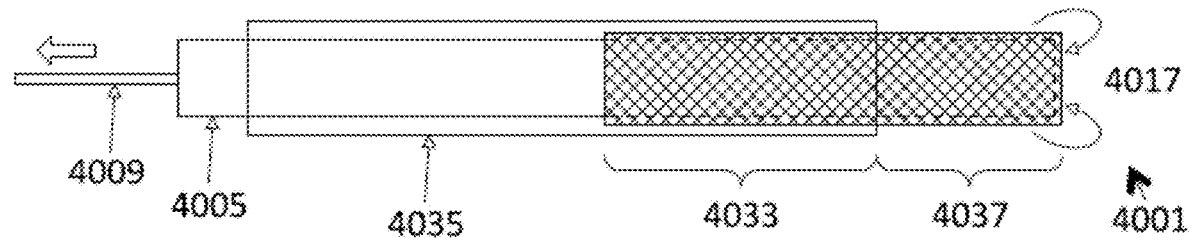

For example, any of the methods and apparatuses described herein may also include a pattern of non-uniform hydrophilic and/or hydrophobic coating (e.g., a patterned lubricious coating) that may assist with the positioning of the apparatus within the tortuous vessels before or during grabbing a clot. Even a partial hydrophilic coating (e.g., lubricious coating) on the outer-facing surface of the tractor element may reduce friction within the vessel ID. These lubricious regions (e.g., coatings) may be arranged in a pattern such as alternating regions (e.g., bands, stripes, checkerboard pattern, grid, spots, etc.). For example, it may be preferred to partially coat the tractor (e.g., braid) with a hydrophilic material such as using, e.g., a 5 mm coated length of braid followed by a 5 mm non-coated section. This coating may be in other patterns, as mentioned, including strips (longitudinal strips), a spiral pattern coating, a random pattern coating, etc. FIGS. 40A-40C illustrate examples of hydrophilic coating options.

For example, FIG. 40A shows an example of an apparatus including a tractor region and 4001 a catheter of an elongate inversion support 4005 into which the tractor is inverted and drawn proximally at the distal end of the tractor. The tractor 4001 may be attached to a puller 4009 (e.g., pull wire or pull catheter) to pull, or in any of these variations, push and pull, the tractor within the catheter from the distal end of the tractor. The proximal end of the tractor is attached over the outer surface (OD) of the outer catheter 4005. In FIGS. 40A-40C the tractor is shown as a braided tractor, but any of the tractor types (braided, woven, knitted, solid/cut-out, etc.) described herein may be configured to include a pattern of more/less lubricious regions.

The tractor shown in FIG. 40A includes a pattern of lubricious regions arranged in bands along the distal-to-proximal elongate length of the tractor. For example, regions coated with a lubricious material 4011 and uncoated (less lubricious or even sticky) regions 4013 alternate down the length of the tractor. Alternatively, the pattern may be formed of a grid or checkered pattern, a spiral/helical pattern along the length of the tractor, etc. As the tractor is drawn into the catheter and inverted 4017, the alternating lubricious/non-lubricious regions may help grab clot, which is particularly or only important when initially pulling the clot material into the inverting tractor and therefore the catheter.

FIG. 40B illustrates another example of a tractor 4001 in which elongate (in the long axis of the tractor) lengths of lubricious 4021 and non-lubricious 4023 regions alternate to form a stripe pattern down the length of the tractor. These "stripes" may be varying in size (e.g., diameter) and may be curved, zig-zag, wavy, etc.

In some variations, lubricious regions may be separated by non-lubricious regions by a minimum and/or maximum distance. For example the lubricous regions may be alternated with non-lubricous regions (including less lubricious and/or sticky/adhesive regions) by between 0.05 mm and 15 mm (e.g., by greater than at least: 0.005 mm, 0.01 mm, 0.02 mm, 0.03 mm, 0.04 mm, 0.05 mm, 0.06 mm, 0.07 mm, 0.08 mm, 0.09 mm, 0.1 mm 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, etc.). Similarly the maximum separation between lubricious regions may be less than about: 20 mm, 15 mm, 10 mm, 9 mm, 8 mm, 7 mm, 6 mm, 5 mm, etc.). The minimum and maximum distance may be determined based on the size of the tractor (e.g., diameter), and/or the rate at which the tractor is to be pulled. The minimum distance may also or alternatively be based on the lubriciousness of the coating. More highly lubricious materials may be separated by a greater minimum distance.

In some variations only a portion of the tractor is coated, either completely or in a pattern, and the proximal end portion (e.g., the last portion be drawn into the catheter) is not lubricious (e.g., uncoated or coated in a tacky/sticky material); the region distal to that (e.g., the region near the initial distal-facing inverting portion of the tractor is lubricious. Alternatively, the proximal end portion is lubricious (e.g., coated with a lubricious material) but the region distal to that (e.g., the region near the initial distal-facing inverting portion of the tractor) is uncoated or is tacky/sticky to help initially grab the clot.

For example, FIG. 40C shows an example of an apparatus including a sleeve 4035 or cover over the most proximal end of the tractor 4001. This sleeve may itself be lubricious on the outer-facing surface, and may protect or hold the tractor in position until it is drawn distally over the catheter, exposed, and inverted to grab/pull clot 4017. The proximal end of the tractor under the sleeve may be lubricious and/or non-lubricious (e.g., patterned) 4033. The region proximal to the inverting portion, and distal to the sleeve, 4037 may be lubricious or (preferably) non-lubricious and/or a pattern of non-lubricious and lubricous regions.

Elongate Inversion Supports

In general, the elongate inversion supports described herein may be or may include catheters that are operated with the tractor and are configured so that the tractor may invert over the distal end opening (aperture) of the elongate inversion support. Any appropriate elongate inversion support may be used and may be configured as a catheter (or micro catheter). Since the tractor region is pulled against the catheter to invert it, the catheter may be configured to have high compression resistance while maintaining superior tip bending (e.g., flexible tip) which may allow it to reach distal vessel segments within the human vasculature.

Small bore catheters including those for use herein may have braid reinforced segments combined with coil reinforcement. A braid may be used on the proximal end of the catheter to provide column stiffness and medium shaft flexibility, and coils are typically used distally to enhance flexibility while sacrificing column strength. The apparatuses described herein may use a catheter having a slotted tube distal segment element that, when activated, can create a significant axial column compression through the entire catheter shaft. Typically, this column compression may result in some catheter foreshortening and catheter bending (e.g., cork screwing). Described herein are catheters that may reduce this foreshortening and corkscrewing by leveraging slotted tube elements into the catheter distal segment (e.g., the last 8 cm or less).

Figures 26A, 26B, 26C:
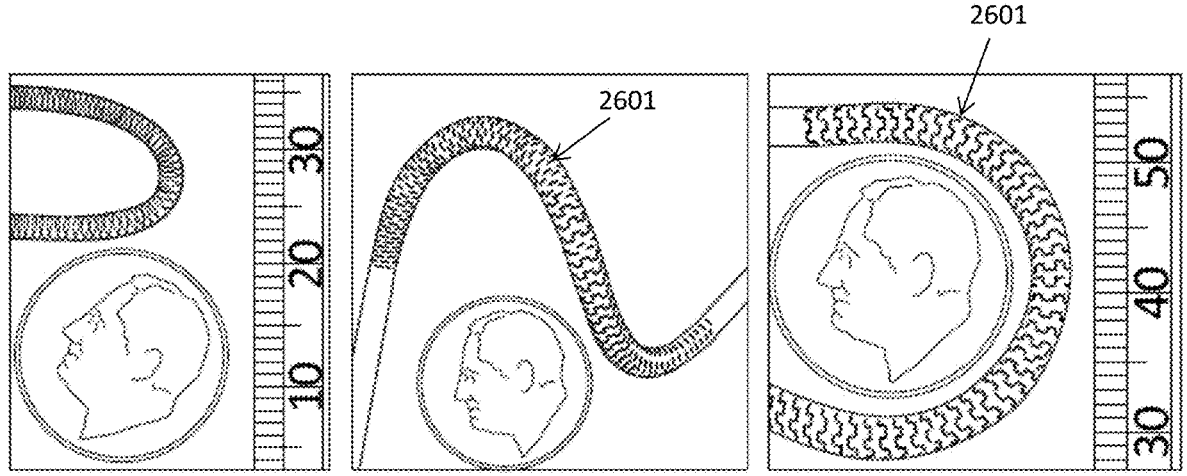
FIG. 26A illustrates bending of a typical small bore catheter distal tip.
FIGS. 26B-26C show examples of a catheter comprising a keyed slotted tube extending along the entire length of the catheter.

FIG. 26A illustrates bending of a typical small bore catheter distal tip. As seen in FIG. 21A, the catheter may bend around a small radius (as compared to the reference dime). The distal segment of this catheter may include a coil, and a low-durometer thin-walled polymer that is relatively soft, flexible and stretchy.

FIGS. 26B-26C illustrate, for comparison, a catheter comprising a keyed slotted tube extending along the entire length of the catheter. In this variation, the interlocking key segment 2601 of the design provides a axial stiffness when the structure sees compressive loads in the axial direction through the interlocking segments stacking or contacting a one or more point about its circumference. This structure still allows for adequate conformability around a tight radius allowing it to be push-able through a tortuous anatomy (ie neuro tortuous vessel). In order to increase bending flexibility and therefore the ability to make tighter turns, the keys may be shorter or longer and/or nested.

Figure 27:
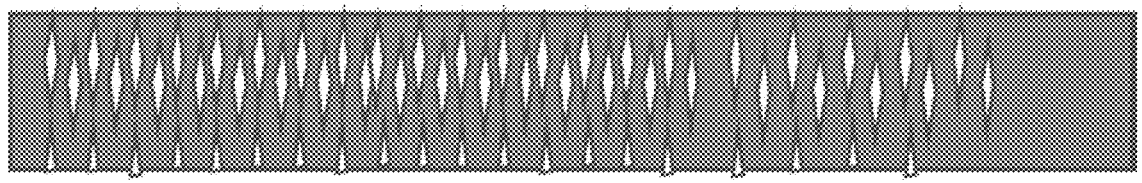
FIG. 27 shows an example of a catheter design formed as a slotted tube.

In general, the bending stiffness of the catheter is a function of the material, material composite structure, wall thickness, strut length, strut width, cell angle, strut shape, and cell length. FIG. 27 shows an example of a catheter design formed as a slotted tube. The tube includes cut-out regions that provide flexibility while leaving column strength.

Figure 28A:
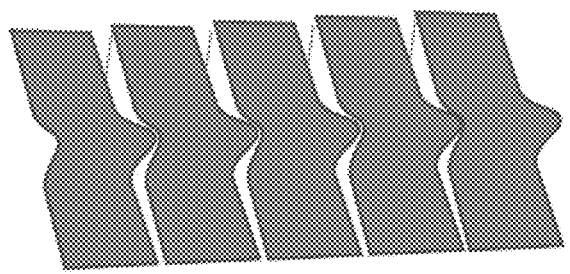
FIGS. 28A-28B is an example of a catheter design.
Figure 28B:
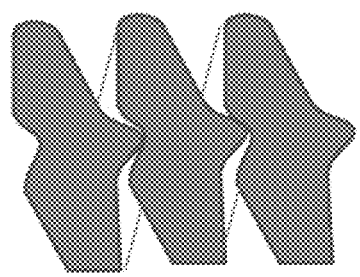

Another example of a catheter configured to have a high column strength and stiffness along its entire length is shown in FIGS. 28A-28B. In FIG. 28A, a hybrid laser-formed coil (spiral) has compaction-resistant features, along the entire continuous length of the catheter. The coil bending stiffness in this design is a function of the material, wall thickness, coil width, helix angle, hinge shape, hinge height, hinge location (e.g., linear axial or out of phase/helix), shape of coil surface and the catheter material stiffness.

Figure 29A:
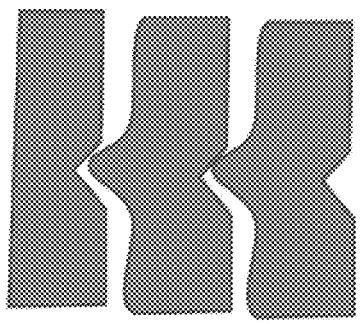
FIGS. 29A-29B is an example of a catheter design.
Figure 29B:
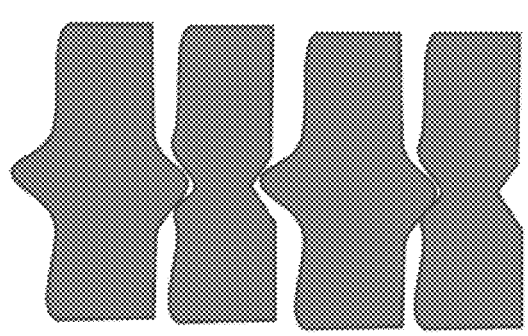

The catheter configuration shown in FIGS. 29A-28B illustrate variations in which individual hoop/ring segments are linked by a polymer wall of the catheter only. The ring bending stiffness is a function of the material, wall thickness, ring width, hinge shape, hinge height, hinge location (linear axial or out of phase/helix), shape of ring surface and the catheter material stiffness.

Any of the apparatuses described herein may include a catheters having a hard distal tip (e.g., formed of a PTFE, PEEK, stainless steel, etc.) and may be radiused to enhance rolling. The tip opening may be radiused from a middle of catheter wall, without an outer radius. Any of these catheters may include a lubricious coating. Finally, any of these catheters may also be configured to permit aspiration (e.g., drawing suction) through them, which may be helpful.

FIGS. 42A-43D, described in greater detail below, including examples of elongate inversion supports that may be used in any of the apparatuses described.

For example, any of the apparatuses described herein may include or be configure for use with a vacuum. The vacuum may aid in initially gasping or grabbing the thrombus. The vacuum may be applied from the distal end of the apparatus and/or of an intermediate or outer catheter or sleeve that is used with the apparatuses (e.g., elongate inversion support and inverting tractor) described herein. Also described herein are apparatuses that are adapted for use with a vacuum, including for use with an intermediate or outer catheter through which the apparatus may be delivered to the clot. The apparatus may grab clot from within the outer catheter, or it may be extended distally out of the intermediate or outer catheter.

FIG. 41A shows an example of a configuration in which an outer/intermediate catheter or sleeve that is highly flexible may be maneuvered, for example with a guidewire, to a distal end of the device. Thus, the intermediate catheter may be maneuvered near, or adjacent to, the thrombus. As in any of these methods of use described herein, imaging (such as fluoroscopy, contrast imaging, etc.) may be used. Once in positioned, the guidewire may be removed or left in place, and the apparatus including the elongate inversion support and inverting tractor may be extended within the intermediate catheter/sleeve. In FIG. 41A, the intermediate catheter 4104 is shown positioned within the vessel 4109 distally. As with any of the illustrations here, in the vessel maybe highly tortious and branching, although for convenience it is shown as straight in the figures. The apparatus 4100 is extended distally through the intermediate catheter, and extends out of the distal opening of the intermediate catheter to grab the clot 4111, as shown. The puller 4105 may thus be drawn proximally (to the left in the figure) to pull the tractor 4103 from over the catheter portion of the elongate inversion support 4113, so that it inverts and rolls into the lumen of the elongate inversion support, capturing and drawing the clot in with it. The clot may be compressed.

Thus, this configuration may be referred to as a vessel cleaner. In addition to the rolling of the tractor to grab and pull the clot, the clot may be pulled by a vacuum applied from one or both of the intermediate catheter 4121 and/or the elongate inversion support 4123. Vacuum may be applied, e.g., within the intermediate catheter, before the apparatus is positioned distally (or even within the intermediate catheter at all) or after it has been extended distally from the intermediate catheter. This configuration shown in FIG. 41A may introduce the tractor through outer catheter to the face of clot. As mentioned, the mechanical thrombectomy apparatus may be extended distally from the intermediate catheter either by pushing it out distally and/or by pulling back the intermediate catheter to deploy all or part of the tractor into vessel, as shown. If vacuum is applied through the catheter, the catheter forming the elongate inversion support may be jacketed or sealed to allow aspiration through this catheter.

Optionally pull vacuum through outer and/or inner and/or puller. As mentioned, thereafter the tractor may be pulled proximally relative to the the elongate inversion support to pull the clot. The intermediate catheter may then be advanced distally and/or the mechanical thrombectomy apparatus may be withdrawn proximally to remove the apparatus once the clot has been removed. Thereafter an angiogram may be taken to confirm that the clot has been removed.

Alternatively, in FIG. 41B, a clot may be removed using the intermediate catheter to draw a vacuum with the mechanical thrombectomy apparatus within the lumen (e.g., near the distal end, but not extending fully from the distal end) of the intermediate catheter. As described for FIG. 41A, in FIG. 41B the intermediate catheter may be inserted into the vessel (e.g., using a guidewire) so that the distal end is positioned near the clot. Suction may be used to draw the clot into the intermediate catheter either before the mechanical thrombectomy device is inserted or after it has been inserted.

In FIG. 41B, the elongate inversion support 4113' is particularly well suited for use with a vacuum applied through the intermediate catheter 4104 surrounding the apparatus. For example, in FIG. 41B, the elongate inversion support 4113' include a distal catheter region 4125 that extends just a few cm from the distal end opening in which the clot is drawn. The elongate inversion support then tapers down to an elongate support, which may be formed by a wire, hypotube or skived region. This configuration may prevent the catheter from blocking the lumen of the intermediate catheter and and therefore increasing the resistance of the vacuum before it can reach the open distal end and apply suction to drawn the clot. Alternatively or additionally, the outer diameter of the catheter portion of the elongate inversion support may be sized to allow more of the vacuum to pass. For example, the apparatus may be sized such that there is at least about 0.002 inches or greater (e.g., 0.003, 0.004, 0.005, 0.006, etc., inches) between the outer diameter of the catheter and the inner diameter of the intermediate catheter ("outer catheter"). This may also permit unimpeded rolling of the tractor over the distal end opening of the elongate inversion support.

In operation, the method of removing clot such as shown in FIG. 41B may include pulling at least the tip of a clot into the intermediate catheter through the use of a vacuum 4121. Typically the clot may clog within the intermediate catheter; the mechanical thrombectomy apparatuses described herein may be used to remove the clot from within the intermediate catheter. For example, while maintaining vacuum, the mechanical thrombectomy apparatus may be inserted (or it may be preloaded in intermediate catheter as mentioned) and the tractor puller 4105 may be pulled to pull the clot out of the intermediate catheter and the vessel, compress and/or macerate it and pull it into the apparatus and therefore the intermediate catheter, where it can be withdrawn proximally, e.g., by removing the mechanical thrombectomy apparatus. As mentioned, an angiogram may be taken through intermediate catheter (e.g., leaving it in place in case the mechanical thrombectomy apparatus needs to be re-inserted and used to remove more clot) to confirm clot has been removed.

Figure 42A:
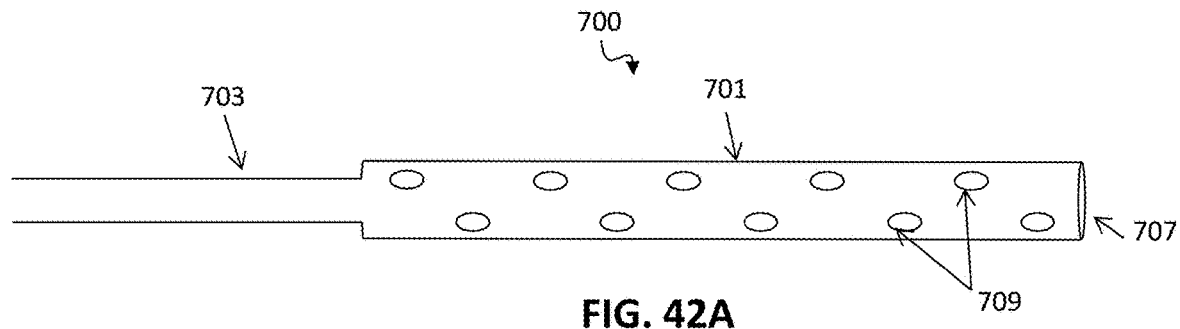
FIGS. 42A-42B illustrate a variation of a catheter of an elongate inversion support having both different diameters (e.g., a larger-diameter distal catheter connected to a smaller-diameter proximal region extending longitudinally in the proximal-to-distal axis), and a plurality of openings (e.g., cut-out regions, holes, etc.).
Figure 42B:
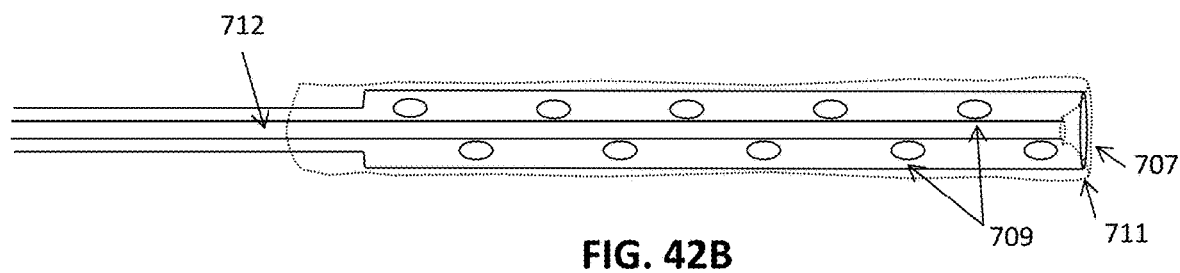

As mentioned, a full catheter such as shown in FIG. 41A may block or prevent the vacuum from reaching the distal end of the intermediate vessel. Therefore it may be beneficial to adapt the mechanical thrombectomy apparatus so that it can be used with vacuum within an intermediate catheter or sleeve, as shown in FIG. 41B. This may be achieved as mentioned above, by minimizing the larger-diameter catheter portion of the elongate inversion support forming the distal end opening over which the tractor inverts. In FIG. 42A for example, the elongate inversion support 700 has a distal catheter portion 701 having a larger diameter than the more proximal region 703, and also includes a plurality of openings, holes, gaps, cut-out regions, slots, etc. 709 that may allow the flow of vacuum through the elongate inversion support more easily. The elongate inversion support shown also includes a distal end 707 into which a tractor 711 inverts, as shown in FIG. 42B. IN FIG. 42B, the elongate inversion support is shown transparent so that the puller 713 and tractor within the elongate inversion support is visible.

Figure 42C:
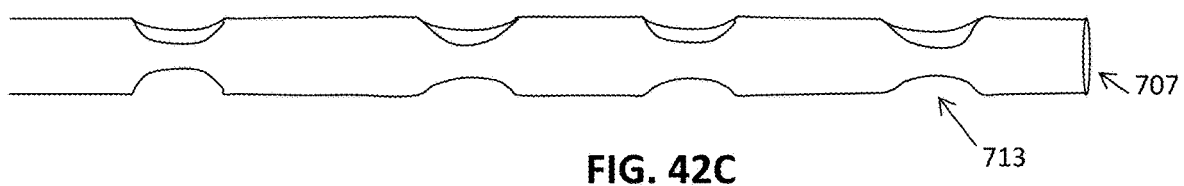
FIGS. 42C-42D illustrate another variation of a catheter of an elongate inversion support having a plurality of opening formed therethrough.
Figure 42D:
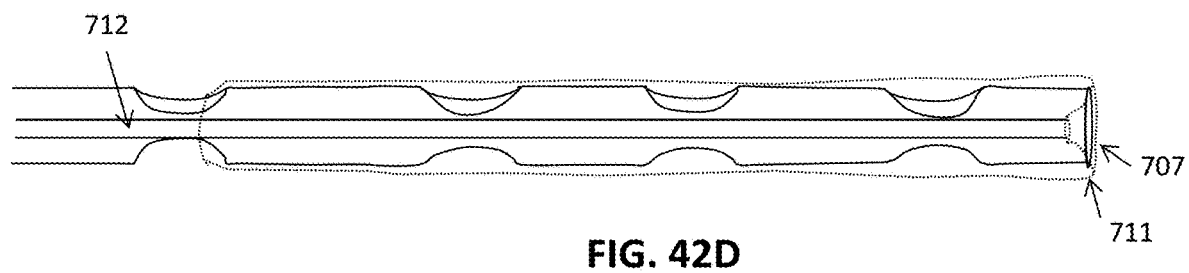
Figure 42E:
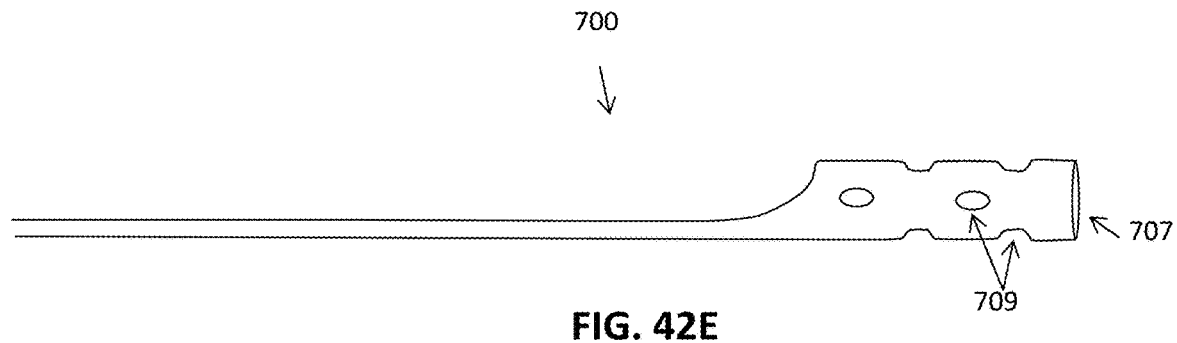
FIGS. 42E-42F illustrate another variation of a catheter of an elongate inversion support having a distal catheter region and an elongate support member formed by skive cutting the catheter.
Figure 42F:
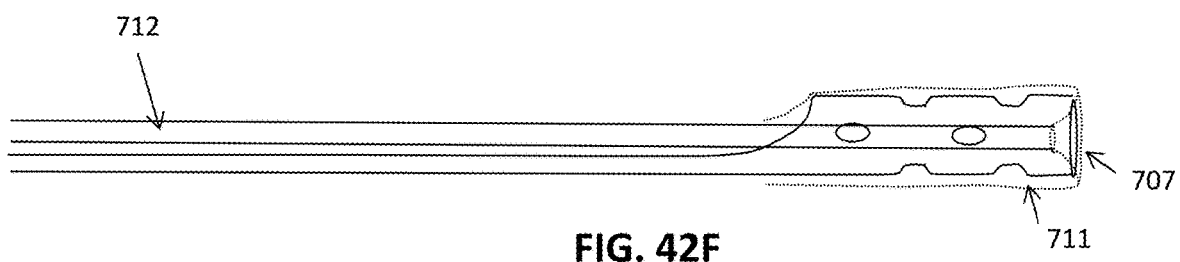
Figure 42G:
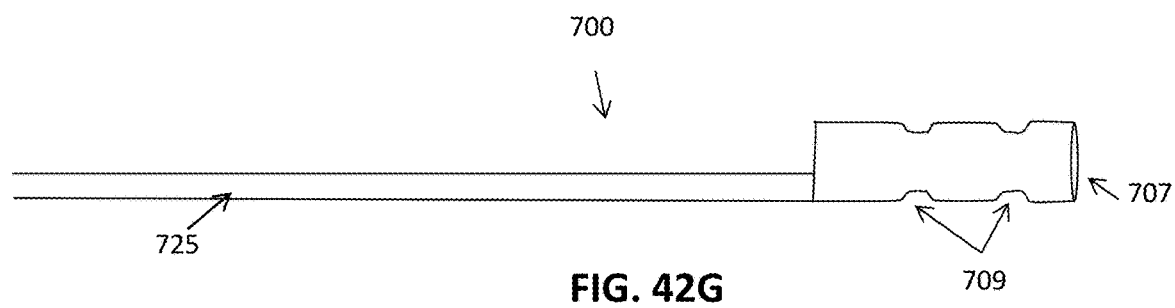
FIGS. 42G-42H illustrate another variation of an elongate inversion support having a distal catheter region and an elongate support member extending from the catheter region.
Figure 42H:
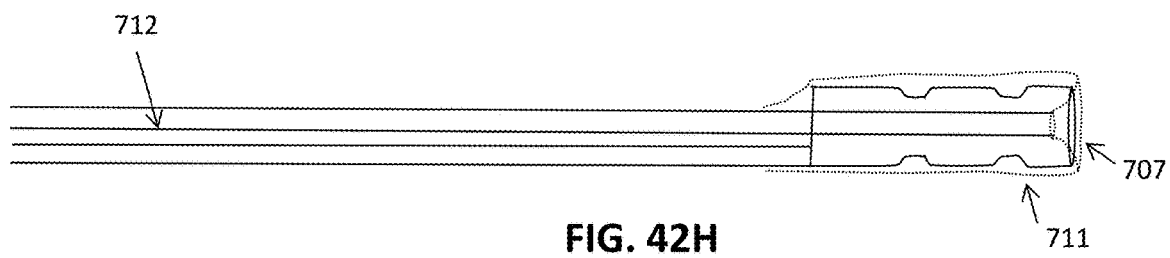
Figure 42I:
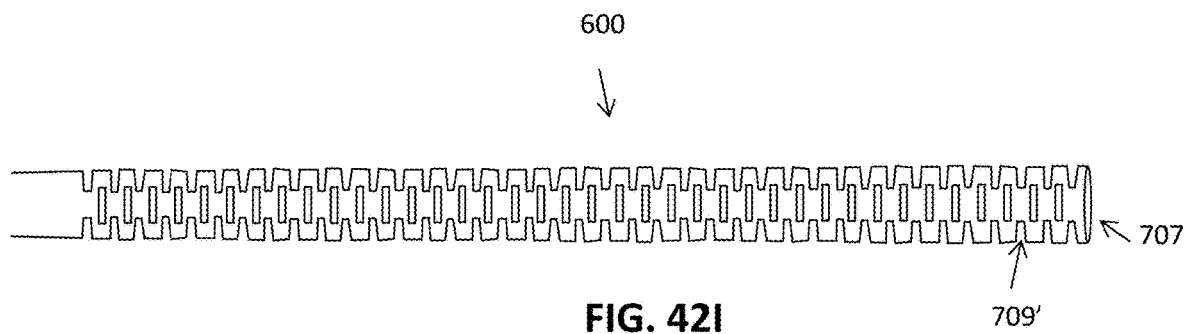
FIGS. 42I-42J illustrate another variation of an elongate inversion support having a plurality or openings along the distal-to-proximal length.
Figure 42J:
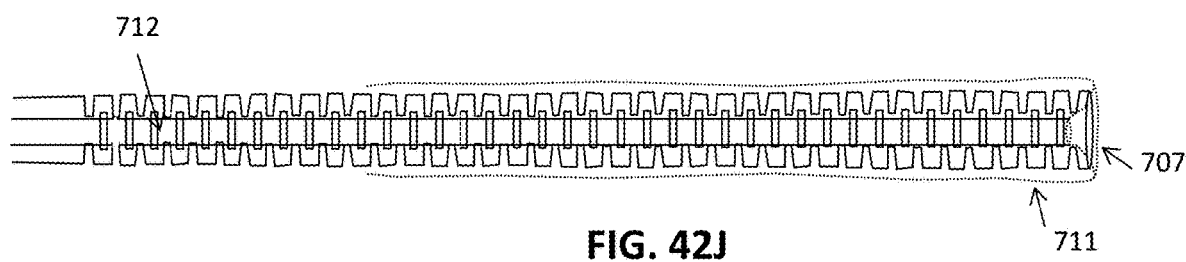

Similarly, in FIGS. 42B and 42C, the entire length of the elongate inversion support includes a plurality of cut-out regions 713 which may increase the ability to allow the flow of a vacuum or other fluid within the apparatus, but may still allow the elongate inversion support to provide column strength to resist collapsing up to at least 500 g of compressive longitudinal force applied by, e.g., pulling on the tractor. Similarly, the elongate inversion support of FIGS. 42E and 42F show a skived catheter that also includes openings 709 along its length. The puller and tractor 412 are shown within the elongate inversion support in FIG. 42F. FIGS. 42G and 42H illustrate an example in which rather than a skived portion of the catheter, the distal catheter region of the elongate inversion support is formed by a wire, bar, tube, 721 etc., that is attached to the catheter at the distal end. The catheter may also optionally include openings 709. The elongate inversion support of FIGS. 42I and 42J includes openings 709' along all or much of its length (particularly near the distal end region) as shown.

Figure 42K:
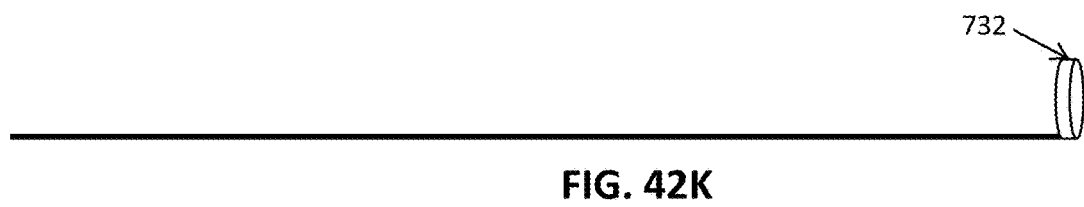
FIGS. 42K-42L illustrate another variation of an elongate inversion support having a minimal catheter region at the distal end forming a distal end opening that is connected to an elongate support (e.g., wire, tube, bar, rod, etc.).
Figure 42L:
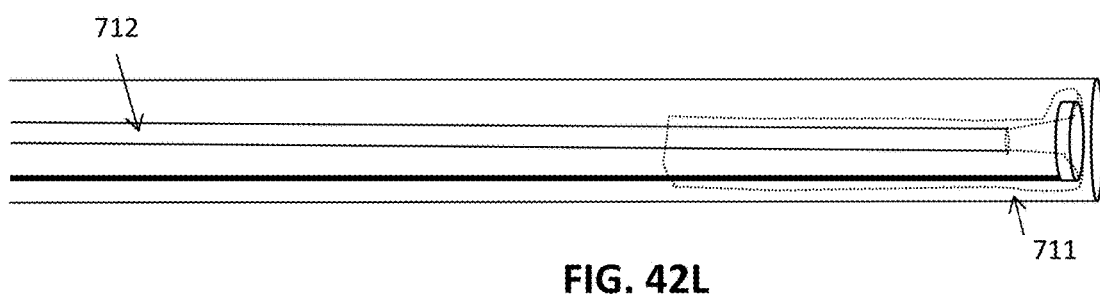

Finally, the variation of the elongate inversion support shown in FIG. 42K includes a minimal catheter portion 732 that is connected to a wire, bar, tube, hypotube, skived region, etc.

Figure 43A:
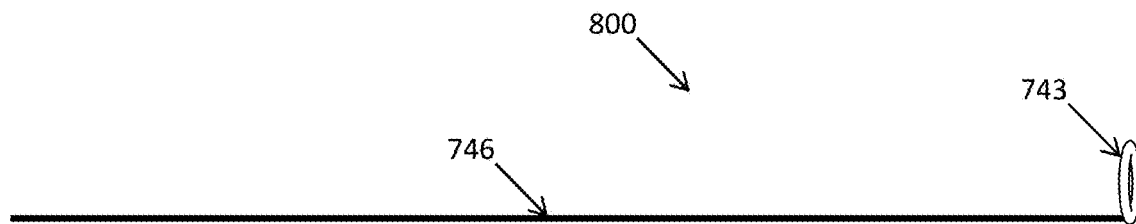
FIG. 43A is another variation of an elongate inversion support having a minimal catheter region at the distal end.
Figure 43B:
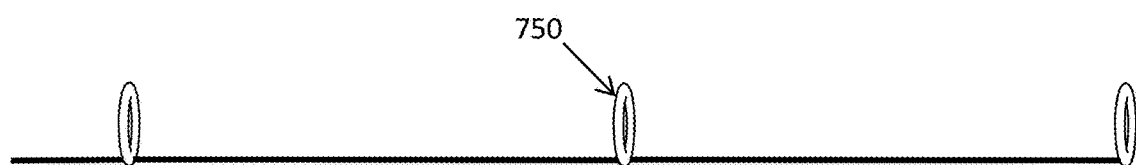
FIGS. 43B-43D illustrate an elongate inversion support such as the one shown in FIG. 43A having additional supports (FIG. 43B) and used as part of a mechanical thrombectomy apparatus (FIGS. 43C and 43D).
Figure 43C:
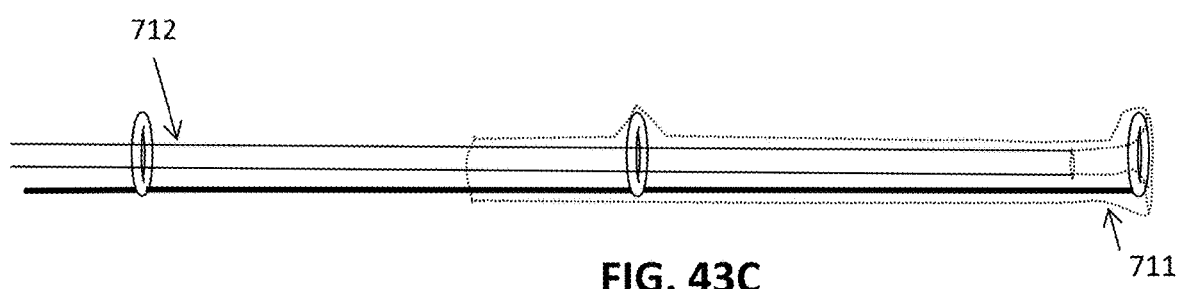
Figure 43D:
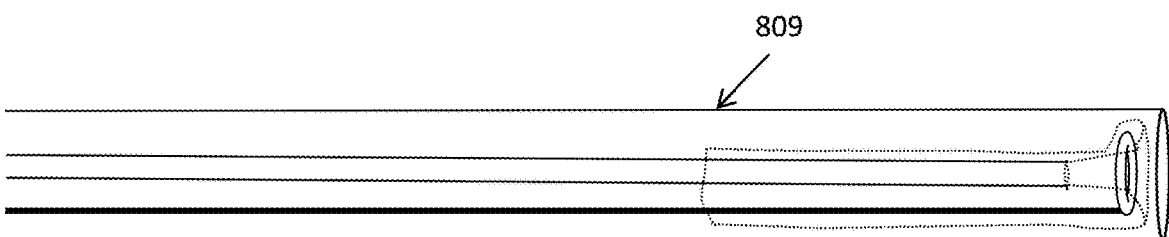

FIGS. 43A-43D illustrate the operation of a similar minimal elongate inversion support 800. In this example, the apparatus includes a distal aperture 743 bonded securely to a wire, bar, tube, hypotube, skived region, etc. 746 forming an elongate support. The elongate support may be hollow (e.g., may include a lumen for a guidewire) or solid. The elongate support may also include one or more additional support guides 750 as shown in FIG. 43B. These supports may help contain the puller and/or tractor within the elongate inversion support. Any of the elongate inversion supports described herein may include additional support guides. The elongate inversion support of FIG. 8B is shown with a tractor 711 and puller 712 in FIG. 43C. As mentioned, this variation may be particularly well suited for use with an intermediate (e.g., "outer") catheter, sleeve, or the like 809, as shown in FIG. 43D.

Power Driven Tractors

Figure 38A:
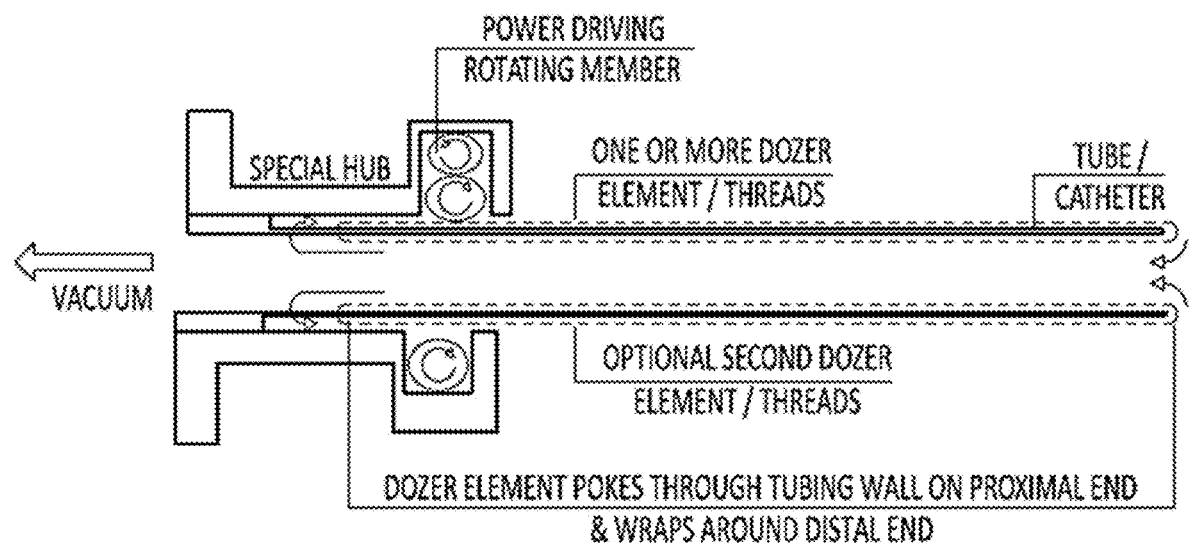
FIGS. 38A-38B show an example of an apparatus having a motor-driven tractor.
Figure 38B:
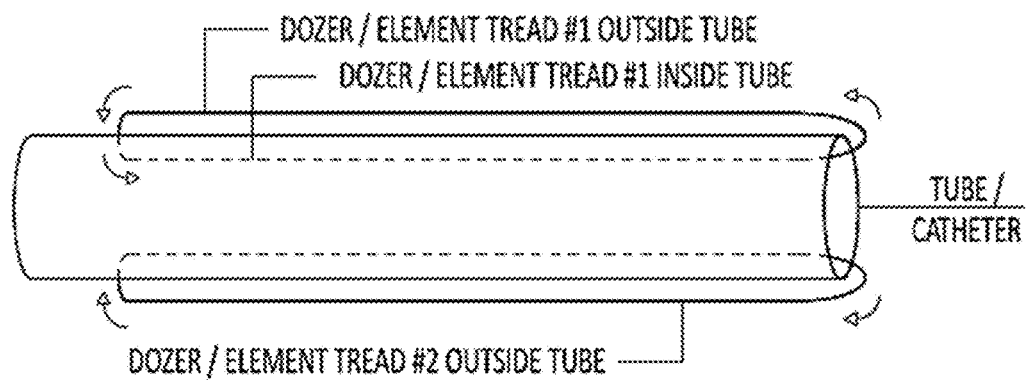
Figure 39A:
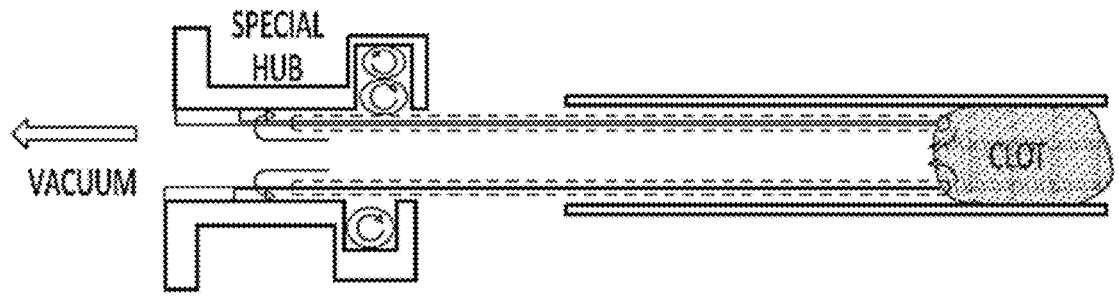
FIGS. 39A-39C illustrate operation of the apparatus of FIGS. 38A-38B.
Figure 39B:
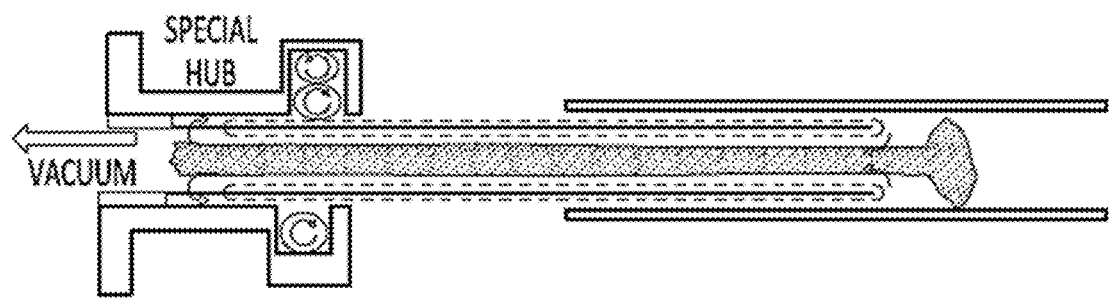
Figure 39C:
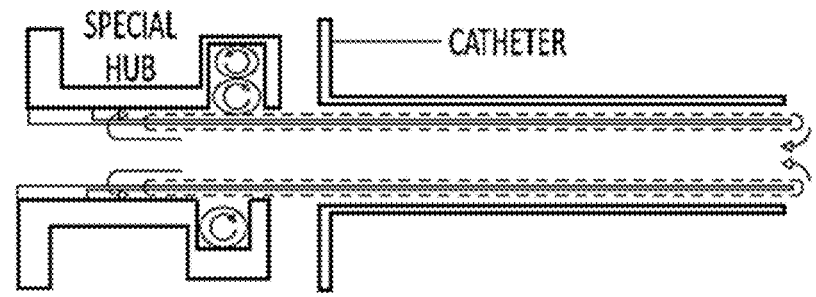

Also described herein are mechanical thrombectomy apparatuses in which the tractor is power driven. Any of the tractors described herein may also be driven by a motor, instead of or in addition to the manual driven tractor described. For example, a power-driven tractor may is shown in FIGS. 38A-38B and 39A-39C. In FIG. 38A the tractor is a continuous tractor. FIG. 38B illustrates the catheter and tractor region, without the motor shown in FIG. 38A. The tractor comprises a plurality of belts, chains, lengths, etc. that run longitudinally and may act like a conveyor to pull clot into the apparatus. The loops of material may therefore be run as a power-driven tractor. FIGS. 39A-39C illustrate the operation of the apparatus of FIGS. 38A-38B, shown grabbing a clot.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

Expandable Distal Ends

Figure 44A:
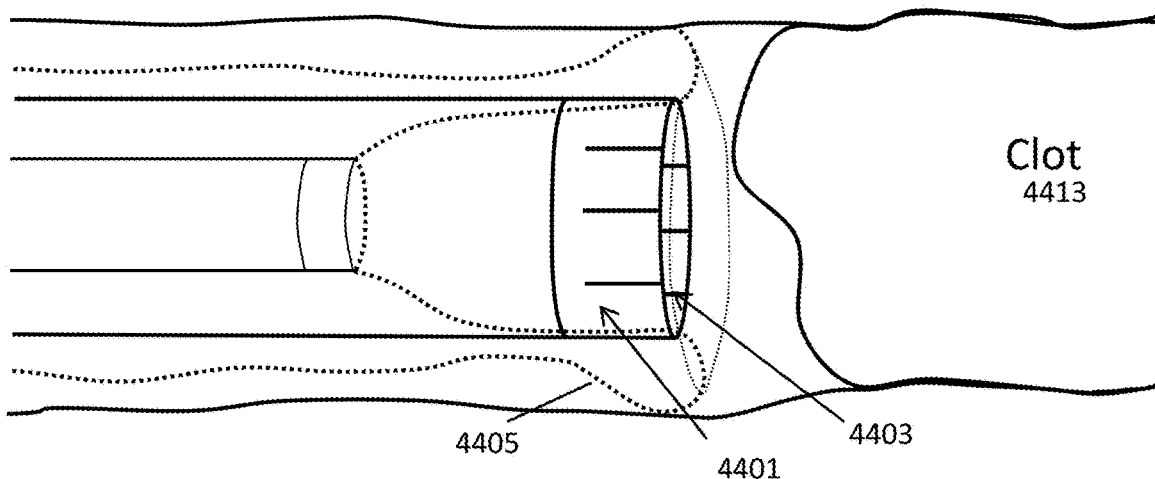
FIGS. 44A-44C illustrates an example of the operation of a mechanical thrombectomy apparatus with an expandable distal end region.
Figure 44B:
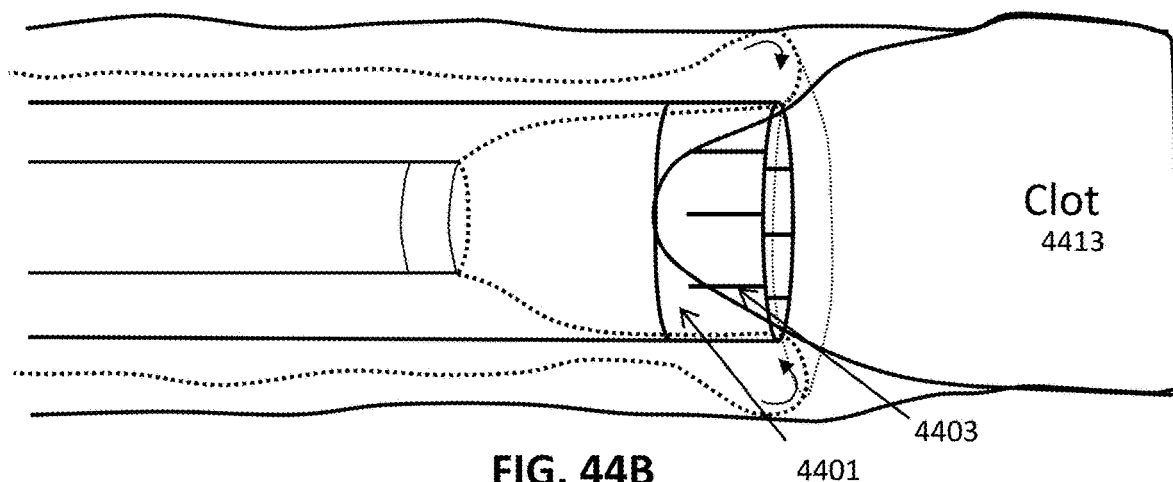
Figure 44C:
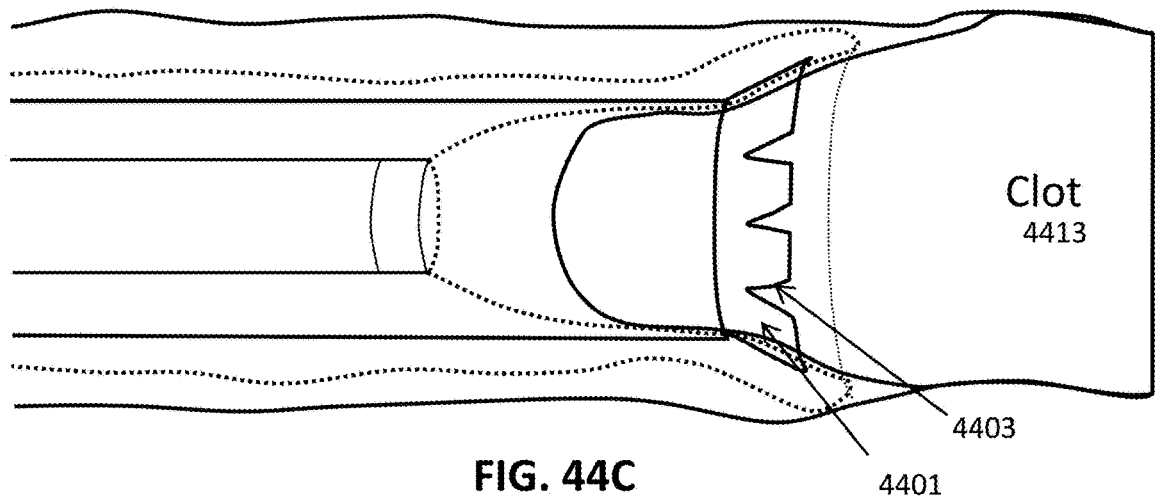

Any of the mechanical thrombectomy apparatuses described herein may include an elongate inversion support having a distal end that is expandable from a smaller diameter aperture (e.g., distal end opening) to a larger-diameter aperture. This expansion may be performed by pulling the clot within the catheter. For example, FIGS. 44A-44C illustrates the operation of an example of an elongate inversion support configured as a catheter having an expandable distal end. In this variation the catheter distal end 4401 may include slots or slits 4403 formed or cut, e.g., by laser-cutting, in the distal end of the catheter of the elongate inversion support. The apparatus may be operated as described above, positioning near (e.g., against or adjacent to) a clot, and pulling proximally on the puller to draw the tractor 4405 into the catheter, as shown in FIG. 44B. Although the apparatuses described herein may generally compress a clot greatly, compression may be made easier and/or more efficient by providing a more gradual decrease in radial diameter. As shown in FIG. 44B, when the tractor is rolled over the distal end opening and inverted, the clot maybe drawn in along with the tractor. As the large clot 4413 is brought into the distal end opening, the distal end opening may expand and open along the slots or slits 4403, as shown in FIG. 44C, so that the distal end opening flares out. In some variations an elastic sleeve, gasket, ring or cover (not shown in FIG. 44A-44C) may be included at least partially covering the distal end to prevent the edge from catching the tractor. For example, and elastic or stretchable layer may cover the cut distal end so that the distal end may be opened to form an outward flare. In FIG. 44C the outward-flared distal end is shown forming a funnel-shape into which the clot may be pulled. This funnel-shaped opening may help compress the clot so that it may be drawn into the mechanical thrombectomy apparatus.

In some variations the elongate inversion support may be configured to have, or to assume, a funnel-shape at the distal-facing end. The distal-facing end may always have a funnel-shaped mouth at the distal end opening, or the distal end opening may be configured to assume a funnel shape, as shown in FIGS. 44A-44C. In some variations the distal end of the elongate inversion support is configured to be elastic in a radial directly, but maintain stiffness along the proximal-to-distal axis (in compressive load). For example, the distal end of the elongate inversion support may be configured with strands or rods extending in the proximal-to-distal axis that have a high compressive load strength, but which may separate from each other to enlarge the distal end opening; for example they may be connected by rings in which more distal rings are more elastic/stretchable than more proximal rings.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of removing a clot using a mechanical thrombectomy apparatus, the method comprising:
  positioning a distal end of the mechanical thrombectomy apparatus adjacent to a clot within a vessel, wherein the mechanical thrombectomy apparatus includes a tractor region that extends along a distal region of a catheter and inverts over a distal end of the catheter so that a first end of the tractor extends proximally within the catheter, wherein the tractor comprises a plurality of ribbons having a square or rectangular cross-section;
  pulling the first end of the tractor proximally within the catheter to roll the tractor over the distal end of the catheter so that the tractor inverts over the distal end of the catheter and extends a plurality of edges of the ribbons, forming a plurality of projections from an inverting portion of the tractor as the tractor is rolled over the distal end of the catheter;
  grabbing the clot with the plurality of projections; and
  drawing the clot into the catheter.

2. The method of claim 1, further comprising macerating the clot with the plurality of projections.

3. The method of claim 1, further comprising sliding a loose second end of the tractor over the catheter as the first end of the tractor is pulled proximally.

4. The method of claim 1, wherein positioning the distal end of the mechanical thrombectomy apparatus adjacent to a clot within a vessel comprises sliding the mechanical thrombectomy apparatus over a guidewire.

5. The method of claim 1, further comprising releasing a releasable attachment between the tractor and an outer surface of the catheter.

6. The method of claim 1, wherein pulling the first end of the tractor proximally comprises maintaining an inner diameter of the tractor within the catheter at greater than 60% of an inner diameter of the catheter to prevent the tractor from locking over the distal end of the catheter.

7. A method of removing a clot using a mechanical thrombectomy apparatus, the method comprising:
  positioning a distal end of the mechanical thrombectomy apparatus adjacent to a clot within a vessel, wherein the mechanical thrombectomy apparatus includes a soft tractor region that extends along a distal region of a catheter and inverts over a distal end of the catheter so that a first end of the tractor extends proximally within the catheter, wherein the tractor is sufficiently soft such that without support from the catheter, the tractor collapses radially under an axial compression of less than 200 g of force when inverting;
  pulling the first end of the tractor proximally within the catheter to roll the tractor over the distal end of the catheter so that the tractor inverts over the distal end of the catheter and extends a plurality of projections from the tractor;
  grabbing the clot with the plurality of projections; and
  drawing the clot into the catheter.

8. The method of claim 7, further comprising macerating the clot with the plurality of projections.

9. The method of claim 7, wherein the tractor comprises a plurality of ribbons having a square or rectangular cross-section, further wherein pulling the first end of the tractor proximally within the catheter to roll the tractor over the distal end of the catheter comprises extending a plurality of edges of the ribbons from an inverting portion of the tractor as the tractor is rolled over the distal end of the catheter.

10. The method of claim 7, wherein the tractor comprises a plurality of cut-out regions formed in the tractor, wherein pulling the first end of the tractor proximally within the catheter to roll the tractor over the distal end of the catheter extends the cut-out regions from an inverting portion of the tractor as the tractor is rolled over the distal end of the catheter.

11. The method of claim 7, further comprising sliding a loose second end of the tractor over the catheter as the first end of the tractor is pulled proximally.

12. The method of claim 7, wherein positioning the distal end of the mechanical thrombectomy apparatus comprises sliding the mechanical thrombectomy apparatus over a guidewire.

13. The method of claim 7, further comprising releasing a releasable attachment between the tractor and an outer surface of the catheter.

14. The method of claim 7, wherein pulling the first end of the tractor proximally comprises maintaining an inner diameter of the tractor within the catheter at greater than 60% of an inner diameter of the catheter to prevent the tractor from locking over the distal end of the catheter.

* * * * *